(12) United States Patent
Wijdeven et al.

(10) Patent No.: US 12,397,063 B2
(45) Date of Patent: Aug. 26, 2025

(54) ANTIBODY-CONJUGATES FOR TARGETING OF TUMOURS EXPRESSING TROP-2

(71) Applicant: Synaffix B.V., Oss (NL)

(72) Inventors: Maria Antonia Wijdeven, Wijchen (NL); Jorge Merijn Mathieu Verkade, Eindhoven (NL); Jorin Hoogenboom, Wageningen (NL); Sander Sebastiaan Van Berkel, Wijchen (NL); Floris Louis Van Delft, Nijmegen (NL); Petrus Josephus Jacobus Maria Van De Sande, Eindhoven (NL)

(73) Assignee: Synaffix B.V., Oss (NL)

( * ) Notice: Subject to any disclaimer, the term of this patent is extended or adjusted under 35 U.S.C. 154(b) by 1112 days.

(21) Appl. No.: 17/307,447

(22) Filed: May 4, 2021

(65) Prior Publication Data

US 2021/0393792 A1 Dec. 23, 2021

Related U.S. Application Data

(63) Continuation of application No. PCT/EP2019/080295, filed on Nov. 5, 2019.

(30) Foreign Application Priority Data

Nov. 5, 2018 (EP) .................................. 18204269

(51) Int. Cl.
*A61K 47/68* (2017.01)

(52) U.S. Cl.
CPC ...... *A61K 47/6889* (2017.08); *A61K 47/6803* (2017.08); *A61K 47/68031* (2023.08); *A61K 47/68037* (2023.08); *A61K 47/6851* (2017.08)

(58) Field of Classification Search
None
See application file for complete search history.

(56) References Cited

U.S. PATENT DOCUMENTS

| | | | | |
|---|---|---|---|---|
| 7,238,785 | B2 * | 7/2007 | Govindan | A61P 31/00 435/69.6 |
| 9,427,464 | B2 * | 8/2016 | Nakamura | C07K 16/3046 |
| 9,850,312 | B2 * | 12/2017 | Agatsuma | A61K 31/4745 |
| 11,192,954 | B2 * | 12/2021 | Tang | A61K 47/68033 |
| 11,338,043 | B2 * | 5/2022 | Van Berkel | C07K 16/30 |
| 2004/0001825 | A1 | 1/2004 | Govindan et al. | |
| 2007/0212350 | A1 | 9/2007 | Govindan et al. | |
| 2008/0131363 | A1 | 6/2008 | Govindan et al. | |
| 2013/0344509 | A1 * | 12/2013 | Nakamura | A61P 35/04 536/23.53 |
| 2023/0330245 | A1 * | 10/2023 | Hoogenboom | C07D 491/22 |

FOREIGN PATENT DOCUMENTS

| | | |
|---|---|---|
| EP | 2 911 699 B1 | 9/2015 |
| EP | 3088419 B1 | 10/2018 |
| WO | WO-97/14796 A1 | 4/1997 |
| WO | WO-03/074566 A2 | 9/2003 |
| WO | WO-2007/095506 A1 | 8/2007 |
| WO | WO-2007/095748 A1 | 8/2007 |
| WO | WO-2007/095749 A1 | 8/2007 |
| WO | WO-2008/144891 A1 | 12/2008 |
| WO | 2009073546 A2 | 6/2009 |
| WO | WO-2011/155579 A1 | 12/2011 |
| WO | WO-2013/068946 A2 | 5/2013 |
| WO | WO-2013/077458 A1 | 5/2013 |
| WO | WO-2014065661 A1 * | 5/2014 ............. A61K 47/61 |
| WO | WO-2015/012904 A2 | 1/2015 |
| WO | WO-2015/098099 A1 | 7/2015 |
| WO | 2015168019 A2 | 11/2015 |
| WO | WO-2017/004144 A1 | 1/2017 |
| WO | 2017137456 A1 | 8/2017 |
| WO | 2017137458 A1 | 8/2017 |
| WO | WO-2017/137457 A1 | 8/2017 |
| WO | WO-2019/065964 A1 | 4/2019 |
| WO | 2020094670 A1 | 5/2020 |
| WO | 2022058395 A1 | 3/2022 |
| WO | 2023180484 A1 | 9/2023 |
| WO | 2023180485 A1 | 9/2023 |
| WO | 2023180489 A1 | 9/2023 |

OTHER PUBLICATIONS

Verkade et al (Antibodies (Basel) 7(1): 1-12 (Year: 2018).*
Lloyd et al., Protein Engineering, Design & Selection 22:159-168 (Year: 2009).*
Edwards et al., J Mol Biol 334(1): 103-118 (Year: 2003).*
Poosarla et al., Biotechnology and bioengineering. 114(6): 1331-1342 (Year: 2017).*
Strop et al., Chemistry and Biology 20: 161-167 (Year: 2013).*
Wu et al., J Mol Biol 294: 151-162 (Year: 1999).*

(Continued)

*Primary Examiner* — Phuong Huynh
(74) *Attorney, Agent, or Firm* — Dechert LLP; Andrew T. Wilkins; John P. Rearick

(57) ABSTRACT

The present invention concerns antibody-conjugate having general structure (2):

$$AB\text{-}[(L^6)\text{-}\{Z\text{-}(L^1)_n\text{-}(L_2)_o\text{-}(L^3)_p\text{-}(L^4)_q\text{-}D\}_{xx}]_{yy} \qquad (2)$$

wherein AB is an antibody capable of targeting Trop-2-expressing tumours and D is selected from the group consisting of taxanes, anthracyclines, camptothecins, epothilones, mytomycins, combretastatins, vinca alkaloids, maytansinoids, enediynes such as calicheamicins, duocarmycins, tubulysins, amatoxins, bleomycins, dolastatins and auristatins, pyrrolobenzodiazepine dimers, indolinobenzodiazepine dimers, radioisotopes, therapeutic proteins and peptides (or fragments thereof), kinase inhibitors, MEK inhibitors, KSP inhibitors, and analogues or prodrugs thereof. These antibody-conjugates exhibit an improved therapeutic index. The invention further concerns a process for preparing the antibody-conjugate according to the invention, a method for targeting Trop-2-expressing cells, medical uses of the antibody-conjugates according to the invention.

21 Claims, 8 Drawing Sheets

Specification includes a Sequence Listing.

(56) References Cited

OTHER PUBLICATIONS

Rudikoff et al., Proc. Natl. Acad. Sci. USA, 79(6):1979-1983 (Year: 1982).*

Dufner et al., Trends Biotechnol 24(11): 523-529 (Year: 2006).*

International Search Report and Written Opinion issued for PCT/EP2019/080295 mailed Jan. 31, 2020 (12 pages).

Strop et al., "RN927C, a Site-Specific Trop-2 Antibody-Drug Conjugate (ADC) with Enhanced Stability, Is Highly Efficacious in Preclinical Solid Tumor Models", Molecular Cancer Therapeutics, vol. 15, No. 11, Aug. 31, 2016, pp. 2698-2708.

Damelin et al.,"A PTK7-targeted antibody-drug conjugate reduces tumor-initiating cells and induces sustained tumor regressions," Sci Transl Med. 2017;9(372):eaag2611.

Dotan et al., "Phase I/II Trial of Labetuzumab Govitecan (Anti-CEACAM5/SN-38 Antibody-Drug Conjugate) in Patients With Refractory or Relapsing Metastatic Colorectal Cancer," J Clin Oncol. 2017;35(29):3338-3346.

Gazzah et al., "Safety, pharmacokinetics, and antitumor activity of the anti-CEACAM5-DM4 antibody-drug conjugate tusamitamab ravtansine (SAR408701) in patients with advanced solid tumors: first-in-human dose-escalation study," Ann Oncol. 2022;33(4):416-425.

International Search Report and Written Opinion from PCT/EP2023/057560 mailed Jul. 4, 2023.

International Search Report and Written Opinion from PCT/EP2023/057561 mailed Jul. 4, 2023.

International Search Report and Written Opinion from PCT/EP2023/057565 mailed Jul. 7, 2023.

Okajima et al., "Datopotamab Deruxtecan, a Novel TROP2-directed Antibody-drug Conjugate, Demonstrates Potent Antitumor Activity by Efficient Drug Delivery to Tumor Cells," Mol Cancer Ther. 2021;20(12):2329-2340.

U.S. Appl. No. 18/892,253, Lelieveldt et al., filed Sep. 20, 2024.

U.S. Appl. No. 18/892,256, Lelieveldt et al., filed Sep. 20, 2024.

U.S. Appl. No. 18/892,270, Wijdeven et al., filed Sep. 20, 2024.

Van Geel et al., "Chemoenzymatic Conjugation of Toxic Payloads to the Globally Conserved N-Glycan of Native mAbs Provides Homogeneous and Highly Efficacious Antibody-Drug Conjugates," Bioconjug Chem. 2015;26(11):2233-42.

* cited by examiner

SEQUENCE LISTING

<160> NUMBER OF SEQ ID NOS: 6

<210> SEQ ID NO 1
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Thr Ser
            20                  25                  30

Ile His Trp Tyr Gln Gln Lys Pro Gly Gln Ala Pro Arg Leu Leu Ile
        35                  40                  45

Lys Tyr Ala Ser Glu Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asn Ser Trp Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 445

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ile Tyr
            20                  25                  30

Trp Ile Asn Trp Val Arg Gln Ala Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Thr Ser Met Ala Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

```
Pro Glu Asn Asn Tyr Lys Thr Thr Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 3
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Gln Leu Thr Gln Ser Pro Ser Ser Leu Ser Ala Ser Val Gly
1               5                   10                  15

Asp Arg Val Ser Ile Thr Cys Lys Ala Ser Gln Asp Val Ser Ile Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ile Thr Pro Leu
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Gln Gln Ser Gly Ser Glu Leu Lys Lys Pro Gly Ala
1               5                   10                  15
```

```
Ser Val Lys Val Ser Cys Lys Ala Ser Gly Tyr Thr Phe Thr Asn Tyr
         20              25                  30

Gly Met Asn Trp Val Lys Gln Ala Pro Gly Gln Gly Leu Lys Trp Met
         35              40                  45

Gly Trp Ile Asn Thr Tyr Thr Gly Glu Pro Thr Tyr Thr Asp Asp Phe
 50              55                  60

Lys Gly Arg Phe Ala Phe Ser Leu Asp Thr Ser Val Ser Thr Ala Tyr
 65              70                  75                      80

Leu Gln Ile Ser Ser Leu Lys Ala Asp Asp Thr Ala Val Tyr Phe Cys
                 85              90                  95

Ala Arg Gly Gly Phe Gly Ser Ser Tyr Trp Tyr Phe Asp Val Trp Gly
             100             105                 110

Gln Gly Ser Leu Val Thr Val Ser Ser Ala Ser Thr Lys Gly Pro Ser
         115             120                 125

Val Phe Pro Leu Ala Pro Ser Ser Lys Ser Thr Ser Gly Gly Thr Ala
130             135                 140

Ala Leu Gly Cys Leu Val Lys Asp Tyr Phe Pro Glu Pro Val Thr Val
145             150                 155                     160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

His Glu Ala Leu His Asn His Tyr Thr Gln Lys Ser Leu Ser Leu Ser
            435                 440                 445

Pro Gly Lys
    450

<210> SEQ ID NO 5
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ile Thr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Ala
            20                  25                  30

Gly Met Gln Trp Val Arg Gln Ala Pro Gly Gln Gly Leu Glu Trp Met
        35                  40                  45

-continued

Gly Trp Ile Asn Thr His Ser Gly Val Pro Lys Tyr Ala Glu Asp Phe
    50                      55                  60

Lys Gly Arg Val Thr Ile Ser Ala Asp Thr Ser Thr Ser Thr Ala Tyr
 65             70                  75                  80

Leu Gln Leu Ser Ser Leu Lys Ser Glu Asp Thr Ala Val Tyr Tyr Cys
                85                  90                  95

Ala Arg Ser Gly Phe Gly Ser Ser Tyr Trp Tyr Phe Asp Val Trp Gly
            100                 105                 110

Gln Gly Thr Leu Val Thr Val Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

ANTIBODY-CONJUGATES FOR TARGETING OF TUMOURS EXPRESSING TROP-2

CROSS-REFERENCE TO RELATED APPLICATIONS

This application is a continuation of International Application No. PCT/EP2019/080295, filed Nov. 5, 2019, which claims the benefit of and priority to European Application No. 18204269.7, filed Nov. 5, 2018, both of which are hereby incorporated by reference herein in their entireties.

SEQUENCE LISTING

The instant application contains a Sequence Listing which has been submitted electronically in ASCII format and is hereby incorporated by reference in its entirety. Said ASCII copy, created on Sep. 7, 2021, is named 069818-0620_SL.txt and is 18,174 bytes in size.

FIELD OF THE INVENTION

The present invention is in the field of bioconjugation. More specifically, the present invention relates to antibody-drug conjugates for targeted treatment of patients with cancer, in particular Trop-2-expressing tumours.

BACKGROUND OF THE INVENTION

Proteins that have roles in breast cancer growth, differentiation, invasion and/or metastasis can influence the biological progress of tumours and can thus provide important prognostic information. One such candidate is Trop-2 (GA733-1, EGP-1), a 45 kDa monomeric trans-membrane glycoprotein that belongs to the TACSTD gene family, specifically TACSTD2, which is expressed in human epithelial cells at diverse stages of differentiation. Over-expression of Trop-2 has been demonstrated to be necessary and sufficient to stimulate tumour growth and has been linked to an overall poor prognosis. Expression of Trop-2 is associated with poor prognosis of several human cancers, including oral, pancreatic, gastric, ovarian, colorectal, breast and lung tumours. For example, Trop-2 overexpression was observed in 55% of pancreatic cancer patients studied, with a positive correlation with metastasis, tumour grade, and poor progression-free survival of patients who underwent surgery with curative intent. Likewise, in gastric cancer, 56% of patients may exhibit Trop-2 overexpression on their tumours, which again correlated with shorter disease-free survival and a poorer prognosis in those patients with lymph node involvement of Trop-2-positive tumour cells.

Given these characteristics and the fact that Trop-2 is linked to so many intractable cancers, Trop-2 is an attractive target for therapeutic intervention. Nevertheless, it has to be taken into consideration that Trop-2 is also expressed in some normal tissues, although usually at much lower intensities when compared to those in neoplastic tissue, and often in regions of the tissues with restricted vascular access.

Several monoclonal antibodies against Trop-2 have been established. Some anti-Trop-2 monoclonal antibodies such as 77220 are commercially available as reagents. Some of these established anti-Trop-2 monoclonal antibodies are being under investigation for treating cancers. Most of the anti-Trop-2 monoclonal antibodies at present available on the market, e.g. T16, have been generated using myeloma cell lines such as NS-I or SP2-1 as fusion partners, which retains the expression of the parental immunoglobulin light chain. This caused these antibodies to be actually heterogeneous mixtures of antibodies with one, both or neither light chain directly participating in Trop-2 recognition.

WO 97/14796 describes a monoclonal antibody, BR110, which is known to bind to Trop-2 on the cell surface and internalize within the cells. Patent applications WO 2003/074566, US 2004/001825, US 2007/212350 and US 2008/131363 teach RS7 antibodies and their uses in the treatment and diagnosis of tumours. These applications further relate to humanized, human and chimeric RS7 antigen binding proteins (hRS7), and the use of such binding proteins in diagnosis and therapy. Anti-Trop-2 monoclonal antibody AR47A6.4.2 is disclosed in WO 2007/095748 and AR52A301.5 is disclosed in WO 2007/095749, both of which are antibodies that specifically injure Trop-2-expressing cancer cell as a target cell to exhibit effects.

Patent application WO 2008/144891 teaches a humanized version of AR47A6.4.2 as anti-Trop-2 monoclonal antibody for the treatment of tumours. Patent application WO 2011/155579 (Sapporo) teaches a monoclonal antibody or an antibody fragment thereof, which binds to the extracellular region of human Trop-2 with high affinity and exhibits high ADCC activity and high antitumor activity. Patent application WO2013/077458 (LivTech/Chiome) teaches anti-human Trop-2 antibodies with antitumor activity, in particular humanized antibodies including Huk5-70-2, especially having anti-tumour activity in vivo. Patent application WO 2013/068946 (Rinat/Pfizer) teaches antibodies that specifically bind to trophoblast cell-surface antigen-2 (Trop-2). The invention further relates to therapeutic methods for use of these antibody conjugates for the treatment of a condition associated with Trop-2 expression (e.g., cancer), such as colon, esophageal, gastric, head and neck, lung, ovarian, or pancreatic cancer.

One promising application of antibodies for the targeted treatment of tumours entails the conjugation of a multitude (2 to 8) of highly toxic payloads to the antibody, thereby generating an antibody-drug conjugate (ADCs). ADCs are well known in the art, as for example described by Chari et al. (*Angew. Chem. Int. Ed.* 2014, 53, 3796) and Beck et al. (*Nat Rev Drug Discov.* 2017, 16, 315-37). Mechanistically, the antibody is designed to bind with high specificity to tumour-associated receptor that is overexpressed versus healthy tissue. The ADC is thought to internalize into the tumour cell after binding to the receptor, then to release the toxic payload upon degradation of the antibody and/or the linker in the lysosome.

ADCs targeting Trop-2 are known in the art and are at various stages of clinical development. IMMU-132 is an ADC derived from humanized antibody hRS7, conjugated to campthothecin analogue SN-38 through an acid-cleavable linker CL2A, as disclosed in WO 2015/012904, and is currently in late stage clinical development for treatment of a range of clinical indication, including (triple negative) breast cancer, small-cell lung cancer and pancreatic cancer. DS-1062a is an ADC derived from humanized antibody hTINA, conjugated to campthothecin analogue exatecan through an protease-sensitive cleavable linker WO 2015/098099, and is under clinical evaluation for treatment of solid tumours. Thirdly, PF-06664178 is an ADC derived from monoclonal antibody RN926, site-specifically conjugated to auristatin analogue PF-06380101 under the action of microbial transglutaminase. PF-06664178 has been evaluated in a phase I clinical study in patients with advanced or metastatic solid tumours, however the ADC showed toxicity at high dose levels with only modest antitumor activity, so development was discontinued.

Current ADCs are prepared by various conjugation technologies (summarized in FIG. 1), mostly based on conjugation to cysteine side chains with maleimides or to lysine side chains with activated esters. Reaction of cysteine side chain with vinylbenzene derivative has also been reported. Besides reaction to natural amino acid side chains, specific unnatural (non-canonical) amino acids can also be engineered into the amino acid sequence of an antibody, thereby providing a unique handle for chemical conjugation, such as ketone, acetylene, azide, cyclic alkyne or cyclic alkene, for reaction with oxime, azide, alkyne or tetrazine, respectively. However, a disadvantage of the latter approach is that the natural sequence of the antibody has to be re-engineered, which besides being time-consuming and costly, may lead to instability issues.

Conjugation through the glycan by an oxidation-ligation sequence is known in the art and has for example been described by Hamann et al. (*Bioconjugate Chem.* 2002, 13, 47-58).

Chemoenzymatic conjugation through the glycan is known in the art and has been described fur the use of sialyltransferase by Boons et al, *Angew. Chem. Int. Ed.* 2014, 53, 7179, and for the use of a mutant galactosyltransferase by Zhu et al, mAbs 2014, 6, 1 and Cook et al, *Bioconjugate Chem.* 2016, 27, 1789.

Chemoenzymatic conjugation through the glycan including first trimming of the glycan is known in the art and has been described by van Geel et al, *Bioconjugate Chem.* 2015, 26, 2233 and is schematically depicted in FIG. 2. In short, the monoclonal antibody is treated with an endoglycosidase to trim the glycan down to the core GlcNAc (attached directly to Asn-297), followed by transfer of an azido-modified sugar under the action of a glycosyltransferase. Various structures of UDP-azidosugars are depicted in FIG. 3. One particularly suitable combination involves that transfer of GalNAz 11b (2-azidoacetyl-N-galactosamine) under the action of a mutant galactosyltransferase GalT(Y289L) was disclosed in WO 2007/095506, EP 2911699 B1 and van Geel et al. An alternative powerful combination entails 6-azidoGalNAc 11d with native GalNAc-transferase, as has been disclosed in PCT/EP2016/059194.

Various cyclooctynes for application in metal-free click chemistry are known in the art (FIG. 4). In particular, various cyclooctynes such as DIBO (I), DBCO/DIBAC (J) and BCN (L) are regularly applied for conjugation to azide.

SUMMARY OF THE INVENTION

In a first aspect, the present invention concerns an antibody-conjugate. Related thereto, in a second aspect, the invention concerns a process for preparing the antibody-conjugate according to the invention. In a third aspect, the invention concerns a method for targeting Trop-2-expressing cells. Related thereto are the first medical use of the antibody-conjugate according to the invention, as well as the second medical use for the treatment of cancer. In a last aspect, the invention concerns the use of a mode of conjugation for increasing the therapeutic index of an antibody-conjugate in the treatment of Trop-2-expressing tumours.

The antibody-conjugate according to the invention is of general structure (2):

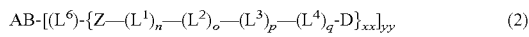

$$AB\text{-}[(L^6)\text{-}\{Z\text{---}(L^1)_n\text{---}(L^2)_o\text{---}(L^3)_p\text{---}(L^4)_q\text{-}D\}_{xx}]_{yy} \quad (2)$$

wherein:
AB is an antibody capable of targeting Trop-2-expressing tumours;

$L^1$, $L^2$, $L^3$ and $L^4$ are each individually linkers that together link Z to D;
n, o, p and q are each individually 0 or 1, provided that n+o+p+q=1, 2, 3 or 4;
Z is a connecting group;
$L^6$ is -GlcNAc(Fuc)$_w$-S—($L^7$)$_{w'}$—, wherein S is a sugar or a sugar derivative, GlcNAc is N-acetylglucosamine and Fuc is fucose, w is 0 or 1, w' is 0, 1 or 2, and $L^7$ is —N(H)C(O)CH$_2$—, —N(H)C(O)CF$_2$— or —CH$_2$—;
D is selected from the group consisting of taxanes, anthracyclines, camptothecins, epothilones, mytomycins, combretastatins, vinca alkaloids, maytansinoids, enediynes such as calicheamicins, duocarmycins, tubulysins, amatoxins, bleomycins, dolastatins and auristatins, pyrrolobenzodiazepine dimers, indolinobenzodiazepine dimers, radioisotopes, therapeutic proteins and peptides (or fragments thereof), kinase inhibitors, MEK inhibitors, KSP inhibitors, and analogues or prodrugs thereof;
xx is 1 or 2; and
yy is 1, 2, 3 or 4.

The inventors have surprisingly found that the antibody-conjugates according to the invention are superior to conventional Trop-2-targeting antibody-conjugates in terms of safety and/or efficacy, such that the therapeutic index of the antibody-conjugate according to the invention is increased with respect to conventional Trop-2-targeting antibody-conjugates.

DETAILED DESCRIPTION

In a first aspect, the present invention concerns an antibody-conjugate. Related thereto, in a second aspect, the invention concerns a process for preparing the antibody-conjugate according to the invention. In a third aspect, the invention concerns a method for targeting Trop-2-expressing cells. Related thereto are the first medical use of the antibody-conjugate according to the invention, as well as the second medical use for the treatment of cancer. In a last aspect, the invention concerns the use of a mode of conjugation for increasing the therapeutic index of an antibody-conjugate in the treatment of Trop-2-expressing tumours.

Definitions

The verb "to comprise", and its conjugations, as used in this description and in the claims is used in its non-limiting sense to mean that items following the word are included, but items not specifically mentioned are not excluded.

In addition, reference to an element by the indefinite article "a" or "an" does not exclude the possibility that more than one of the element is present, unless the context clearly requires that there is one and only one of the elements. The indefinite article "a" or "an" thus usually means "at least one".

The term "glycoprotein" is herein used in its normal scientific meaning and refers to a protein comprising one or more monosaccharide or oligosaccharide chains ("glycans") covalently bonded to the protein. A glycan may be attached to a hydroxyl group on the protein (O-linked-glycan), e.g. to the hydroxyl group of serine, threonine, tyrosine, hydroxylysine or hydroxyproline, or to an amide function on the protein (N-glycoprotein), e.g. asparagine or arginine, or to a carbon on the protein (C-glycoprotein), e.g. tryptophan. A glycoprotein may comprise more than one glycan, may comprise a combination of one or more monosaccharide and one or more oligosaccharide glycans, and may comprise a combination of N-linked, O-linked and C-linked glycans. It is estimated that more than 50% of all proteins have some form of glycosylation and therefore qualify as glycoprotein. Examples of glycoproteins include PSMA (prostate-specific membrane antigen), CAL (candida antartica lipase), gp41, gp120, EPO (erythropoietin), antifreeze protein and antibodies.

The term "glycan" is herein used in its normal scientific meaning and refers to a monosaccharide or oligosaccharide chain that is linked to a protein. The term glycan thus refers to the carbohydrate-part of a glycoprotein. The glycan is attached to a protein via the C-1 carbon of one sugar, which may be without further substitution (monosaccharide) or may be further substituted at one or more of its hydroxyl groups (oligosaccharide). A naturally occurring glycan typically comprises 1 to about 10 saccharide moieties. However, when a longer saccharide chain is linked to a protein, said saccharide chain is herein also considered a glycan. A glycan of a glycoprotein may be a monosaccharide. Typically, a monosaccharide glycan of a glycoprotein consists of a single N-acetylglucosamine (GlcNAc), glucose (Glc), mannose (Man) or fucose (Fuc) covalently attached to the protein. A glycan may also be an oligosaccharide. An oligosaccharide chain of a glycoprotein may be linear or branched. In an oligosaccharide, the sugar that is directly attached to the protein is called the core sugar. In an oligosaccharide, a sugar that is not directly attached to the protein and is attached to at least two other sugars is called an internal sugar. In an oligosaccharide, a sugar that is not directly attached to the protein but to a single other sugar, i.e. carrying no further sugar substituents at one or more of its other hydroxyl groups, is called the terminal sugar. For the avoidance of doubt, there may exist multiple terminal sugars in an oligosaccharide of a glycoprotein, but only one core sugar. A glycan may be an O-linked glycan, an N-linked glycan or a C-linked glycan. In an O-linked glycan a monosaccharide or oligosaccharide glycan is bonded to an O-atom in an amino acid of the protein, typically via a hydroxyl group of serine (Ser) or threonine (Thr). In an N-linked glycan a monosaccharide or oligosaccharide glycan is bonded to the protein via an N-atom in an amino acid of the protein, typically via an amide nitrogen in the side chain of asparagine (Asn) or arginine (Arg). In a C-linked glycan a monosaccharide or oligosaccharide glycan is bonded to a C-atom in an amino acid of the protein, typically to a C-atom of tryptophan (Trp).

The term "antibody" (AB) is herein used in its normal scientific meaning. An antibody is a protein generated by the immune system that is capable of recognizing and binding to a specific antigen. An antibody is an example of a glycoprotein. The term antibody herein is used in its broadest sense and specifically includes monoclonal antibodies, polyclonal antibodies, dimers, multimers, multispecific antibodies (e.g. bispecific antibodies), antibody fragments, and double and single chain antibodies. The term "antibody" is herein also meant to include human antibodies, humanized antibodies, chimeric antibodies and antibodies specifically binding cancer antigen. The term "antibody" is meant to include whole antibodies, but also fragments of an antibody, for example an antibody Fab fragment, F(ab')$_2$, Fv fragment or Fc fragment from a cleaved antibody, a scFv-Fc fragment, a minibody, a diabody or a scFv. Furthermore, the term includes genetically engineered antibodies and derivatives of an antibody. Antibodies, fragments of antibodies and genetically engineered antibodies may be obtained by methods that are known in the art. Typical examples of antibodies include, amongst others, abciximab, rituximab, basiliximab, palivizumab, infliximab, trastuzumab, alemtuzumab, adalimumab, tositumomab, cetuximab, ibrituximab tiuxetan, omalizumab, bevacizumab, natalizumab, ranibizumab, panitumumab, eculizumab, certolizumab pegol, golimumab, canakinumab, catumaxomab, ustekinumab, tocilizumab, ofatumumab, denosumab, belimumab, ipilimumab and brentuximab.

A linker is herein defined as a moiety that connects (covalently links) two or more elements of a compound. A linker may comprise one or more spacer moieties. A spacer-moiety is herein defined as a moiety that spaces (i.e. provides distance between) and covalently links together two (or more) parts of a linker. The linker may be part of e.g. a linker-construct, a linker-conjugate, a linker-payload (e.g. linker-drug) or an antibody-conjugate, as defined below.

A "hydrophilic group" or "polar linker" is herein defined as any molecular structure containing one or more polar functional groups that imparts improved polarity, and therefore improved aqueous solubility, to the molecule it is attached to. Preferred hydrophilic groups are selected from a carboxylic acid group, an alcohol group, an ether group, a polyethylene glycol group, an amino group, an ammonium group, a sulfonate group, a phosphate group, an acyl sulfamide group or a carbamoyl sulfamide group. In addition to higher solubility other effects of the hydrophilic group include improved click conjugation efficiency, and, once incorporated into an antibody-drug conjugate: less aggregation, improved pharmacokinetics resulting in higher efficacy and in vivo tolerability.

The term "salt thereof" means a compound formed when an acidic proton, typically a proton of an acid, is replaced by a cation, such as a metal cation or an organic cation and the like. Where applicable, the salt is a pharmaceutically acceptable salt, although this is not required for salts that are not intended for administration to a patient. For example, in a salt of a compound the compound may be protonated by an inorganic or organic acid to form a cation, with the conjugate base of the inorganic or organic acid as the anionic component of the salt. The term "pharmaceutically accepted" salt means a salt that is acceptable for administration to a patient, such as a mammal (salts with counterions having acceptable mammalian safety for a given dosage regime). Such salts may be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions known in the art and include, for example, sodium, potassium, calcium, magnesium, ammonium, tetraalkylammonium, etc., and when the molecule contains a basic functionality, salts of organic or inorganic acids, such as hydrochloride, hydrobromide, formate, tartrate, besylate, mesylate, acetate, maleate, oxalate, etc.

The term "enediyne" or "enediyne antibiotic" or "enediyne-containing cytotoxin" refers to any cytotoxin characterized by the presence of a 3-ene-1,5-diyne structural feature as part of a cyclic molecule as known in the art and include neocarzinostatin (NCS), C-1027, kedarcidin (KED), maduropeptin (MDP), N1999A2, the sporolides (SPO), the cyanosporasides (CYA and CYN), and the fijiolides, calicheamicins (CAL), the esperamicins (ESP), dynemicin (DYN), namenamicin, shishijimicin, and uncialamycin (UCM).

The term "alkylaminosugar" as used herein means a tetrahydropyranyl moiety connected to an alcohol function via its 2-position, thereby forming an acetal function, and further substituted by (at least) one N-alkylamino group in position 3, 4 or 5. "N-alkylamino group" in this context refers to an amino group having one methyl, ethyl or 2-propyl group.

The term "click probe" refers to a functional moiety that is capable of undergoing a click reaction, i.e. two compatible click probes mutually undergo a click reaction such that they are covalently linked in the product. Compatible probes for click reactions are known in the art, and preferably include (cyclic) alkynes and azides. In the context of the present invention, click probe Q in the compound according to the invention is capable of reacting with click probe F on the (modified) protein, such that upon the occurrence of a click reaction, a conjugate is formed wherein the protein is conjugated to the compound according to the invention. Herein, F and Q are compatible click probes.

An "acylsulfamide moiety" is herein defined as a sulfamide moiety ($H_2NSO_2NH_2$) that is N-acylated or N-carbamoylated on one end of the molecule and N-alkylated (mono or bis) at the other end of the molecule. In the context of the present invention, especially in the examples, this group is also referred to as "HS".

In a first aspect, the invention concerns antibody-conjugates of general structure (2)

$$AB-[(L^6)-\{Z-(L^1)_n-(L^2)_o-(L^3)_p-(L^4)_q-D\}_{xx}]_{yy} \quad (2)$$

wherein:
AB is an antibody capable of targeting Trop-2-expressing tumours;
$L^1$, $L^2$, $L^3$ and $L^4$ are each individually linkers that together link Z to D;
n, o, p and q are each individually 0 or 1, provided that n+o+p+q=1, 2, 3 or 4;
Z is a connecting group;
$L^6$ is -GlcNAc(Fuc)$_w$-S—$(L^7)_{w'}$—, wherein S is a sugar or a sugar derivative, GlcNAc is N-acetylglucosamine and Fuc is fucose, w is 0 or 1, w' is 0, 1 or 2, and $L^7$ is —N(H)C(O)CH$_2$—, —N(H)C(O)CF$_2$— or —CH$_2$—;
D is selected from the group consisting of taxanes, anthracyclines, camptothecins, epothilones, mytomycins, combretastatins, vinca alkaloids, maytansinoids, enediynes such as calicheamicins, duocarmycins, tubulysins, amatoxins, bleomycins, dolastatins and auristatins, pyrrolobenzodiazepine dimers, indolinobenzodiazepine dimers, radioisotopes, therapeutic proteins and peptides (or fragments thereof), kinase inhibitors, MEK inhibitors, KSP inhibitors, and analogues or prodrugs thereof;
xx is 1 or 2; and
yy is 1, 2, 3 or 4.

Also contemplated within the present invention are salts, preferably pharmaceutically acceptable salts, of the antibody-conjugate according to structure (2).

In a second aspect, the invention concerns a process for preparing the antibody-conjugate according to the invention, comprising reacting the compound according to general structure (1) with a modified protein comprising a reactive moiety F which is capable of reacting with Q in a conjugation reaction. In this reaction, a conjugate according to general structure (2) is formed.

Here below, the compound according to general structure (1) is first defined. The structural features of the compound according to general structure (1) also apply to the antibody-conjugate according to structure (2), except for reactive moiety Q in the compound, which is transformed into connecting group Z upon reaction of the compound according to general structure (1) with an antibody comprising reactive moiety F.

Compound According to General Structure (1)
The compound has general structure (1):

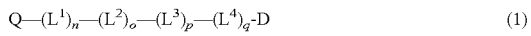

wherein:
Q is a reactive moiety;
D is selected from the group consisting of taxanes, anthracyclines, camptothecins, epothilones, mytomycins, combretastatins, vinca alkaloids, maytansinoids, enediynes such as calicheamicins, duocarmycins, tubulysins, amatoxins, dolastatins and auristatins, pyrrolobenzodiazepine dimers, indolino-benzodiazepine dimers, radioisotopes, therapeutic proteins and peptides (or fragments thereof), kinase inhibitors, MEK inhibitors, KSP inhibitors, and analogues or prodrugs thereof;
$L^1$, $L^2$, $L^3$ and $L^4$ are linkers that together link Q to D as further defined here below;
n, o, p and q are individually 0 or 1, provided that n+o+p+q=1, 2, 3 or 4.

Reactive Moiety Q

The compound according to general structure (1) comprises a reactive moiety Q. In the context of the present invention, the term "reactive moiety" may refer to a chemical moiety that comprises a functional group, but also to a functional group itself. For example, a cyclooctynyl group is a reactive group comprising a functional group, namely a C—C triple bond. Similarly, an N-maleimidyl group is a reactive group, comprising a C=C double bond as a functional group. However, a functional group, for example an azido functional group, a thiol functional group or an alkynyl functional group, may herein also be referred to as a reactive moiety.

In order to be reactive in the process according to the invention, reactive Q should be capable of reacting with a functional group F present on an antibody. In other words, reactive moiety Q is complementary to functional group F present in an antibody. Herein, a reactive group is denoted as "complementary" to a functional group when said reactive group reacts with said functional group selectively, optionally in the presence of other functional groups. Complementary reactive and functional groups are known to a person skilled in the art, and are described in more detail below. As such, the compound according to general structure (1) is conveniently used in a conjugation reaction, wherein a chemical reaction between Q and F takes place, thereby forming an antibody-conjugate comprising a covalent connection between payload D and the antibody.

In a preferred embodiment, reactive moiety Q is selected from the group consisting of, optionally substituted, N-maleimidyl groups, ester groups, carbonate groups, protected thiol groups, alkenyl groups, alkynyl groups, tetrazinyl groups, azido groups, phosphine groups, nitrile oxide groups, nitrone groups, nitrile imine groups, diazo groups, ketone groups, (O-alkyl)hydroxylamino groups, hydrazine groups, allenamide groups, triazine groups. In an especially preferred embodiment, reactive moiety Q is an N-maleimidyl group, an azide group or an alkynyl group, most preferably reactive moiety Q is an alkynyl group. In case Q is an alkynyl group, it is preferred that Q is selected from terminal alkyne groups, (hetero)cycloalkynyl groups and bicyclo[6.1.0]non-4-yn-9-yl] groups.

In a preferred embodiment, Q comprises or is an N-maleimidyl group, preferably Q is a N-maleimidyl group. In case Q is an N-maleimidyl group, Q is preferably unsubstituted. Q is thus preferably according to structure (Q1), as shown below.

In another preferred embodiment, Q comprises or is an ester group, preferably Q is an ester group. In case Q is an ester group, it is preferred that the ester group is an activated ester group. Activated ester groups are known to the person skilled in the art. An activated ester group is herein defined as an ester group comprising a leaving group, wherein the carbonyl group of the ester is bonded to the leaving group. Leaving groups are known to the person skilled in the art. It is further preferred that the activated ester is according to structure (Q2), as shown below, wherein $R^{23}$ is selected from the group consisting of —N-succinimidyl (NHS), —N-sulfo-succinimidyl (sulfo-NHS), -(4-nitrophenyl), -pentafluorophenyl or -tetrafluorophenyl (TFP).

In another preferred embodiment, Q comprises or is a carbonate group, preferably Q is a carbamate group. In case Q is a carbonate group, it is preferred that the carbonate group is an activated carbonate group. Activated carbonate groups are known to a person skilled in the art. An activated carbonate group is herein defined as a carbonate group comprising a leaving group, wherein the carbonate carbonyl group is bonded to the leaving group. It is further preferred that the carbonate group is according to structure (Q3), as shown below, wherein $R^{24}$ is selected from the group consisting of —N-succinimidyl, —N-sulfo-succinimidyl, -(4-nitrophenyl), -pentafluorophenyl or -tetrafluorophenyl.

In another preferred embodiment, Q comprises or is a protected thiol group, preferably Q is a protected thiol group. A thiol group may also be referred to as a mercapto group. A protected thiol group is known in the art and is preferably according to structure (Q5), (Q6) or (Q7) as shown below, wherein $R^{25}$ or $R^{26}$ is an, optionally substituted, $C_1$-$C_{12}$ alkyl group or a $C_2$-$C_{12}$ (hetero)aryl group, $X^3$ is O or S and $R^{26}$ is an, optionally substituted, $C_1$-$C_{12}$ alkyl group. More preferably, $R^{25}$ or $R^{26}$ is an, optionally substituted, $C_1$-$C_6$ alkyl group or a $C_2$-$C_6$ (hetero)aryl group, and even more preferably $R^{25}$ or $R^{26}$ is methyl, ethyl, n-propyl, i-propyl, n-butyl, s-butyl, t-butyl or phenyl. Even more preferably, $R^{25}$ or $R^{26}$ is methyl or phenyl, most preferably methyl.

In another preferred embodiment, Q comprises or is an alkenyl group, including cycloalkenyl groups, preferably Q is an alkenyl group. The alkenyl group may be linear or branched, and is optionally substituted. The alkenyl group may be a terminal or an internal alkenyl group. The alkenyl group may comprise more than one C=C double bond, and preferably comprises one or two C=C double bonds. When the alkenyl group is a dienyl group, it is further preferred that the two C—C double bonds are separated by one C—C single bond (i.e. it is preferred that the dienyl group is a conjugated dienyl group). Preferably said alkenyl group is a $C_2$-$C_{24}$ alkenyl group, more preferably a $C_2$-$C_{12}$ alkenyl group, and even more preferably a $C_2$-$C_6$ alkenyl group. It is further preferred that the alkenyl group is a terminal alkenyl group. More preferably, the alkenyl group is according to structure (Q8) as shown below, wherein I is an integer in the range of 0 to 10, preferably in the range of 0 to 6, and p is an integer in the range of 0 to 10, preferably 0 to 6. More preferably, I is 0, 1, 2, 3 or 4, more preferably I is 0, 1 or 2 and most preferably I is 0 or 1. More preferably, p is 0, 1, 2, 3 or 4, more preferably p is 0, 1 or 2 and most preferably p is 0 or 1. It is particularly preferred that p is 0 and I is 0 or 1, or that p is 1 and I is 0 or 1.

A particularly preferred alkenyl group is a cycloalkenyl group, including heterocycloalkenyl groups, wherein the cycloalkenyl group is optionally substituted. Preferably said cycloalkenyl group is a $C_3$-$C_{24}$ cycloalkenyl group, more preferably a $C_3$-$C_{12}$ cycloalkenyl group, and even more preferably a $C_3$-$C_{24}$ cycloalkenyl group. In a preferred embodiment, the cycloalkenyl group is a trans-cycloalkenyl group, more preferably a trans-cyclooctenyl group (also referred to as a TCO group) and most preferably a trans-cyclooctenyl group according to structure (Q9) or (Q10) as shown below. In another preferred embodiment, the cycloalkenyl group is a cyclopropenyl group, wherein the cyclopropenyl group is optionally substituted. In another preferred embodiment, the cycloalkenyl group is a norbornenyl group, an oxanorbornenyl group, a norbornadienyl group or an oxanorbornadienyl group, wherein the norbornenyl group, oxanorbornenyl group, norbornadienyl group or an oxanorbornadienyl group is optionally substituted. In a further preferred embodiment, the cycloalkenyl group is according to structure (Q11), (Q12), (Q13) or (Q14) as shown below, wherein $X^4$ is $CH_2$ or O, $R^{27}$ is independently selected from the group consisting of hydrogen, a linear or branched $C_1$-$C_{12}$ alkyl group or a $C_4$-$C_{12}$ (hetero) aryl group, and $R^{14}$ is selected from the group consisting of hydrogen and fluorinated hydrocarbons. Preferably, $R^{27}$ is independently hydrogen or a $C_1$-$C_6$ alkyl group, more preferably $R^{27}$ is independently hydrogen or a $C_1$-$C_4$ alkyl group. Even more preferably $R^{27}$ is independently hydrogen or methyl, ethyl, n-propyl, i-propyl, n-butyl, s-butyl or t-butyl. Yet even more preferably $R^{27}$ is independently hydrogen or methyl. In a further preferred embodiment, $R^{14}$ is selected from the group of hydrogen and —$CF_3$, —$C_2F_5$, —$C_3F_7$ and —$C_4F_9$, more preferably hydrogen and —$CF_3$. In a further preferred embodiment, the cycloalkenyl group is according to structure (Q11), wherein one $R^{27}$ is hydrogen and the other $R^{27}$ is a methyl group. In another further preferred embodiment, the cycloalkenyl group is according to structure (Q12), wherein both $R^{27}$ are hydrogen. In these embodiments it is further preferred that I is 0 or 1. In another further preferred embodiment, the cycloalkenyl group is a norbornenyl ($X^4$ is $CH_2$) or an oxanorbornenyl ($X^4$ is O) group according to structure (Q13), or a norbornadienyl ($X^4$ is $CH_2$) or an oxanorbornadienyl ($X^4$ is O) group according to structure (Q14), wherein $R^{27}$ is hydrogen and $R^{14}$ is hydrogen or —$CF_3$, preferably —$CF_3$.

In another preferred embodiment, Q comprises or is an alkynyl group, including cycloalkynyl groups, preferably Q comprises an alkynyl group. The alkynyl group may be linear or branched, and is optionally substituted. The alkynyl group may be a terminal or an internal alkynyl group. Preferably said alkynyl group is a $C_2$-$C_{24}$ alkynyl group, more preferably a $C_2$-$C_{12}$ alkynyl group, and even more preferably a $C_2$-$C_6$ alkynyl group. It is further preferred that the alkynyl group is a terminal alkynyl group. More preferably, the alkynyl group is according to structure (Q15) as shown below, wherein I is an integer in the range of 0 to 10, preferably in the range of 0 to 6. More preferably, I is 0, 1, 2, 3 or 4, more preferably I is 0, 1 or 2 and most preferably I is 0 or 1.

A particularly preferred alkynyl group is a cycloalkynyl group, including hetero cycloalkynyl group, cycloalkenyl group is optionally substituted. Preferably, the (hetero)cycloalkynyl group is a (hetero)cyclooctynyl group, i.e. a heterocyclooctynyl group or a cyclooctynyl group, wherein the (hetero)cyclooctynyl group is optionally substituted. Preferably, Q comprises a (hetero)cyclooctyne moiety according to structure (Q4) below. Herein, the alkynes and (hetero)cycloakynes may optionally be substituted. In a further preferred embodiment, the (hetero)cyclooctynyl group is according to structure (Q36) and defined further below. Preferred examples of the (hetero)cyclooctynyl group include structure (Q16), also referred to as a DIBO group, (Q17), also referred to as a DIBAC group, or (Q18), also referred to as a BARAC group, (Q19), also referred to as a COMBO group, and (Q20), also referred to as a BCN group, all as shown below, wherein $X^5$ is O or N $R^{27}$, and preferred embodiments of $R^{27}$ are as defined above. The aromatic rings in (Q16) are optionally O-sulfonylated at one or more positions, whereas the rings of (Q17) and (Q18) may be halogenated at one or more positions. A particularly preferred cycloalkynyl group is a bicyclo[6.1.0]non-4-yn-9-yl] group (BCN group), which is optionally substituted. Preferably, the bicyclo[6.1.0]non-4-yn-9-yl] group is according to formula (Q20) as shown below, wherein V is $-(CH_2)_I$ and I is an integer in the range of 0 to 10, preferably in the range of 0 to 6. More preferably, I is 0, 1, 2, 3 or 4, more preferably I is 0, 1 or 2 and most preferably I is 0 or 1. In the context of group (Q20), I is most preferably 1.

In another preferred embodiment, Q comprises or is a conjugated (hetero)diene group, preferably Q is a conjugated (hetero)diene group capable of reacting in a Diels-Alder reaction. Preferred (hetero)diene groups include optionally substituted tetrazinyl groups, optionally substituted 1,2-quinone groups and optionally substituted triazine groups. More preferably, said tetrazinyl group is according to structure (Q21), as shown below, wherein $R^{27}$ is selected from the group consisting of hydrogen, a linear or branched $C_1$-$C_{12}$ alkyl group or a $C_4$-$C_{12}$ (hetero)aryl group. Preferably, $R^{27}$ is hydrogen, a $C_1$-$C_6$ alkyl group or a $C_4$-$C_{10}$ (hetero)aryl group, more preferably $R^{27}$ is hydrogen, a $C_1$-$C_4$ alkyl group or a $C_4$-$C_6$ (hetero)aryl group. Even more preferably $R^{27}$ is hydrogen, methyl, ethyl, n-propyl, i-propyl, n-butyl, s-butyl, t-butyl or pyridyl. Yet even more preferably $R^{27}$ is hydrogen, methyl or pyridyl. More preferably, said 1,2-quinone group is according to structure (Q22) or (Q23). Said triazine group may be any regioisomer. More preferably, said triazine group is a 1,2,3-triazine group or a 1,2,4-triazine group, which may be attached via any possible location, such as indicated in structure (Q24). The 1,2,4-triazine is most preferred as triazine group.

In another preferred embodiment, Q comprises or is an azido group, preferably Q is an azido group. Preferably, the azide group is according to structure (Q25) as shown below.

In another preferred embodiment, Q is or comprises a phosphine group, preferably Q is a phosphine group that is suitable to undergo a Staudinger ligation reaction. The phosphine group is optionally substituted, preferably the phosphine group is a triarylphosphine group, more preferably the phosphine group is according to structure (Q26) as shown below, wherein $R^{28}$ is hydrogen or a (thio)ester group. When $R^{28}$ is a (thio)ester group, it is preferred that $R^{28}$ is $-C(O)-X^3-R^{13}$, wherein $X^3$ is O or S and $R^{13}$ is a $C_1$-$C_{12}$ alkyl group. Preferably, $R^{13}$ is a $C_1$-$C_6$ alkyl group, more preferably a $C_1$-$C_4$ alkyl group. Most preferably, $R^{13}$ is a methyl group.

In another preferred embodiment, Q comprises or is a nitrile oxide group, preferably Q is a nitrile oxide group. Preferably, the nitrile oxide group is according to structure (Q27) as shown below.

In another preferred embodiment, Q comprises or is a nitrone group, preferably Q is a nitrone group. Preferably, the nitrone group is according to structure (Q28) as shown below, wherein $R^{29}$ is selected from the group consisting of linear or branched $C_1$-$C_{12}$ alkyl groups and $C_6$-$C_{12}$ aryl groups. Preferably, $R^{29}$ is a $C_1$-$C_6$ alkyl group, more preferably $R^{29}$ is a $C_1$-$C_4$ alkyl group. Even more preferably $R^{29}$ is methyl, ethyl, n-propyl, i-propyl, n-butyl, s-butyl or t-butyl. Yet even more preferably $R^{29}$ is methyl.

In another preferred embodiment, Q comprises or is a nitrile imine group, preferably Q is a nitrile imine group. Preferably, the nitrile imine group is according to structure (Q29) or (Q30) as shown below, wherein $R^{30}$ is selected from the group consisting of linear or branched $C_1$-$C_{12}$ alkyl groups and $C_6$-$C_{12}$ aryl groups. Preferably, $R^{30}$ is a $C_1$-$C_6$ alkyl group, more preferably $R^{30}$ is a $C_1$-$C_4$ alkyl group. Even more preferably $R^{30}$ is methyl, ethyl, n-propyl, i-propyl, n-butyl, s-butyl or t-butyl. Yet even more preferably $R^{30}$ is methyl.

In another preferred embodiment, Q comprises or is a diazo group, preferably Q is a diazo group. Preferably, the diazo group is according to structure (Q31) as shown below, wherein $R^{33}$ is selected from the group consisting of hydrogen or a carbonyl derivative. More preferably, $R^{33}$ is hydrogen.

In another preferred embodiment, Q comprises or is a ketone group, preferably Q is a ketone group. Preferably, the ketone group is according to structure (Q32) as shown below, wherein $R^{34}$ is selected from the group consisting of linear or branched $C_1$-$C_{12}$ alkyl groups and $C_6$-$C_{12}$ aryl groups. Preferably, $R^{34}$ is a $C_1$-$C_6$ alkyl group, more preferably $R^{34}$ is a $C_1$-$C_4$ alkyl group. Even more preferably $R^{34}$ is methyl, ethyl, n-propyl, i-propyl, n-butyl, s-butyl or t-butyl. Yet even more preferably $R^{34}$ is methyl.

In another preferred embodiment, Q comprises or is an (O-alkyl)hydroxylamino group, preferably Q is an (O-alkyl)hydroxylamino group. Preferably, the (O-alkyl)hydroxylamino group is according to structure (Q33) as shown below.

In another preferred embodiment, Q comprises or is a hydrazine group, preferably Q is a hydrazine group. Preferably, the hydrazine group is according to structure (Q34) as shown below.

In another preferred embodiment, Q comprises or is an allenamide group, preferably Q is an allenamide group. Preferably, the allenamide group is according to structure (Q35).

(Q1)

(Q2)

(Q3)

(Q4)

(Q5)

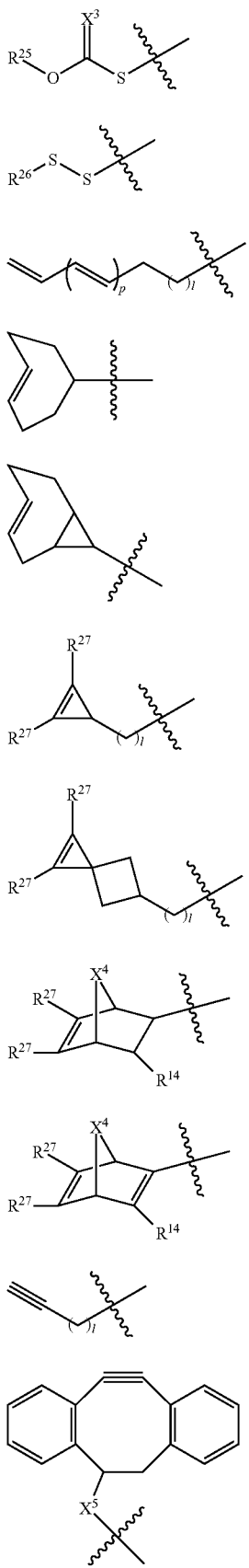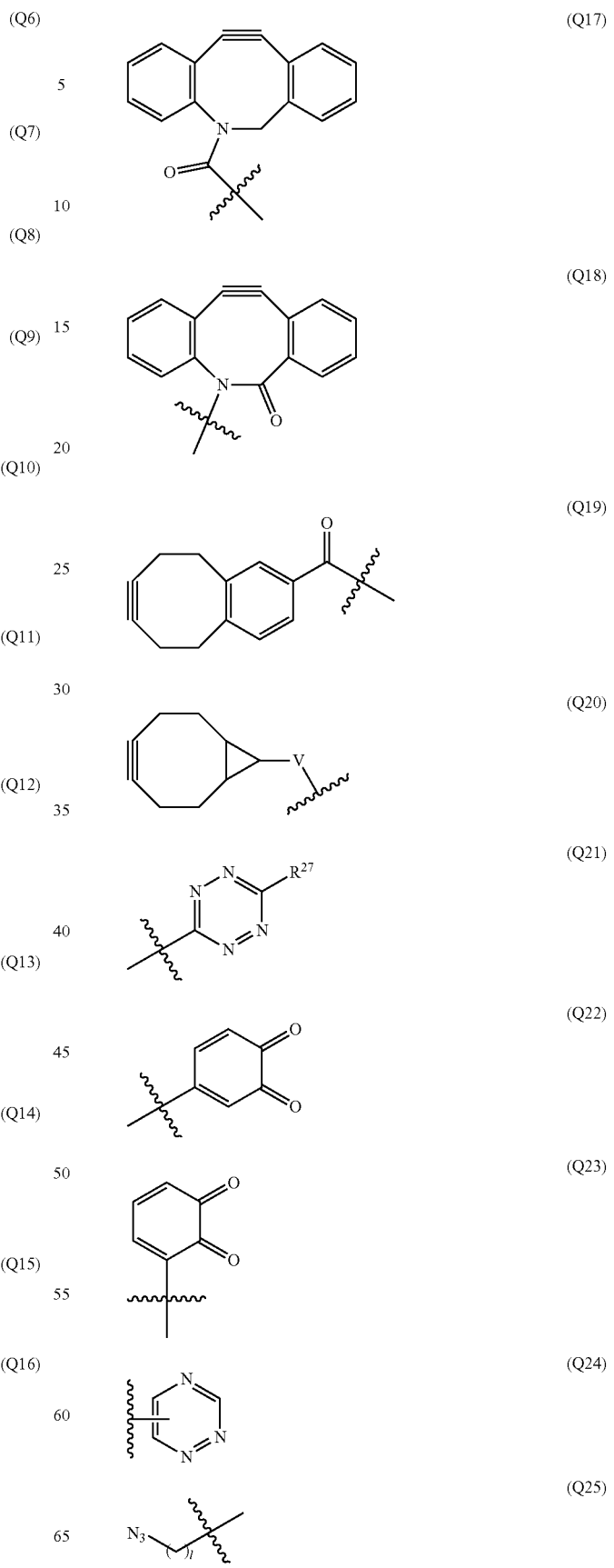

-continued

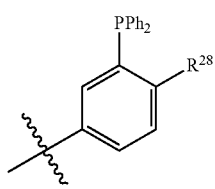
(Q26)

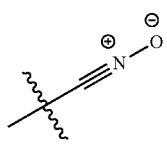
(Q27)

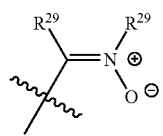
(Q28)

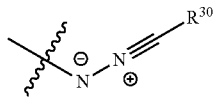
(Q29)

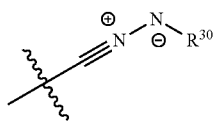
(Q30)

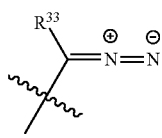
(Q31)

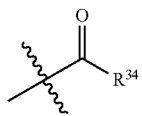
(Q32)

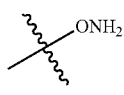
(Q33)

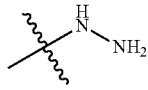
(Q34)

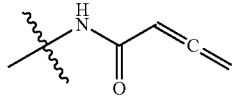
(Q35)

Herein, the aromatic rings in (Q16) are optionally O-sulfonylated at one or more positions, whereas the rings of (Q17) and (Q18) may be halogenated at one or more positions.

In the compound according to general structure (1), Q is capable of reacting with a reactive group F that is present on a biomolecule. Complementary reactive groups F for reactive group Q are known to a person skilled in the art, and are described in more detail below. Some representative examples of reaction between F and Q and their corresponding products (connecting group Z) are depicted in FIG. 1.

In one embodiment, Q is capable of undergoing a click reaction, which may also be referred to as cycloaddition. In an especially preferred embodiment, Q is a click probe. Click probes are herein defined as moieties that comprise a reactive group that is capable of undergoing a click reaction, defined herein as a (2+3) or (2+4) cycloaddition between two functional groups, thereby forming a stable covalent bond, that show high mutual reactivity but at the same time low reactivity for natural biomolecular functionality, such as those present in proteins, nucleic acids, glycans and lipids. Moreover, a click reaction as defined herein can be performed in (nearly) every solvent of choice, including water (and buffered systems thereof), DMSO, DMA, DMF and propylene glycol. Suitable reactive groups include strained cycloalkyne groups, terminal alkyne groups, azido groups, tetrazine groups and strained cycloalkene groups.

Preferred click probes Q are selected from the group consisting of structures (Q1), (Q4), (Q8)-(Q25), (Q27)-(Q31) and (Q35), more preferably from the group consisting of structures (Q1), (Q4), (Q8)-(Q21) and (Q25), most preferably from the group consisting of structures (Q1), (Q4), (Q15)-(Q18), (Q20) and (Q25).

Preferred click reaction in the context of the present invention include Diels-Alder reactions and 1,3-dipolar cycloadditions, preferably the 1,3-dipolar cycloaddition. According to this embodiment, the reactive group Q is selected from groups reactive in a cycloaddition reaction. Herein, reactive groups Q and F are complementary, i.e. they are capable of reacting with each other in a cycloaddition.

For a Diels-Alder reaction, Q is a diene or a dienophile. As appreciated by the skilled person, the term "diene" in the context of the Diels-Alder reaction refers to 1,3-(hetero) dienes, and includes conjugated dienes ($R_2C=CR—CR=CR_2$), imines (e.g. $R_2C=CR—N=CR_2$ or $R_2C=CR—CR=NR$, $R_2C=N—N=CR_2$) and carbonyls (e.g. $R_2C=CR—CR=O$ or $O=CR—CR=O$). Hetero-Diels-Alder reactions with N- and O-containing dienes are known in the art. Any diene known in the art to be suitable for Diels-Alder reactions may be used as reactive group Q. Preferred dienes include tetrazines as described above, 1,2-quinones as described above and triazines as described above. Although any dienophile known in the art to be suitable for Diels-Alder reactions may be used as reactive group Q, the dienophile is preferably an alkene or alkyne group as described above, most preferably an alkyne group. For conjugation via a Diels-Alder reaction, it is preferred that Q is a dienophile (and F is a diene), more preferably Q is or comprises an alkynyl group.

For a 1,3-dipolar cycloaddition, Q is a 1,3-dipole or a dipolarophile. Any 1,3-dipole known in the art to be suitable for 1,3-dipolar cycloadditions may be used as reactive group Q. Preferred 1,3-dipoles include azido groups, nitrone groups, nitrile oxide groups, nitrile imine groups and diazo groups. Although any dipolarophile known in the art to be suitable for 1,3-dipolar cycloadditions may be used as reactive groups Q, the dipolarophile is preferably an alkene or alkyne group, most preferably an alkyne group. For conjugation via a 1,3-dipolar cycloaddition, it is preferred that Q is a dipolarophile (and F is a 1,3-dipole), more preferably Q is or comprises an alkynyl group.

In a preferred embodiment, Q is selected from dipolarophiles and dienophiles. Preferably, Q is an alkene or an alkyne group. In an especially preferred embodiment, Q comprises an alkyne group, preferably selected from the alkynyl group as described above, the cycloalkenyl group as described above, the (hetero)cycloalkynyl group as described above and a bicyclo[6.1.0]non-4-yn-9-yl] group, more preferably Q is selected from the formulae (Q15), (Q16), (Q17), (Q18), (Q20) and (Q19), more preferably selected from the formulae (Q16), (Q17), (Q18), (Q20) and (Q19). Most preferably, Q is a bicyclo[6.1.0]non-4-yn-9-yl] group, preferably of formula (Q20). These groups are known to be highly effective in the conjugation with azido-functionalized antibodies as described herein.

In an especially preferred embodiment, reactive group Q comprises an alkynyl group and is according to structure (Q36):

(Q36)

Herein:
$R^{15}$ is independently selected from the group consisting of hydrogen, halogen, —$OR^{16}$, —$NO_2$, —CN, —$S(O)_2 R^{16}$, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^{15}$ may be linked together to form an optionally substituted annulated cycloalkyl or an optionally substituted annulated (hetero)arene substituent, and wherein $R^{16}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;
$X^{10}$ is $C(R^{31})_2$, O, S or $NR^{31}$, wherein each $R^{31}$ is individually is $R^{15}$ or —$(L^1)_n$—$(L^2)_o$—$(L^3)_p$—$(L^4)_q$-D;
u is 0, 1, 2, 3, 4 or 5;
u' is 0, 1, 2, 3, 4 or 5;
wherein u+u'=5;
v=8, 9 or 10.

Preferred embodiments of the reactive group according to structure (Q36) are reactive groups according to structure (Q37), (Q16), (Q17), (Q18), (Q19) and (Q20).

In an especially preferred embodiment, reactive group Q comprises an alkynyl group and is according to structure (Q37):

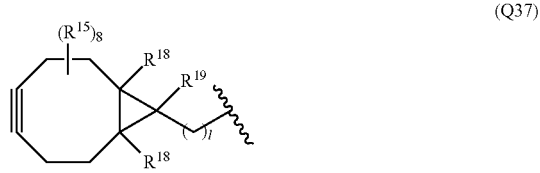

(Q37)

Herein:
$R^{15}$ is independently selected from the group consisting of hydrogen, halogen, —$OR^{16}$, —$NO_2$, —CN, —$S(O)_2 R^{16}$, $C_1$-$C_{24}$ alkyl groups, $C_5$-$C_{24}$ (hetero)aryl groups, $C_7$-$C_{24}$ alkyl(hetero)aryl groups and $C_7$-$C_{24}$ (hetero)arylalkyl groups and wherein the alkyl groups, (hetero)aryl groups, alkyl(hetero)aryl groups and (hetero)arylalkyl groups are optionally substituted, wherein two substituents $R^{15}$ may be linked together to form an optionally substituted annulated cycloalkyl or an optionally substituted annulated (hetero)arene substituent, and wherein $R^{16}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;
$R^{18}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups;
$R^{19}$ is selected from the group consisting of hydrogen, —$(L^1)_n$—$(L^2)_o$—$(L^3)_p$—$(L^4)_q$-D; halogen, $C_1$-$C_{24}$ alkyl groups, $C_6$-$C_{24}$ (hetero)aryl groups, $C_7$-$C_{24}$ alkyl (hetero)aryl groups and $C_7$-$C_{24}$ (hetero)arylalkyl groups, the alkyl groups optionally being interrupted by one of more hetero-atoms selected from the group consisting of O, N and S, wherein the alkyl groups, (hetero)aryl groups, alkyl(hetero)aryl groups and (hetero)arylalkyl groups are independently optionally substituted; and
I is an integer in the range 0 to 10.

In a preferred embodiment of the reactive group according to structure (Q37), $R^{15}$ is independently selected from the group consisting of hydrogen, halogen, —$OR^{16}$, $C_1$-$C_6$ alkyl groups, $C_5$-$C_6$ (hetero)aryl groups, wherein $R^{16}$ is hydrogen or $C_1$-$C_6$ alkyl, more preferably $R^{15}$ is independently selected from the group consisting of hydrogen and $C_1$-$C_6$ alkyl, most preferably all $R^{15}$ are H. In a preferred embodiment of the reactive group according to structure (Q37), $R^{18}$ is independently selected from the group consisting of hydrogen, $C_1$-$C_6$ alkyl groups, most preferably both $R^{18}$ are H. In a preferred embodiment of the reactive group according to structure (Q37), $R^{19}$ is H. In a preferred embodiment of the reactive group according to structure (Q37), I is 0 or 1, more preferably I is 1. An especially preferred embodiment of the reactive group according to structure (Q37) is the reactive group according to structure (Q20).

Payload D

D represents the target molecule D that is or is to be connected to the antibody, which is also referred to in the art as the payload. D is selected from the group consisting of taxanes, anthracyclines, camptothecins, epothilones, mytomycins, combretastatins, vinca alkaloids, maytansinoids, enediynes such as calicheamicins, duocarmycins, tubulysins, amatoxins, dolastatins and auristatins, pyrrolobenzodiazepine dimers, indolino-benzodiazepine dimers, radioisotopes, therapeutic proteins and peptides (or fragments thereof), kinase inhibitors, MEK inhibitors, KSP inhibitors, and analogues or prodrugs thereof. Alternatively, D is defined as an pharmaceutically active substance, such as an anti-cancer agent, preferably a cytotoxin. In an especially preferred embodiment, D is a cytotoxin selected from auristatins, amatoxins, enediyne antibiotics, SN-38 and bleomycin.

In case D is an auristatin, it is preferred that D is MMAE or MMAF, more preferably D=MMAE. In case D is an amatoxin, it is preferred that D is selected from the group consisting of α-amanitin, β-amanitin, γ-amanitin, ε-amanitin, amanullin, amanullinic acid, amaninamide, amanin and proamanullin, more preferably β-amanitin. In case D is an enediyne-containing cytotoxin, it is preferred that D is selected from the group consisting of calicheamicins, esperamicins, shishijimicins and namenamicins, more preferably calicheamicin.

The compound according to general structure (1) may comprise more than one moiety D. When more than one cytotoxin D is present the cytotoxins D may be the same or different, typically they are the same. In a preferred embodiment, the compound according to general structure (1) contains 1 or 2 occurrences of D, most preferably 2 occurrence of D. Typically, the second occurrence of D is present within $L^1$, which may contain a branching moiety, typically a branching nitrogen atom, that is connected to the second occurrence of D. Preferably, both occurrences of D are connected to the branching moiety via the same linker.

Linkers $L^1$, $L^2$, $L^3$ and $L^4$ are linkers. Linkers (L), also referred to as linking units, are well known in the art. In a preferred embodiment, at least linkers $L^1$ and $L^2$ are present (i.e. n=1; o=1; p=0 or 1; q=0 or 1), more preferably linkers $L^1$, $L^2$ and $L^3$ are present and $L^4$ is either present or not (i.e. n=1; o=1; p=1; q=0 or 1). In one embodiment, linkers $L^1$, $L^2$, $L^3$ and $L^4$ are present (i.e. n=1; o=1; p=1; q=1). In one embodiment, linkers $L^1$, $L^2$ and $L^3$ are present and $L^4$ is not (i.e. n=1; o=1; p=1; q=0).

Linker $L^1$

Linker $L^1$ is either absent (n=0) or present (n=1). Preferably, linker $L^1$ is present and n=1. $L^1$ may for example be selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups, $C_9$-$C_{200}$ arylalkynylene groups. Optionally the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups may be substituted, and optionally said groups may be interrupted by one or more heteroatoms, preferably 1 to 100 heteroatoms, said heteroatoms preferably being selected from the group consisting of O, $S(O)_y$ and $NR^{21}$, wherein y is 0, 1 or 2, preferably y=2, and $R^{21}$ is independently selected from the group consisting of hydrogen, halogen, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups.

$L^1$ may contain (poly)ethylene glycoldiamines (e.g. 1,8-diamino-3,6-dioxaoctane or equivalents comprising longer ethylene glycol chains), (poly)ethylene glycol or (poly)ethylene oxide chains, (poly)propylene glycol or (poly)propylene oxide chains and 1,z-diaminoalkanes wherein z is the number of carbon atoms in the alkane.

In a preferred embodiment, Linker $L^1$ is or comprises a sulfamide group, preferably a sulfamide group according to structure (23):

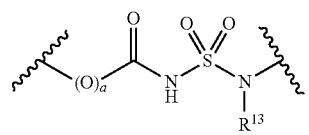

(23)

The wavy lines represent the connection to the remainder of the compound, typically to Q and $L^2$, $L^3$, $L^4$ or D, preferably to Q and $L^2$. Preferably, the $(O)_aC(O)$ moiety is connected to Q and the $NR^{13}$ moiety to $L^2$, $L^3$, $L^4$ or D, preferably to $L^2$.

In structure (23), a=0 or 1, preferably a=1, and $R^{13}$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups optionally substituted and optionally interrupted by one or more heteroatoms selected from O, S and $NR^{14}$ wherein $R^{14}$ is independently selected from the group consisting of hydrogen and $C_1$-$C_4$ alkyl groups, or $R^{13}$ is D connected to N via a spacer moiety, preferably $Sp^2$ as defined below, in one embodiment D is connected to N via —$(B)_e$-$(A)_f$-$(B)_g$—C(O)—.

In a preferred embodiment, $R^{13}$ is hydrogen or a $C_1$-$C_{20}$ alkyl group, more preferably $R^{13}$ is hydrogen or a $C_1$-$C_{16}$ alkyl group, even more preferably $R^{13}$ is hydrogen or a $C_1$-$C_{10}$ alkyl group, wherein the alkyl group is optionally substituted and optionally interrupted by one or more heteroatoms selected from O, S and $NR^{14}$, preferably O, wherein $R^{14}$ is independently selected from the group consisting of hydrogen and $C_1$-$C_4$ alkyl groups. In a preferred embodiment, $R^{13}$ is hydrogen. In another preferred embodiment, $R^{13}$ is a $C_1$-$C_{20}$ alkyl group, more preferably a $C_1$-$C_{16}$ alkyl group, even more preferably a $C_1$-$C_{10}$ alkyl group, wherein the alkyl group is optionally interrupted by one or more O-atoms, and wherein the alkyl group is optionally substituted with an —OH group, preferably a terminal —OH group. In this embodiment it is further preferred that $R^{13}$ is a (poly)ethylene glycol chain comprising a terminal —OH group. In another preferred embodiment, $R^{13}$ is selected from the group consisting of hydrogen, methyl, ethyl, n-propyl, i-propyl, n-butyl, s-butyl and t-butyl, more preferably from the group consisting of hydrogen, methyl, ethyl, n-propyl and i-propyl, and even more preferably from the group consisting of hydrogen, methyl and ethyl. Yet even more preferably, $R^{13}$ is hydrogen or methyl, and most preferably $R^{13}$ is hydrogen.

In a preferred embodiment, $L^1$ is according to structure (24):

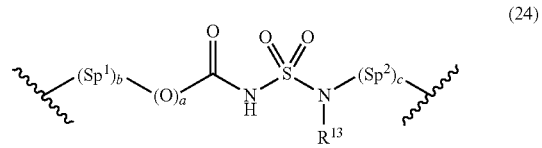

(24)

Herein, a and $R^{13}$ are as defined above, $Sp^1$ and $Sp^2$ are independently spacer moieties and b and c are independently 0 or 1. Preferably, b=0 or 1 and c=1, more preferably b=0 and c=1. In one embodiment, spacers $Sp^1$ and $Sp^2$ are independently selected from the group consisting of linear or branched $C_1$-$C_{200}$ alkylene groups, $C_2$-$C_{200}$ alkenylene groups, $C_2$-$C_{200}$ alkynylene groups, $C_3$-$C_{200}$ cycloalkylene groups, $C_5$-$C_{200}$ cycloalkenylene groups, $C_8$-$C_{200}$ cycloalkynylene groups, $C_7$-$C_{200}$ alkylarylene groups, $C_7$-$C_{200}$ arylalkylene groups, $C_8$-$C_{200}$ arylalkenylene groups and $C_9$-$C_{200}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^{16}$, wherein $R^{16}$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. When the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are interrupted by one or more heteroatoms as defined above, it is preferred that said groups are interrupted by one or more O-atoms, and/or by one or more S—S groups.

More preferably, spacer moieties $Sp^1$ and $Sp^2$, if present, are independently selected from the group consisting of linear or branched $C_1$-$C_{100}$ alkylene groups, $C_2$-$C_{100}$ alkenylene groups, $C_2$—$C_{100}$ alkynylene groups, $C_3$-$C_{100}$ cycloalkylene groups, $C_5$-$C_{100}$ cycloalkenylene groups, $C_8$-$C_{100}$ cycloalkynylene groups, $C_7$-$C_{100}$ alkylarylene groups, $C_7$-$C_{100}$ arylalkylene groups, $C_8$-$C_{100}$ arylalkenylene groups and $C_7$-$C_{100}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^{16}$, wherein $R^{16}$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Even more preferably, spacer moieties $Sp^1$ and $Sp^2$, if present, are independently selected from the group consisting of linear or branched $C_1$-$C_{50}$ alkylene groups, $C_2$-$C_{50}$ alkenylene groups, $C_2$-$C_{50}$ alkynylene groups, $C_3$-$C_{50}$ cycloalkylene groups, $C_2$-$C_{50}$ cycloalkenylene groups, $C_8$-$C_{50}$ cycloalkynylene groups, $C_7$-$C_{50}$ alkylarylene groups, $C_7$-$C_{50}$ arylalkylene groups, $C_8$-$C_{50}$ arylalkenylene groups and $C_9$-$C_{50}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^{16}$, wherein $R^{16}$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Yet even more preferably, spacer moieties $Sp^1$ and $Sp^2$, if present, are independently selected from the group consisting of linear or branched $C_1$-$C_{20}$ alkylene groups, $C_2$-$C_{20}$ alkenylene groups, $C_2$-$C_{20}$ alkynylene groups, $C_3$-$C_{20}$ cycloalkylene groups, $C_5$-$C_{20}$ cycloalkenylene groups, $C_8$-$C_{20}$ cycloalkynylene groups, $C_7$-$C_{20}$ alkylarylene groups, $C_7$-$C_{20}$ arylalkylene groups, $C_8$-$C_{20}$ arylalkenylene groups and $C_9$-$C_{20}$ arylalkynylene groups, the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^{16}$, wherein $R^{16}$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

In these preferred embodiments it is further preferred that the alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups are unsubstituted and optionally interrupted by one or more heteroatoms selected from the group of O, S and $NR^{16}$, preferably O, wherein $R^{16}$ is independently selected from the group consisting of hydrogen and $C_1$-$C_4$ alkyl groups, preferably hydrogen or methyl.

Most preferably, spacer moieties $Sp^1$ and $Sp^2$, if present, are independently selected from the group consisting of linear or branched $C_1$-$C_{20}$ alkylene groups, the alkylene groups being optionally substituted and optionally interrupted by one or more heteroatoms selected from the group of O, S and $NR^{16}$, wherein $R^{16}$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted. In this embodiment, it is further preferred that the alkylene groups are unsubstituted and optionally interrupted by one or more heteroatoms selected from the group of O, S and $NR^{16}$, preferably O and/or S—S, wherein $R^{16}$ is independently selected from the group consisting of hydrogen and $C_1$-$C_4$ alkyl groups, preferably hydrogen or methyl.

Preferred spacer moieties $Sp^1$ and $Sp^2$ thus include —$(CH_2)_r$—, —$(CH_2CH_2)_r$—, —$(CH_2CH_2O)_r$—, —$(OCH_2CH_2)_r$—, —$(CH_2CH_2O)_rCH_2CH_2$—, —$CH_2CH_2(OCH_2CH_2)_r$—, —$(CH_2CH_2CH_2O)_r$—, —$(OCH_2CH_2CH_2)_r$—, —$(CH_2CH_2CH_2O)_rCH_2CH_2CH_2$— and —$CH_2CH_2CH_2(OCH_2CH_2CH_2)_r$—, wherein r is an integer in the range of 1 to 50, preferably in the range of 1 to 40, more preferably in the range of 1 to 30, even more preferably in the range of 1 to 20 and yet even more preferably in the range of 1 to 15. More preferably n is 1, 2, 3, 4, 5, 6, 7, 8, 9 or 10, more preferably 1, 2, 3, 4, 5, 6, 7 or 8, even more preferably 1, 2, 3, 4, 5 or 6, yet even more preferably 1, 2, 3 or 4.

Alternatively, preferred linkers $L^1$ may be represented by —$(W)_k$-$(A)_d$-$(B)_e$-$(A)_f$-$(C(O))_g$—, wherein:
d=0 or 1, preferably d=1;
e=an integer in the range 0-10, preferably e=0, 1, 2, 3, 4, 5 or 6, preferably an integer in the range 1-10, most preferably e=1, 2, 3 or 4;
f=0 or 1, preferably f=0;
wherein d+e+f is at least 1, preferably in the range 1-5; and preferably wherein d+f is at least 1, preferably d+f=1.
g=0 or 1, preferably g=1;
k=0 or 1, preferably k=1;
A is a sulfamide group according to structure (23);
B is a —$CH_2$—$CH_2$—O— or a —O—$CH_2$—$CH_2$— moiety, or $(B)_e$ is a —$(CH_2$—$CH_2$—O)_{e1}$—$CH_2$—$CH_2$-moiety, wherein e1 is defined the same way as e;
W is —OC(O)—, —C(O)O—, —C(O)NH—, —NHC(O)—, —OC(O)NH—, —NHC(O)O—, —C(O)$(CH_2)_m$ C(O)—, —C(O)$(CH_2)_m$C(O)NH— or -(4-Ph)$CH_2$NHC(O)$(CH_2)_m$C(O)NH—, preferably wherein W is —OC(O)NH—, —C(O)$(CH_2)_m$C(O)NH— or —C(O)NH—, and wherein m is an integer in the range 0-10, preferably m=0, 1, 2, 3, 4, 5 or 6, most preferably m=2 or 3;
preferably wherein $L^1$ is connected to Q via $(W)_k$ and to $L^2$, $L^3$, $L^4$ or D, preferably to $L^2$, via $(C(O))_g$, preferably via C(O).

In the context of the present embodiment, the wavy lines in structure (23) represent the connection to the adjacent groups such as $(W)_k$, $(B)_e$ and $(C(O))_g$. It is preferred that A is according to structure (23), wherein a=1 and R$^{13}$=H or a C$_1$-C$_{20}$ alkyl group, more preferably R$^{13}$=H or methyl, most preferably R$^{13}$=H.

Preferred linkers L$^1$ have structure —(W)$_k$-(A)$_d$-(B)$_e$-(A)$_f$-(C(O))$_g$—, wherein:
(a) k=0; d=1; g=1; f=0; B=—CH$_2$—CH$_2$—O—; e=1, 2, 3 or 4, preferably e=2.
(b) k=1; W=—C(O)(CH$_2$)$_m$C(O)NH—; m=2; d=0; (B)$_e$=—(CH$_2$—CH$_2$—O)$_{e1}$—CH$_2$—CH$_2$—; f=0; g=1; e1=1, 2, 3 or 4, preferably e=1.
(c) k=1; W=—OC(O)NH—; d=0; B=—CH$_2$—CH$_2$—O—; g=1; f=0; e=1, 2, 3 or 4, preferably e=2.
(d) k=1; W=—C(O)(CH$_2$)$_m$C(O)NH—; m=2; d=0; (B)$_e$=—(CH$_2$—CH$_2$—O)$_{e1}$—CH$_2$—CH$_2$—; f=0; g=1; e1=1, 2, 3 or 4, preferably e1=4.
(e) k=1; W=—OC(O)NH—; d=0; (B)$_e$=—(CH$_2$—CH$_2$—O)$_{e1}$—CH$_2$—CH$_2$—; g=1; f=0; e1=1, 2, 3 or 4, preferably e1=4.
(f) k=1; W=—(4-Ph)CH$_2$NHC(O)(CH$_2$)$_m$C(O)NH—, m=3; d=0; (B)$_e$=—(CH$_2$—CH$_2$—O)$_{e1}$—CH$_2$—CH$_2$—; g=1; f=0; e1=1, 2, 3 or 4, preferably e1=4.
(g) k=0; d=0; g=1; f=0; B=—CH$_2$—CH$_2$—O—; e=1, 2, 3 or 4, preferably e=2.
(h) k=1; W=—C(O)NH—; d=0; g=1; f=0; B=—CH$_2$—CH$_2$—O—; e=1, 2, 3 or 4, preferably e=2.

In a preferred embodiment, linker L$^1$ comprises a branching nitrogen atom, which is located in the backbone between Q and (L$^2$)$_o$ and which contains a further moiety D as substituent, which is preferably linked to the branching nitrogen atom via a linker. An example of a branching nitrogen atom is the nitrogen atom NR$^{13}$ in structure (23), wherein R$^{13}$ is connected to a second occurrence of D via a spacer moiety. Alternatively, a branching nitrogen atoms may be located within L$^1$ according to structure —(W)$_k$-(A)$_d$-(B)$_e$-(A)$_f$-(C(O))$_g$—. In one embodiment, L$^1$ is represented by —(W)$_k$-(A)$_d$-(B)$_e$-(A)$_f$-(C(O))$_g$—N*[-(A)$_d$-(B)$_e$-(A)$_f$-(C(O))$_g$-]$_2$, wherein A, B, W, d, e, f, g and k are as defined above and individually selected for each occurrence, and N* is the branching nitrogen atoms, to which two instances of -(A)$_d$-(B)$_e$-(A)$_f$-(C(O))$_g$— are connected. Herein, both (C(O))$_g$ moieties are connected to —(L$^2$)$_o$—(L$^3$)$_p$—(L$^4$)$_q$-D, wherein L$^2$, L$^3$, L$^4$, o, p, q and D are as defined above and are each selected individually. In a preferred embodiment, each of L$^2$, L$^3$, L$^4$, o, p, q and D are the same for both moieties connected to (C(O))$_g$.

Preferred linkers L$^1$ comprising a branching nitrogen atom have structure —(W)$_k$-(A)$_d$-(B)$_e$-(A)$_f$-(C(O))$_g$—N*[-(A)$_{d'}$-(B)$_{e'}$-(A)$_{f'}$-(C(O))$_{g'}$-]$_2$ wherein:
(i) k=d=g=e'=1; f=d'=g'=0; W=—C(O)—; B=B'=—CH$_2$—CH$_2$—O—; A is according to structure (23) with a=0 and R$^{13}$=H; e=1, 2, 3 or 4, preferably e=2.
(j) k=d=g=e'=g'=1; f=d'=0; W=—C(O)—; B=B'=—CH$_2$—CH$_2$—O—; A is according to structure (23) with a=0 and R$^{13}$=H; e=1, 2, 3 or 4, preferably e=2.

Linker L$^2$

Linker L$^2$ is either absent (o=0) or present (o=1). Preferably, linker L$^2$ is present and o=1. Linker L$^2$ is a peptide spacer as known in the art, preferably a dipeptide or tripeptide spacer as known in the art, preferably a dipeptide spacer. Although any dipeptide or tripeptide spacer may be used, preferably linker L$^2$ is selected from Val-Cit, Val-Ala, Val-Lys, Val-Arg, AcLys-Val-Cit, AcLys-Val-Ala, Phe-Cit, Phe-Ala, Phe-Lys, Phe-Arg, Ala-Lys, Leu-Cit, Ile-Cit, Trp-Cit, Ala-Ala-Asn, Phe-Ala-Asn, more preferably Val-Cit, Val-Ala, Val-Lys, Phe-Cit, Phe-Ala, Phe-Lys, Ala-Ala-Asn, more preferably Val-Cit, Val-Ala, Ala-Ala-Asn. In one embodiment, L$^2$=Val-Cit. In one embodiment, L$^2$=Val-Ala. (AcLys=acetyllysine).

In a preferred embodiment, L$^2$ is represented by general structure (27):

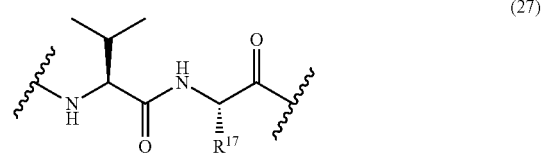

(27)

Herein, R$^{17}$=CH$_3$ (Val) or CH$_2$CH$_2$CH$_2$NHC(O)NH$_2$ (Cit). The wavy lines indicate the connection to (L$^1$)$_n$ and (L$^3$)$_p$, preferably L$^2$ according to structure (27) is connected to (L$^1$)$_n$ via NH and to (L$^3$)$_p$ via C(O).

Linker L$^3$

Linker L$^3$ is either absent (p=0) or present (p=1). Preferably, linker L$^3$ is present and p=1. Linker L$^3$ is a self-cleavable spacer, also referred to as self-immolative spacer. Preferably, L$^3$ is para-aminobenzyloxycarbonyl (PABC) derivative, more preferably a PABC derivative according to structure (25).

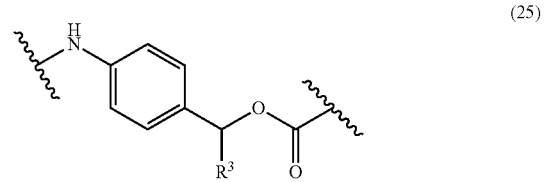

(25)

Herein, the wavy lines indicate the connection to Q, L$^1$ or L$^2$, and to L$^4$ or D. Typically, the PABC derivative is connected via NH to Q, L$^1$ or L$^2$, preferably to L$^2$, and via O to L$^4$ or D.

R$^3$ is H, R$^4$ or C(O)R$^4$, wherein R$^4$ is C$_1$-C$_{24}$ (hetero)alkyl groups, C$_3$-C$_{10}$ (hetero)cycloalkyl groups, C$_2$-C$_{10}$ (hetero)aryl groups, C$_3$-C$_{10}$ alkyl(hetero)aryl groups and C$_3$-C$_{10}$ (hetero)arylalkyl groups, which optionally substituted and optionally interrupted by one or more heteroatoms selected from O, S and NR$^5$ wherein R$^5$ is independently selected from the group consisting of hydrogen and C$_1$-C$_4$ alkyl groups. Preferably, R$^4$ is C$_3$-C$_{10}$ (hetero)cycloalkyl or polyalkylene glycol. The polyalkylene glycol is preferably a polyethylene glycol or a polypropylene glycol, more preferably —(CH$_2$CH$_2$O)$_s$H or —(CH$_2$CH$_2$CH$_2$O)$_s$H. The polyalkylene glycol is most preferably a polyethylene glycol, preferably —(CH$_2$CH$_2$O)$_s$H, wherein s is an integer in the range 1-10, preferably 1-5, most preferably s=1, 2, 3 or 4. More preferably, R$^3$ is H or C(O)R$^4$, wherein R$^4$=4-methylpiperazine or morpholine. Most preferably, R$^3$ is H.

Linker L$^4$

Linker L$^4$ is either absent (q=0) or present (q=1). Preferably, linker L$^4$ is present and q=1. Linker L$^4$ is selected from:
an aminoalkanoic acid spacer according to the structure —NR$^{22}$—(C$_x$-alkylene)-C(O)—, wherein x is an integer in the range 1-20 and R$^{22}$ is H or C$_1$-C$_4$ alkyl;
an ethyleneglycol spacer according to the structure —NR$^{22}$—(CH$_2$—CH$_2$—O)$_{e6}$—(CH$_2$)$_{e7}$—C(O)—, wherein e6 is an integer in the range 1-10, e7 is an integer in the range 1-3 and R$^{22}$ is H or C$_1$-C$_4$ alky; and an diamine spacer according to the structure —$NR^{22}$—($C_x$-alkylene)-$NR^{22}$—, wherein x is an integer in the range 1-10 and $R^{22}$ is H or $C_1$-$C_4$ alkyl.

Linker $L^4$ may be an aminoalkanoic acid spacer, i.e. —$NR^{22}$—($C_x$-alkylene)-C(O)—, wherein x is an integer in the range 1 to 20, preferably 1-10, most preferably 1-6. Herein, the aminoalkanoic acid spacer is typically connected to $L^3$ via the nitrogen atom and to D via the carbonyl moiety. Preferred linkers $L^4$ are selected from 6-aminohexanoic acid (Ahx, x=5), β-alanine (x=2) and glycine (Gly, x=1), even more preferably 6-aminohexanoic acid or glycine. In one embodiment, $L^4$=6-aminohexanoic acid. In one embodiment, $L^4$=glycine. Herein, $R^{22}$ is H or $C_1$-$C_4$ alkyl, preferably $R^{22}$ is H or methyl, most preferably $R^{22}$ is H.

Alternatively, linker $L^4$ may be an ethyleneglycol spacer according to the structure —$NR^{22}$—$(CH_2$—$CH_2$—$O)_{e6}$—$(CH_2)_{e7}$—C(O)—, wherein e6 is an integer in the range 1-10, preferably e6 is in the range 2-6, and e7 is an integer in the range 1-3, preferably e7 is 2. Herein, $R^{22}$ is H or $C_1$-$C_4$ alkyl, preferably $R^{22}$ is H or methyl, most preferably $R^{22}$ is H.

Alternatively, linker $L^4$ may be a diamine spacer according to the structure —$NR^{22}$—($C_x$-alkylene)-$NR^{22}$—, wherein x is an integer in the range 1-10, preferably an integer in the range 2-6, most preferably x=2 or 5. $R^{22}$ is H or $C_1$-$C_4$ alkyl. Herein, $R^{22}$ is H or $C_1$-$C_4$ alkyl, preferably $R^{22}$ is H or methyl, most preferably $R^{22}$ is methyl.

Compounds according to general formula (1) can be prepared by the skilled person using standard organic synthesis techniques, and as exemplified in the examples.

Antibody-Conjugate

In a first aspect, the invention concerns an antibody-conjugate, wherein the compound according to general structure (1) is conjugated to an antibody. In the context of the present invention, the antibody may be modified in order to be capable in reacting with the compound according to the invention. The antibody-conjugate according to the invention is according to general structure (2):

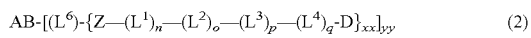

wherein:

AB is an antibody capable of targeting Trop-2-expressing tumours;

$L^1$, $L^2$, $L^3$ and $L^4$ are each individually linkers that together link Z to D;

n, o, p and q are each individually 0 or 1, provided that n+o+p+q=1, 2, 3 or 4;

Z is a connecting group;

$L^6$ is -GlcNAc(Fuc)$_w$-S—$(L^7)_{w'}$—, wherein S is a sugar or a sugar derivative, GlcNAc is N-acetylglucosamine and Fuc is fucose, w is 0 or 1, w' is 0, 1 or 2, and $L^7$ is —N(H)C(O)$CH_2$—, —N(H)C(O)$CF_2$— or —$CH_2$—;

D is selected from the group consisting of taxanes, anthracyclines, camptothecins, epothilones, mytomycins, combretastatins, vinca alkaloids, maytansinoids, enediynes such as calicheamicins, duocarmycins, tubulysins, amatoxins, bleomycins, dolastatins and auristatins, pyrrolobenzodiazepine dimers, indolinobenzodiazepine dimers, radioisotopes, therapeutic proteins and peptides (or fragments thereof), kinase inhibitors, MEK inhibitors, KSP inhibitors, and analogues or prodrugs thereof;

xx is 1 or 2; and yy is 1, 2, 3 or 4.

Herein, $L^1$, $L^2$, $L^3$, $L^4$, D, n, o, p and q are as defined above for the compound according to the invention, albeit with $(L^1)_n$ being connected to Z instead of Q. These structural features remain unchanged when the compound according to the invention reacts with the (modified) antibody to form the conjugate according to the invention. Further, Z is a connecting group that is formed when Q on the compound according to general structure (1) reacts with F on the modified antibody. In a preferred embodiment, the reaction between Q and F is a click reaction, also known as a 1,3-dipolar cycloaddition, in which case Z contains a moiety that is obtained in a click reaction between Q and F, preferably Z contains a triazole.

Antibodies capable of targeting Trop-2-expressing tumours are known to the skilled person. Preferably, the antibody is selected from the group consisting of Huk5-70-2, hRS7, hTINA, AR47A6.4.2, RN926, including humanized or functional analogues thereof, more preferably the antibody is Huk5-70-2 or hRS7, most preferably the antibody is hRS7. The inventors have found that antibody-conjugates with these antibodies are exceptionally suitable for targeting Trop-2 expressing cells.

$L^6$ is a linker that links AB to Z, and is represented by -GlcNAc(Fuc)$_w$-S—$(L^7)_{w'}$, wherein S is a sugar or a sugar derivative, GlcNAc is N-acetylglucosamine and Fuc is fucose, w is 0 or 1, w' is 0, 1 or 2. The GlcNAc(Fuc)$_w$ moiety is preferably a core-GlcNAc(Fuc)$_w$ moiety, meaning that GlcNAc is the core-sugar moiety in the glycan of a glycoprotein that is directly attached to the peptide chain of the glycoprotein.

$L^7$ is a linker that links S with Z. $L^7$ may be present (w'=1 or 2) or absent (w'=0). Each moiety Z may be connected to S via a linker $L^7$, thus in one embodiment w'=0 or xx. Preferably, $L^7$ is absent and each connecting moiety Z is directly attached to S. If present, $L^7$ may be selected from —N(H)C(O)$CH_2$—, —N(H)C(O)$CF_2$— or —$CH_2$—.

S is a sugar or sugar derivative. The term "sugar derivative" is herein used to indicate a derivative of a monosaccharide sugar, i.e. a monosaccharide sugar comprising substituents and/or functional groups. Suitable examples for S include glucose (Glc), galactose (Gal), mannose (Man), fucose (Fuc), amino sugars and sugar acids, e.g. glucosamine ($GlcNH_2$), galactosamine ($GalNH_2$) N-acetylglucosamine (GlcNAc), N-acetylgalactosamine (GalNAc), sialic acid (Sia) which is also referred to as N-acetylneuraminic acid (NeuNAc), and N-acetylmuramic acid (MurNAc), glucuronic acid (GlcA) and iduronic acid (IdoA). Preferably, S is selected from Glc, Gal, GlcNAc and GalNAc. In an especially preferred embodiment, S is GalNAc.

xx is an integer that denotes the number of connecting groups Z that are attached to sugar (derivative) S. Thus, the (modified) antibody according to the invention contains a moiety S comprising xx reactive moieties F. Each of these reactive moieties F are reacted with reactive moiety Q of the compound according to general structure (1), such that xx connecting groups Z are formed and xx compounds according to general structure (1) are attached to a single occurrence of S. xx is 1 or 2, preferably xx=1.

yy is an integer that denotes the number of sugar(s) (derivatives) S, each having xx reactive groups F, that are connected to the antibody. yy is 1, 2, 3 or 4, preferably yy=2 or 4, most preferably yy=2. Thus, the (modified) antibody according to the invention contains yy moieties S, each of which comprises xx reactive moieties F. Each of these reactive moieties F are reacted with reactive moiety Q of the compound according to general structure (1), such that yy+xx connecting groups Z are formed and yy+xx compounds according to general structure (1) are attached to a single occurrence of S. Each compound according to general structure (1) may contain multiple payloads, e.g. by virtue of branching nitrogen atom N* in $L^1$. It is preferred that each compound according to general structure (1) contains 1 or 2 occurrences of D, most preferably 2 occurrences of D. In an especially preferred embodiment, linker L1 contains a branching nitrogen atom N* to which a second occurrence of D is connected.

The amount of payload (D) molecules attached to a single antibody is known in the art as the DAR (drug-antibody ratio). In the context of the present invention, it is preferred that DAR is an integer in the range 1-8, more preferably 2 or 4, most preferably DAR=4. Alternatively worded, the DAR is preferably an integer in the range (xx+yy) to [(xx+yy)×2], most preferably DAR=[(xx+yy)×2]. With preferred values for xx of 1 and yy of 2, the DAR is preferably 4. It will be appreciated that these are theoretical DAR values, and in practice the DAR may slightly deviate from this value, by virtue of incomplete conjugation. This is well-known in the art. However, the process for preparing the antibody-conjugates according to the invention is very effective, such that close-to-theoretical DAR values are obtained. For example, when the theoretical DAR is 4, DAR values above 3.6 or even above 3.8 are readily obtained.

Connecting Group Z

Z is a connecting group, that covalently connects both parts of the conjugate according to the invention. The term "connecting group" herein refers to the structural element, resulting from the reaction between Q and F, connecting one part of the conjugate with another part of the same conjugate. As will be understood by the person skilled in the art, the nature of a connecting group depends on the type of reaction with which the connection between the parts of said compound is obtained. As an example, when the carboxyl group of R—C(O)—OH is reacted with the amino group of $H_2N$—R' to form R—C(O)—N(H)—R', R is connected to R' via connecting group Z, and Z may be represented by the group —C(O)—N(H)—. Since connecting group Z originates from the reaction between Q and F, it can take any form.

Since more than one reactive moiety F can be present or introduced in an antibody, the antibody-conjugate according to the present invention may contain per biomolecule more than one payload D, such as 1-8 payloads D, preferably 1, 2, 3 or 4 payloads D, more preferably 2 or 4 payloads D. The number of payloads is typically an even integer, in view of the symmetric nature of antibodies. In other words, when one side of the antibody is functionalized with F, the symmetrical counterpart will also be functionalized. Alternatively, in case naturally occurring thiol groups of the cysteine residues of a protein are used as F, the value of m can be anything and may vary between individual conjugates.

In a compound according to structure (2), connecting group Z connects D via a linker to AB, optionally via $L^6$. Numerous reactions are known in the art for the attachment of a reactive group Q to a reactive group F. Consequently, a wide variety of connecting groups Z may be present in the conjugate according to the invention. In one embodiment, the reactive group Q is selected from the options described above, preferably as depicted in FIG. 1, and complementary reactive groups F and the thus obtained connecting groups Z are known to a person skilled in the art. Several examples of suitable combinations of F and Q, and of connecting group $Z^3$ that will be present in a bioconjugate when a linker-conjugate comprising Q is conjugated to a biomolecule comprising a complementary functional group F, are shown in FIG. 1.

For example, when F comprises or is a thiol group, complementary groups Q include N-maleimidyl groups and alkenyl groups, and the corresponding connecting groups Z are as shown in FIG. 1. When F comprises or is a thiol group, complementary groups Q also include allenamide groups.

For example, when F comprises or is an amino group, complementary groups Q include ketone groups and activated ester groups, and the corresponding connecting groups Z are as shown in FIG. 1.

For example, when F comprises or is a ketone group, complementary groups Q include (O-alkyl)hydroxylamino groups and hydrazine groups, and the corresponding connecting groups Z are as shown in FIG. 1.

For example, when F comprises or is an alkynyl group, complementary groups Q include azido groups, and the corresponding connecting group Z is as shown in FIG. 1.

For example, when F comprises or is an azido group, complementary groups Q include alkynyl groups, and the corresponding connecting group Z is as shown in FIG. 1.

For example, when F comprises or is a cyclopropenyl group, a trans-cyclooctene group or a cyclooctyne group, complementary groups Q include tetrazinyl groups, and the corresponding connecting group Z is as shown in FIG. 1. In these particular cases, Z is only an intermediate structure and will expel N2, thereby generating a dihydropyridazine (from the reaction with alkene) or pyridazine (from the reaction with alkyne).

Additional suitable combinations of F and Q, and the nature of resulting connecting group Z3 are known to a person skilled in the art, and are e.g. described in G. T. Hermanson, "Bioconjugate Techniques", Elsevier, 3rd Ed. 2013 (ISBN:978-0-12-382239-0), in particular in Chapter 3, pages 229-258, incorporated by reference. A list of complementary reactive groups suitable for bioconjugation processes is disclosed in Table 3.1, pages 230-232 of Chapter 3 of G. T. Hermanson, "Bioconjugate Techniques", Elsevier, 3rd Ed. 2013 (ISBN:978-0-12-382239-0), and the content of this Table is expressly incorporated by reference herein.

In a preferred embodiment, connecting group Z is according to any one of structures (Za) to (Zj), more preferably according to structures (Za), (Ze), (Zf), (Zi) or (Zj), most preferably according to structure (Zj). Structures (Za) to (Zh) are as follows:

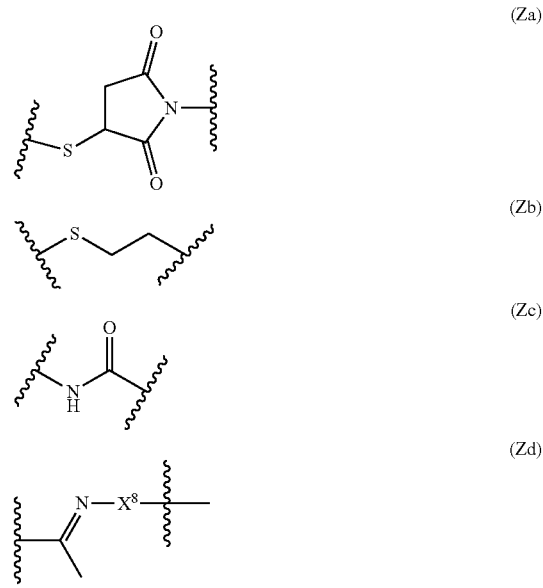

-continued (Ze)

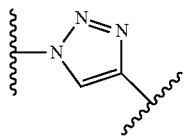

(Zf)

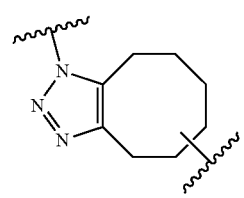

(Zg)

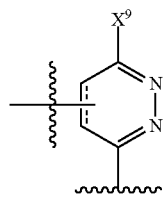

(Zh)

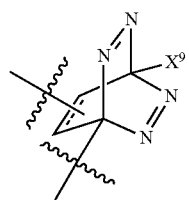

Herein,

X$^8$ is O or NH.

X$^9$ is selected from H, methyl and pyridyl.

In structure (Zg) and (Zh), the ---- bond represents either a single or a double bond, and to (L$^1$)$_d$ or (L$^2$)$_e$ may be connected via either side of this bond.

The wavy lines indicate the connection to (L$^1$)$_d$ and to (L$^2$)$_e$. The connectivity depends on the specific nature of Q and F. Although either site of the connecting groups according to (Za) to (Zg) may be connected to (L$^1$)$_d$, it is preferred that the left-most of these groups as depicted is connected to (L$^1$)$_d$.

Connecting group (Zh) typically rearranges to (Zg) with the liberation of N$_2$.

In an especially preferred embodiment, connecting group Z comprises a triazole moiety and is according to structure (Zi):

(Zi)

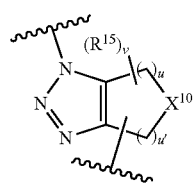

Herein, R$^{15}$, X$^{10}$, u, u' and v are as defined for (Q36), and all preferred embodiments thereof equally apply to (Zi). The wavy lines indicate the connection to (L$^1$)$_d$ or (L$^2$)$_e$, and the connectivity depends on the specific nature of Q and F. Although either site of the connecting group according to (Zi) may be connected to (L$^1$)$_d$, it is preferred that the left wavy bond as depicted represents the connectivity to (L$^1$)$_d$. The connecting groups according to structure (Zf) and (Zj) are preferred embodiments of the connecting group according to (Zj).

In an especially preferred embodiment, connecting group Z comprises a triazole moiety and is according to structure (Zj):

(Zj)

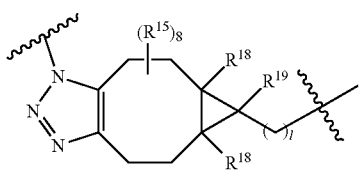

Herein, R$^{15}$, R$^{18}$, R$^{19}$, and l are as defined for (Q37), and all preferred embodiments thereof equally apply to (Zj). The wavy lines indicate the connection to (L$^1$)$_d$ or (L$^2$)$_e$, and the connectivity depends on the specific nature of Q and F. Although either site of the connecting group according to (Zj) may be connected to (L$^1$)$_d$, it is preferred that the left wavy bond as depicted represents the connectivity to (L$^1$)$_d$.

In a preferred embodiment, Q comprises or is an alkyne moiety and F is an azido moiety, such that connecting group Z comprises an triazole moiety. Preferred connecting groups comprising a triazole moiety are the connecting groups according to structure (Ze) or (Zi), wherein the connecting groups according to structure (Zi) is preferably according to structure (Zj) or (Zf). In a preferred embodiment, the connecting groups is according to structure (Zi), more preferably according to structure (Zj) or (Zf).

Preferred Antibody-Conjugates

Preferred antibody-conjugates according to the first aspect are selected from the group consisting of compounds (I)-(III). More preferred antibody-conjugates are selected from (X)-(XXIX). In one especially preferred embodiment, the antibody-conjugates is selected from (X), (XII), (XIII), (XIV), (XV), (XXII), (XXIV) and (XXVIII). In one especially preferred embodiment, the antibody-conjugates is (XXII). The structures of these antibody-conjugates are defined here below.

Antibody-conjugate (I) has the following structure:

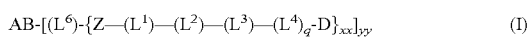  (I)

wherein:

AB, L$^6$, Z, D, xx and yy are as defined above;

L$^1$ is a linker represented by -(A)$_d$-(B)$_e$-(A)$_f$-(C(O))$_g$—, as defined above;

L$^2$ is Val-Cit or Val-Ala;

L$^3$ is the PABC derivative according to structure (25);

L$^4$ is —N—(C$_x$-alkylene)-C(O)—, wherein x is an integer in the range 1 to 20;

q=0 or 1.

In the context of antibody-conjugate (I), it is preferred that for L$^1$, d=1 (A according to structure (23), it is preferred that a=1 and R$^{13}$=H), e=2, f=0 and g=1. In the context of antibody-conjugate (I), it is preferred that L$^2$=Val-Cit. In the context of antibody-conjugate (I), it is preferred that for L$^3$, R$^3$=H. In the context of antibody-conjugate (I), it is preferred that in case q=1, then x=1 or 5.

Antibody-conjugate (II) has the following structure:

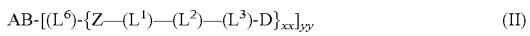

wherein:
AB, $L^6$, Z, D, xx and yy are as defined above;
$L^1$ is a linker represented by -(A)-(B)$_e$—(C(O))—, as defined above;
$L^2$ is Val-Cit or Val-Ala;
$L^3$ is the PABC derivative according to structure (25), wherein $R^3$=H.

In the context of antibody-conjugate (II), it is preferred that for $L^1$, e=2, A according to structure (23), it is preferred that a=1 and $R^{13}$=H. In the context of antibody-conjugate (II), it is preferred that $L^2$=Val-Cit.

Antibody-conjugate (III) has the following structure:

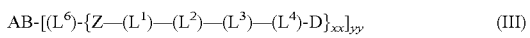

wherein:
AB, $L^6$, Z, D, xx and yy are as defined above;
$L^1$ is a linker represented by -(A)-(B)$_e$—(C(O))—, as defined above;
$L^2$ is Val-Cit or Val-Ala;
$L^3$ is the PABC derivative according to structure (25), wherein $R^3$=H;
$L^4$ is —N—($C_x$-alkylene)-C(O)—, wherein x is an integer in the range 1 to 6.

In the context of antibody-conjugate (III), it is preferred that for $L^1$, e=2, and with a=1 and $R^{13}$=H. In the context of antibody-conjugate (III), it is preferred that $L^2$=Val-Cit. In the context of antibody-conjugate (III), it is preferred that x=1 or 5.

Antibody-conjugate (X) has a linker-payload moiety according to the following structure:

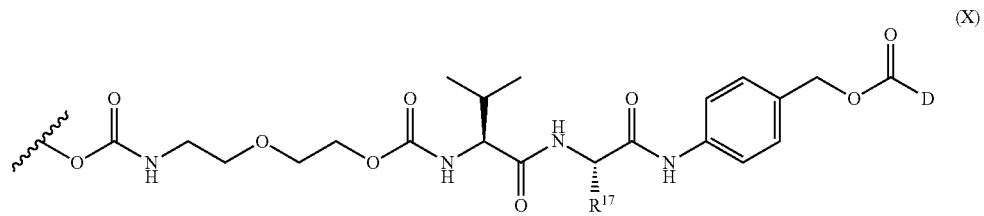

Herein, the wavy line indicates the connection to Z; D and $R^{17}$ are as defined above.

For preferred antibody-conjugate (Xa), $R^{17}$ is $CH_3$. For preferred antibody-conjugate (Xb), $R^{17}$ is $CH_2CH_2CH_2NHC(O)NH_2$.

Antibody-conjugate (XI) has a linker-payload moiety according to the following structure:

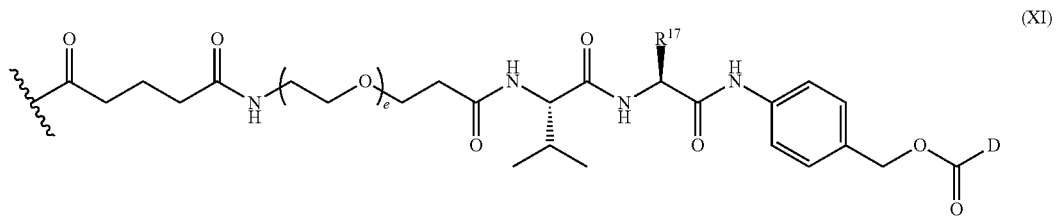

Herein, the wavy line indicates the connection to Z; D, e and $R^{17}$ are as defined above.

For preferred antibody-conjugate (XIa), e is 4; and $R^{17}$ is $CH_3$. For preferred antibody-conjugate (XIb), e is 4; and $R^{17}$ is $CH_2CH_2CH_2NHC(O)NH_2$.

Antibody-conjugate (XII) has a linker-payload moiety according to the following structure:

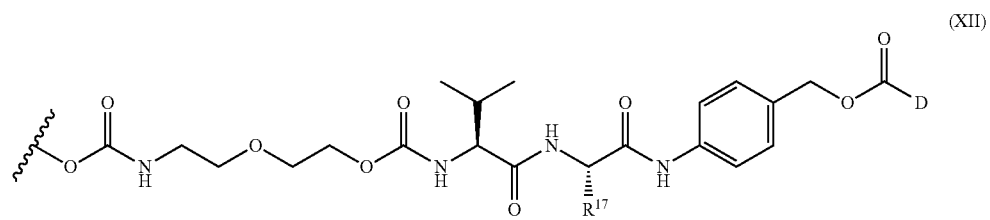

Herein, the wavy line indicates the connection to Z; D and $R^{17}$ are as defined above.

For preferred antibody-conjugate (XIIa), $R^{17}$ is $CH_3$. For preferred antibody-conjugate (XIIb), $R^{17}$ is $CH_2CH_2CH_2NHC(O)NH_2$.

Antibody-conjugate (XIII) has a linker-payload moiety according to the following structure:

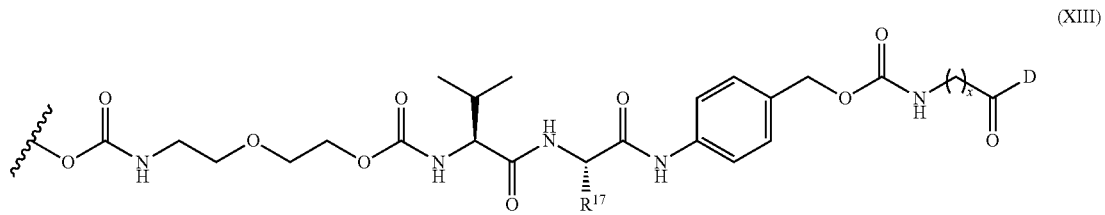

(XIII)

Herein, the wavy line indicates the connection to Z; D, x and $R^{17}$ are as defined above.

For preferred antibody-conjugate (XIIIa), x=1; and $R^{17}$=$CH_3$. For preferred antibody-conjugate (XIIIb), x=5; and $R^{17}$=$CH_3$. For preferred antibody-conjugate (XIIIc), x=1; and $R^{17}$=$CH_2CH_2CH_2NHC(O)NH_2$. For preferred antibody-conjugate (XIIId), x=5; and $R^{17}$=$CH_2CH_2CH_2NHC(O)NH_2$.

Antibody-conjugate (XIV) has a linker-payload moiety according to the following structure:

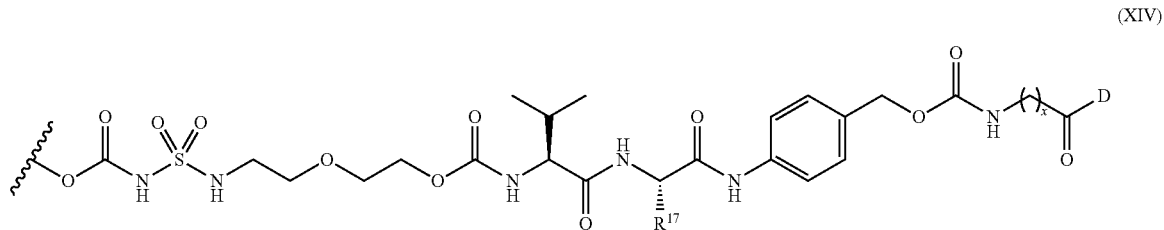

(XIV)

Herein, the wavy line indicates the connection to Z; D, x and $R^{17}$ are as defined above.

For preferred antibody-conjugate (XIVa), x=1; and $R^{17}$=$CH_3$. For preferred antibody-conjugate (XIVb), x=6; and $R^{17}$=$CH_3$. For preferred antibody-conjugate (XIVc), x=1; and $R^{17}$=$CH_2CH_2CH_2NHC(O)NH_2$. For preferred antibody-conjugate (XIVd), x=5; and $R^{17}$=$CH_2CH_2CH_2NHC(O)NH_2$.

Antibody-conjugate (XV) has a linker-payload moiety according to the following structure:

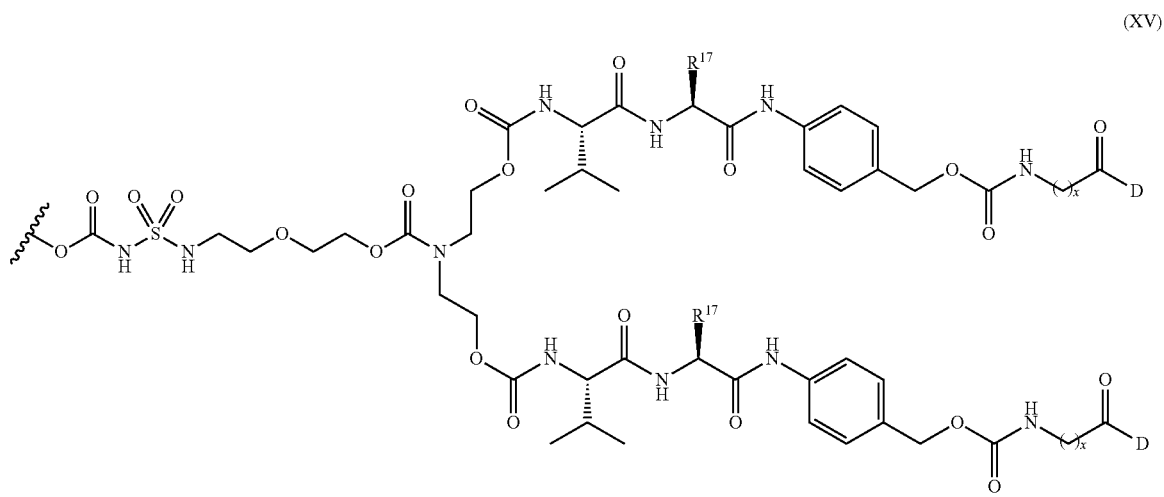

(XV)

Herein, the wavy line indicates the connection to Z; D, x and R$^{17}$ are as defined above.

For preferred antibody-conjugate (XVa), each x=1; and each R$^{17}$=CH$_3$. For preferred antibody-conjugate (XVb), each x=5; and each R$^{17}$=CH$_3$. For preferred antibody-conjugate (XVc), each x=1; and each R$^{17}$=CH$_2$CH$_2$CH$_2$NHC(O)NH$_2$. For preferred antibody-conjugate (XVd), x=5; and each R$^{17}$=CH$_2$CH$_2$CH$_2$NHC(O)NH$_2$.

Antibody-conjugate (XVI) has a linker-payload moiety according to the following structure:

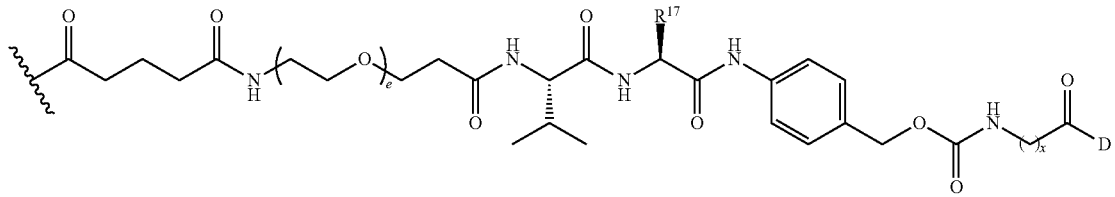

(XVI)

Herein, the wavy line indicates the connection to Z; D, e, x and R$^{17}$ are as defined above.

For preferred antibody-conjugate (XVIa), e=4; x=1; and R$^{17}$=CH$_3$. For preferred antibody-conjugate (XVIb), e=4; x=1; and R$^{17}$=CH$_2$CH$_2$CH$_2$NHC(O)NH$_2$.

Antibody-conjugate (XVII) has a linker-payload moiety according to the following structure:

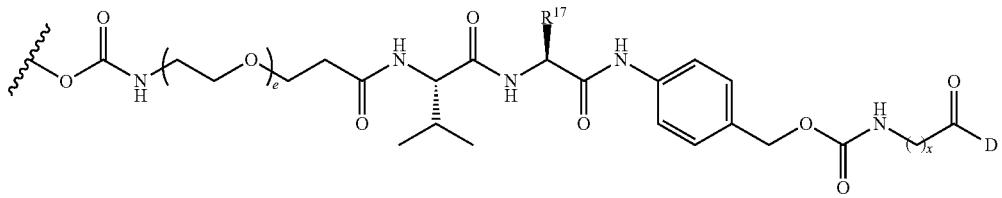

(XVII)

Herein, the wavy line indicates the connection to Z; D, e, x and R$^{17}$ are as defined above.

For preferred antibody-conjugate (XVIIa), e=4; x=1; and R$^{17}$=CH$_3$. For preferred antibody-conjugate (XVIIb), e=4; x=1; and R$^{17}$=CH$_2$CH$_2$CH$_2$NHC(O)NH$_2$. For preferred antibody-conjugate (XVIIc), e=4; x=6; and R$^{17}$=CH$_3$. For preferred antibody-conjugate (XVIId), e=4; x=6; and R$^{17}$=CH$_2$CH$_2$CH$_2$NHC(O)NH$_2$.

Antibody-conjugate (XVIII) has a linker-payload moiety according to the following structure:

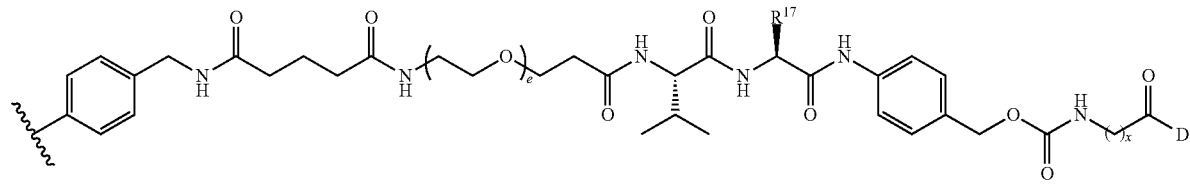

(XVIII)

Herein, the wavy line indicates the connection to Z; D, e, x and R$^{17}$ are as defined above.

For preferred antibody-conjugate (XVIIIa), e=4; x=1; and R$^{17}$=CH$_3$. For preferred antibody-conjugate (XVIIIb), e=4; x=1; and R$^{17}$=CH$_2$CH$_2$CH$_2$NHC(O)NH$_2$. For preferred antibody-conjugate (XVIIIc), e=4; x=5; and R$^{17}$=CH$_3$. For preferred antibody-conjugate (XVIIId), e=4; x=5; and R$^{17}$=CH$_2$CH$_2$CH$_2$NHC(O)NH$_2$.

Antibody-conjugate (XIX) has a linker-payload moiety according to the following structure:

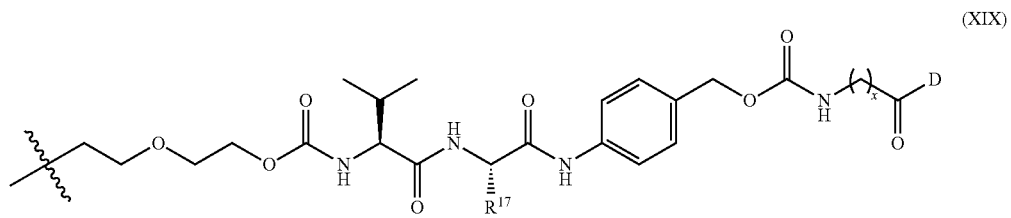

(XIX)

Herein, the wavy line indicates the connection to Z; D, x and $R^{17}$ are as defined above.

For preferred antibody-conjugate (XIXa), x=1; and $R^{17}$=CH$_3$. For preferred antibody-conjugate (XIXb), x=5; and $R^{17}$=CH$_3$. For preferred antibody-conjugate (XIXc), x=1; and $R^{17}$=CH$_2$CH$_2$CH$_2$NHC(O)NH$_2$. For preferred antibody-conjugate (XIXd), x=5; and $R^{17}$=CH$_2$CH$_2$CH$_2$NHC(O)NH$_2$.

Antibody-conjugate (XX) has a linker-payload moiety according to the following structure:

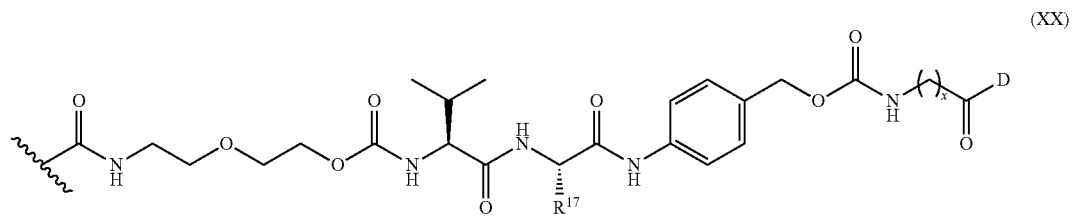

(XX)

Herein, the wavy line indicates the connection to Z; D, x and $R^{17}$ are as defined above.

For preferred antibody-conjugate (XXa), x=1; and $R^{17}$=CH$_3$. For preferred antibody-conjugate (XXb), x=5; and $R^{17}$=CH$_3$. For preferred antibody-conjugate (XXc), x=1; and $R^{17}$=CH$_2$CH$_2$CH$_2$NHC(O)NH$_2$. For preferred antibody-conjugate (XXd), x=5; and $R^{17}$=CH$_2$CH$_2$ CH$_2$NHC(O)NH$_2$.

Antibody-conjugate (XXI) has a linker-payload moiety according to the following structure:

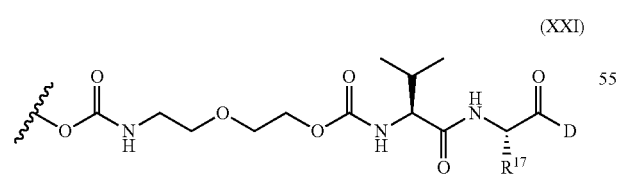

(XXI)

Herein, the wavy line indicates the connection to Z; D and $R^{17}$ are as defined above.

For preferred antibody-conjugate (XXIa), $R^{17}$ is CH$_3$. For preferred antibody-conjugate (XXIb), $R^{17}$ is CH$_2$CH$_2$CH$_2$NHC(O)NH$_2$.

Antibody-conjugate (XXII) has a linker-payload moiety according to the following structure:

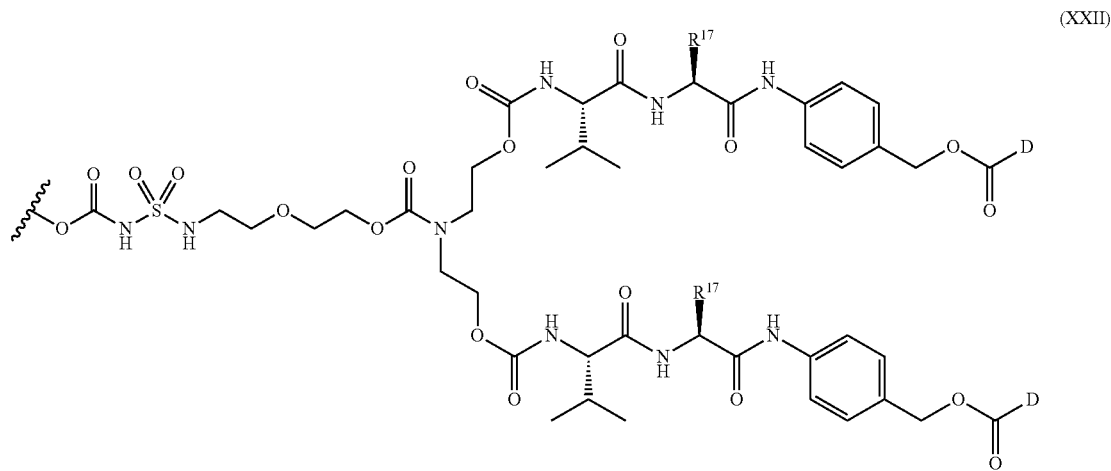

(XXII)

Herein, the wavy line indicates the connection to Z; D, x and $R^{17}$ are as defined above.

For preferred antibody-conjugate (XXIIa), each x=1; and each $R^{17}$=CH$_3$. For preferred antibody-conjugate (XXIIb), each x=5; and each $R^{17}$=CH$_3$. For preferred antibody-conjugate (XXIIc), each x=1; and each $R^{17}$=CH$_2$CH$_2$CH$_2$NHC(O)NH$_2$. For preferred antibody-conjugate (XXIId), each x=5; and each $R^{17}$=CH$_2$CH$_2$CH$_2$NHC(O)NH$_2$.

Antibody-conjugate (XXIII) has a linker-payload moiety according to the following structure:

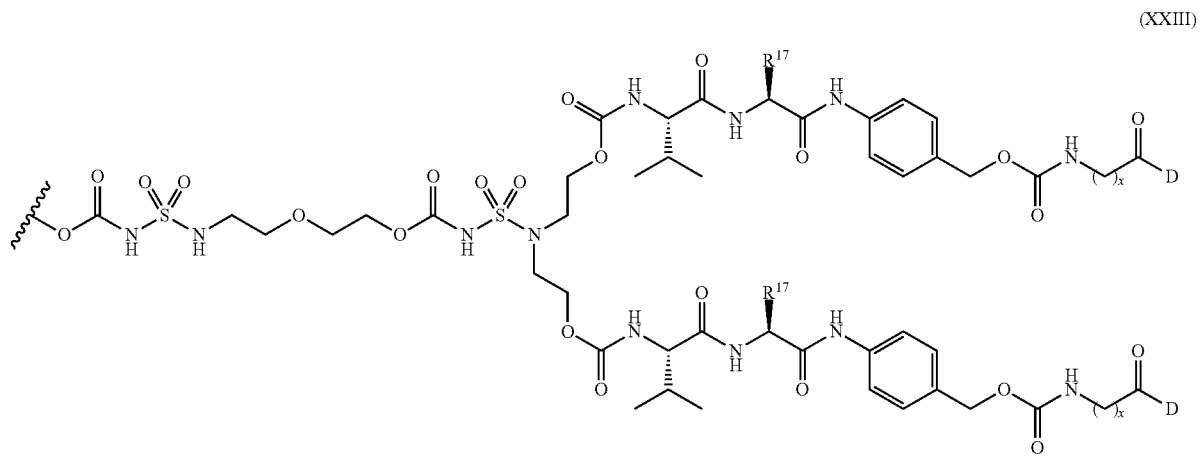

(XXIII)

Herein, the wavy line indicates the connection to Z; D, x and $R^{17}$ are as defined above.

For preferred antibody-conjugate (XXIIIa), each x=1; and each $R^{17}$=CH$_3$. For preferred antibody-conjugate (XXIIIb), each x=5; and each $R^{17}$=CH$_3$. For preferred antibody-conjugate (XXIIIc), each x=1; and each $R^{17}$=CH$_2$CH$_2$CH$_2$NHC(O)NH$_2$. For preferred antibody-conjugate (XXIIId), each x=5; and each $R^{17}$=CH$_2$CH$_2$CH$_2$NHC(O)NH$_2$.

Antibody-conjugate (XXIV) has a linker-payload moiety according to the following structure:

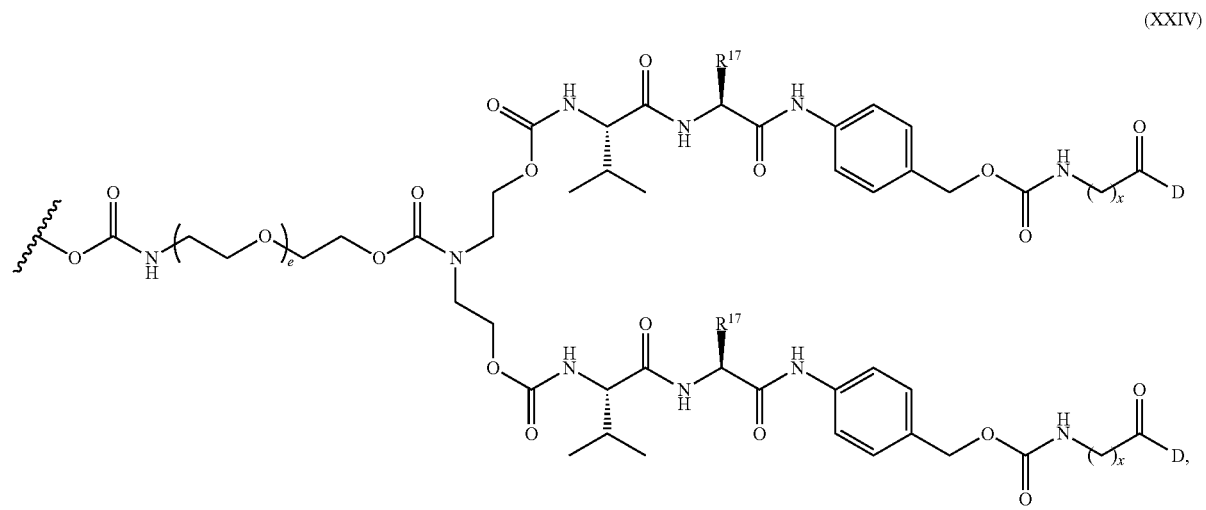

(XXIV)

Herein, the wavy line indicates the connection to Z; D, x and $R^{17}$ are as defined above.

For preferred antibody-conjugate (XXIVa), each x=1; and each $R^{17}$=$CH_3$. For preferred antibody-conjugate (XXIVb), each x=5; and each $R^{17}$=$CH_3$. For preferred antibody-conjugate (XXIVc), each x=1; and each $R^{17}$=$CH_2CH_2CH_2NHC(O)NH_2$. For preferred antibody-conjugate (XXIVd), each x=5; and each $R^{17}$=$CH_2CH_2CH_2NHC(O)NH_2$.

Antibody-conjugate (XXV) has a linker-payload moiety according to the following structure:

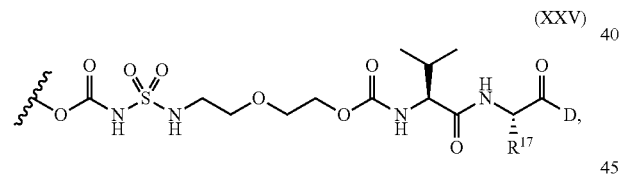

(XXV)

Herein, the wavy line indicates the connection to Z; D and $R^{17}$ are as defined above.

For preferred antibody-conjugate (XXVa), $R^{17}$=$CH_3$. For preferred antibody-conjugate (XXVb), $R^{17}$=$CH_2CH_2CH_2NHC(O)NH_2$.

Antibody-conjugate (XXVI) has a linker-payload moiety according to the following structure:

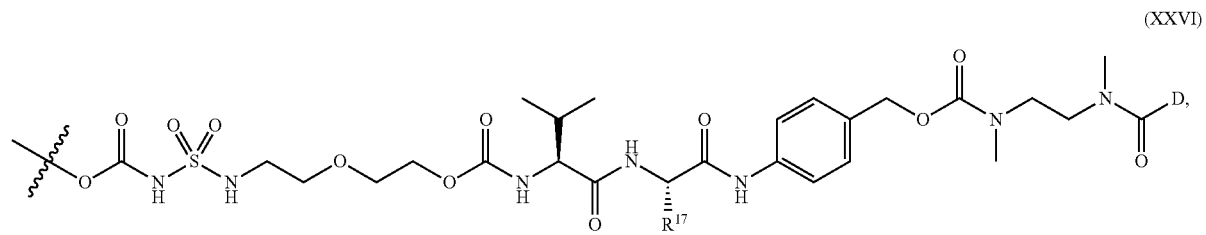

(XXVI)

Herein, the wavy line indicates the connection to Z; D and $R^{17}$ are as defined above.

For preferred antibody-conjugate (XXVIa), $R^{17}$=CH$_3$.
For preferred antibody-conjugate (XXVIb), $R^{17}$=CH$_2$CH$_2$CH$_2$NHC(O)NH$_2$.

Antibody-conjugate (XXVII) has a linker-payload moiety according to the following structure:

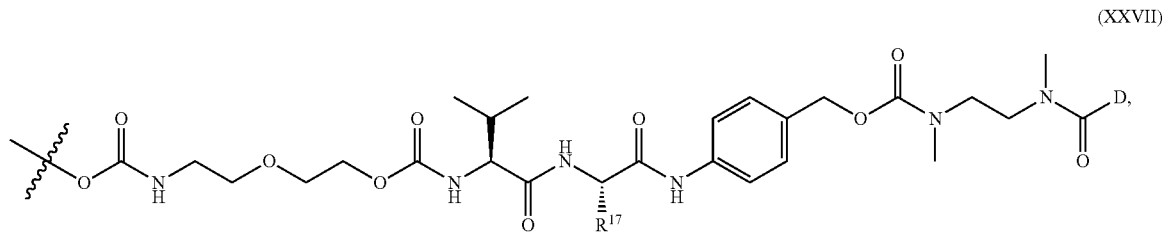

(XXVII)

Herein, the wavy line indicates the connection to Z; D and $R^{17}$ are as defined above.

For preferred antibody-conjugate (XXVIIa), $R^{17}$=CH$_3$.
For preferred antibody-conjugate (XXVIIb), $R^{17}$=CH$_2$CH$_2$CH$_2$NHC(O)NH$_2$.

Antibody-conjugate (XXVIII) has a linker-payload moiety according to the following structure:

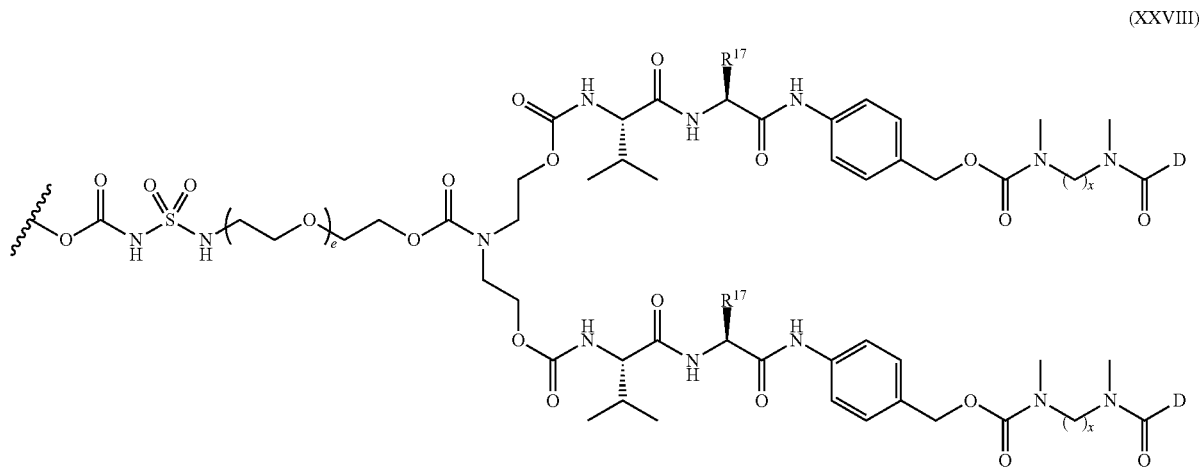

(XXVIII)

Herein, the wavy line indicates the connection to Z; D, x, e and $R^{17}$ are as defined above.

For preferred antibody-conjugate (XXVIIIa), e=1; each x=2; and each $R^{17}$=CH$_3$. For preferred antibody-conjugate (XXVIIIb), e=1; each x=5; and each $R^{17}$=CH$_3$. For preferred antibody-conjugate (XXVIIIc), e=1; each x=1; and each $R^{17}$=CH$_2$CH$_2$CH$_2$NHC(O)NH$_2$. For preferred antibody-conjugate (XXVIIId), e=1; each x=5; and each $R^{17}$=CH$_2$CH$_2$CH$_2$NHC(O)NH$_2$. Antibody-conjugates (XXVIIIa) and (XXVIIIc) are especially preferred.

Antibody-conjugate (XXIX) has a linker-payload moiety according to the following structure:

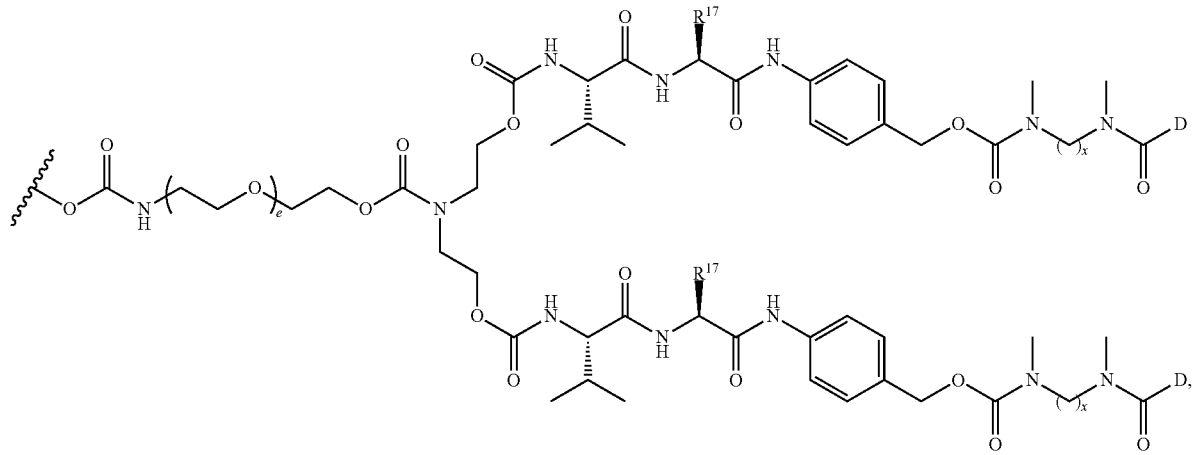

(XXIX)

Herein, the wavy line indicates the connection to Z; D, x, e and $R^{17}$ are as defined above.

For preferred antibody-conjugate (XXIXa), e=1; each x=2; and each $R^{17}$=$CH_3$. For preferred antibody-conjugate (XXIXb), e=1; each x=5; and each $R^{17}$=$CH_3$. For preferred antibody-conjugate (XXIXc), e=1; each x=1; and each $R^{17}$=$CH_2CH_2CH_2NHC(O)NH_2$. For preferred antibody-conjugate (XXIXd), e=1; each x=5; and each $R^{17}$=$CH_2CH_2CH_2NHC(O)NH_2$. Antibody-conjugates (XXIXa) and (XXIXc) are especially preferred.

In a preferred embodiment, the antibody-conjugate according to the invention is selected from the group consisting of antibody-conjugates (I)-(III). In a preferred embodiment, the antibody-conjugate according to the invention is selected from the group consisting of antibody-conjugates (II) and (III). In a preferred embodiment, the antibody-conjugate according to the invention is selected from the group consisting of antibody-conjugates (X)-(XXIX). In a preferred embodiment, the antibody-conjugate according to the invention is selected from the group consisting of antibody-conjugates (X)-(XX). In a preferred embodiment, the antibody-conjugate according to the invention is selected from the group consisting of antibody-conjugates (X), (XII), (XIII), (XIV), (XV), (XXII), (XXIV) and (XXVIII). In a preferred embodiment, the antibody-conjugate according to the invention has structure (XXII) or (XXVIII).

Process for Synthesising the Antibody-Conjugate According to General Structure (2)

In a further aspect, the present invention relates to a process for the preparation of the antibody-conjugate according to the invention, the process comprising the step of reacting Q of the compound according to the invention with a functional group F of an antibody. The compound according to general structure (1), and preferred embodiments thereof, are described in more detail above. The present process occurs under conditions such that Q is reacted with F to covalently link the antibody AB to the payload D. In the process according to the invention, Q reacts with F, forming a covalent connection between the antibody and the compound according to the invention.

Complementary reactive groups Q and functional groups F are known to the skilled person and are described in more detail below.

The process according to the present aspect preferably concerns a click reaction, more preferably a 1,3-dipolar cycloaddition, most preferably an alkyne/azide cycloaddition. Most preferably, Q is or comprises an alkyne group and F is an azido group. Click reactions, such as 1,3-dipolar cycloadditions, are known in the art, and the skilled person knows how to perform them.

In the process according to the present aspect, more than one functional group F may be present in the antibody. When two or more functional groups are present, said groups may be the same or different. For example, an antibody comprising two functional groups F, i.e. $F^1$ and $F^2$, may react with two compounds comprising a functional group $Q^1$, which may be the same or different, to form an antibody-conjugate. The functional group in the antibody may be naturally present or may be placed in the antibody by a specific technique, for example a (bio)chemical or a genetic technique. The functional group that is placed in the antibody is prepared by chemical synthesis, for example an azide or a terminal alkyne. F is group capable of reacting in a click reaction, such as a diene, a dienophile, a 1,3-dipole or a dipolarophile, preferably F is selected from the group of 1,3-dipoles (typically an azido group or diazo group) or a dipolarophile (typically an alkenyl or alkynyl group). Herein, F is a 1,3-dipole when Q is a dipolarophile and F is a dipolarophile when Q is a 1,3-dipole, or F is a diene when Q is a dienophile and F is a dienophile when Q is a diene. Most preferably, $F^1$ is a 1,3-dipole, preferably $F^1$ is or comprises an azido group.

Methods of preparing modified glycoproteins are known in the art, e.g. from WO 2014/065661, WO 2016/170186 and WO 2016/053107, which are incorporated herein by reference. From the same documents, the conjugation reaction between the modified glycoprotein and a compound comprising a cytotoxin and a click probe is known to the skilled person.

Thus, in one aspect the invention concerns a process for preparing the antibody-conjugate according to the invention, wherein the process comprising:

(i) contacting an antibody comprising yy core N-acetylglucosamine (GlcNAc) moieties, wherein yy=1, 2, 3 or 4, with a compound of the formula $S(F)_{xx}$—P in the presence of a catalyst, wherein $S(F)_{xx}$ is a sugar derivative comprising xx reactive groups F capable of reacting with a functional group Q, xx is 1 or 2 and P is a nucleoside mono- or diphosphate, and wherein the catalyst is capable of transferring the $S(F)_{xx}$ moiety to the core-GlcNAc moiety, to obtain a modified antibody according to Formula (26):

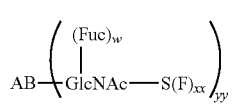

(26)

wherein
   AB is an antibody capable of targeting Trop-2-expressing tumours;
   Fuc is fucose;
   w is 0 or 1; and
(ii) reacting the modified antibody with a compound according to general structure (1), to obtain the antibody-conjugate.

Step (i)

In step (i), an antibody comprising 1 or 2 core N-acetylglucosamine moieties is contacted with a compound of the formula $S(F)_{xx}$—P in the presence of a catalyst, wherein $S(F)_{xx}$ is a sugar derivative comprising xx functional groups F capable of reacting with a functional group Q, xx is 1 or 2 and P is a nucleoside mono- or diphosphate, and wherein the catalyst is capable of transferring the $S(F)_{xx}$ moiety to the core-GlcNAc moiety. Herein, the antibody is typically an antibody that has been trimmed to a core-GlcNAc residue as described further below. Step (i) affords a modified antibody according to Formula (26).

The starting material, i.e. the antibody comprising a core-GlcNAc substituent, is known in the art and can be prepared by methods known by the skilled person. In one embodiment, the process according to the invention further comprises the deglycosylation of an antibody glycan having a core N-acetylglucosamine, in the presence of an endoglycosidase, in order to obtain an antibody comprising a core N-acetylglucosamine substituent, wherein said core N-acetylglucosamine and said core N-acetylglucosamine substituent are optionally fucosylated. Depending on the nature of the glycan, a suitable endoglycosidase may be selected. The endoglycosidase is preferably selected from the group consisting of EndoS, EndoA, EndoE, EfEndo18A, EndoF, EndoM, EndoD, EndoH, EndoT and EndoSH and/or a combination thereof, the selection of which depends on the nature of the glycan. EndoSH is described in PCT/EP2017/052792, see Examples 1-3, and SEQ. ID No: 1, which is incorporated by reference herein.

Structural features S, F and xx are defined above for the antibody-conjugate according to the invention, which equally applies to the present aspect. Compounds of the formula $S(F)_{xx}$—P, wherein a nucleoside monophosphate or a nucleoside diphosphate P is linked to a sugar derivative $S(F)_{xx}$ are known in the art. For example Wang et al., Chem. Eur. J. 2010, 16, 13343-13345, Piller et al., ACS Chem. Biol. 2012, 7, 753, Piller et al., Bioorg. Med. Chem. Lett. 2005, 15, 5459-5462 and WO 2009/102820, all incorporated by reference herein, disclose a number of compounds $S(F)_{xx}$—P and their syntheses. In a preferred embodiment nucleoside mono- or diphosphate P in $S(F)_{xx}$—P is selected from the group consisting of uridine diphosphate (UDP), guanosine diphosphate (GDP), thymidine diphosphate (TDP), cytidine diphosphate (CDP) and cytidine monophosphate (CMP), more preferably P is selected from the group consisting of uridine diphosphate (UDP), guanosine diphosphate (GDP) and cytidine diphosphate (CDP), most preferably P=UDP. Preferably, $S(F)_{xx}$—P is selected from the group consisting of GalNAz-UDP, F2-GalNAz-UDP (N-(azidodifluoro)acetylgalactosamine), 6-AzGal-UDP, 6-AzGalNAc-UDP (6-azido-6-deoxy-N-acetylgalactosamine-UDP), 4-AzGalNAz-UDP, 6-AzGalNAz-UDP, 6-AzGlc-UDP, 6-AzGlcNAz-UDP and 2-(but-3-yonic acid amido)-2-deoxy-galactose-UDP. Most preferably, $S(F)_{xx}$—P is GalNAz-UDP or 6-AzGalNAc-UDP.

Suitable catalyst that are capable of transferring the $S(F)_{xx}$ moiety to the core-GlcNAc moiety are known in the art. A suitable catalyst is a catalyst wherefore the specific sugar derivative nucleotide $S(F)_{xx}$—P in that specific process is a substrate. More specifically, the catalyst catalyzes the formation of a β(1,4)-glycosidic bond. Preferably, the catalyst is selected from the group of galactosyltransferases and N-acetylgalactosaminyltransferases, more preferably from the group of β(1,4)-N-acetylgalactosaminyltransferases (GalNAcT) and β(1,4)-galactosyltransferases (GalT), most preferably from the group of β(1,4)-N-acetylgalactosaminyltransferases having a mutant catalytic domain. Suitable catalysts and mutants thereof are disclosed in WO 2014/065661, WO 2016/022027 and WO 2016/170186, all incorporated herein by reference. In one embodiment, the catalyst is a wild-type galactosyltransferase or N-acetylgalactosaminyltransferase, preferably a N-acetylgalactosaminyltransferase. In an alternative embodiment, the catalyst is a mutant galactosyltransferase or N-acetylgalactosaminyltransferases, preferably a mutant N-acetylgalactosaminyltransferase. Mutant enzymes described in WO 2016/022027 and WO 2016/170186 are especially preferred. These galactosyltransferase (mutant) enzyme catalysts are able to recognize internal sugars and sugar derivatives as an acceptor. Thus, sugar derivative $S(F)_{xx}$ is linked to the core-GlcNAc substituent in step (i), irrespective of whether said GlcNAc is fucosylated or not.

Step (i) is preferably performed in a suitable buffer solution, such as for example phosphate, buffered saline (e.g. phosphate-buffered saline, tris-buffered saline), citrate, HEPES, tris and glycine. Suitable buffers are known in the art. Preferably, the buffer solution is phosphate-buffered saline (PBS) or tris buffer. Step (i) is preferably performed at a temperature in the range of about 4 to about 50° C., more preferably in the range of about 10 to about 45° C., even more preferably in the range of about 20 to about 40° C., and most preferably in the range of about 30 to about 37° C. Step (i) is preferably performed a pH in the range of about 5 to about 9, preferably in the range of about 5.5 to about 8.5, more preferably in the range of about 6 to about 8. Most preferably, step (i) is performed at a pH in the range of about 7 to about 8.

Step (ii)

In step (ii), the modified antibody is reacted with a compound according to general structure (1), comprising a reactive group Q capable of reacting with reactive group F and a target molecule D, to obtain the antibody-conjugate containing connecting group Z resulting from the reaction between Q and F. Such reaction occurs under condition such that reactive group Q is reacted with the functional group F of the biomolecule to covalently link the antibody to the compound according to general structure (1).

In a preferred embodiment, in step (ii) an azide on an azide-modified antibody reacts with an alkynyl group, preferably a terminal alkynyl group, or a (hetero)cycloalkynyl group of the compound according to general structure (1), via a cycloaddition reaction. This cycloaddition reaction of a molecule comprising an azide with a molecule comprising a terminal alkynyl group or a (hetero)cycloalkynyl group is one of the reactions that is known in the art as "click chemistry". In the case of a linker-conjugate comprising a terminal alkynyl group, said cycloaddition reaction needs to be performed in the presence of a suitable catalyst, preferably a Cu(I) catalyst. However, in a preferred embodiment, the linker-conjugate comprises a (hetero)cycloalkynyl group, more preferably a strained (hetero)cycloalkynyl group. When the (hetero)cycloalkynyl is a strained (hetero)cycloalkynyl group, the presence of a catalyst is not required, and said reaction may even occur spontaneously by a reaction called strain-promoted azide-alkyne cycloaddition (SPAAC). This is one of the reactions known in the art as "metal-free click chemistry".

Application

The invention further concerns a method for the treatment of a subject in need thereof, comprising the administration of the antibody-conjugate according to the invention as defined above. The subject in need thereof is typically a cancer patient. The use of antibody-conjugates, such as antibody-drug conjugates, is well-known in the field of cancer treatment, and the antibody-conjugates according to the invention are especially suited in this respect. The method as described is typically suited for the treatment of cancer. In the method according to this aspect, the antibody-conjugate is typically administered in a therapeutically effective dose. The present aspect of the invention can also be worded as an antibody-conjugate according to the invention for use in the treatment of a subject in need thereof, preferably for the treatment of cancer. In other words, this aspect concerns the use of an antibody-conjugate according to the invention for the preparation of a medicament or pharmaceutical composition for use in the treatment of a subject in need thereof, preferably for use in the treatment of cancer. In the present context, treatment of cancer is envisioned to encompass treating, imaging, diagnosing, preventing the proliferation of, containing and reducing tumours.

This aspect of the present invention may also be worded as a method for targeting Trop-2-expressing cells, comprising administering to a subject in need thereof the antibody-conjugate according to the invention. The targeting of Trop-2-expressing cells preferably includes one or more of treating, imaging, diagnosing, preventing the proliferation of, containing and reducing Trop-2-expressing cells, in particular Trop-2-expressing tumours.

In the context of the present invention, the subject may suffer from a disorder selected from breast cancer, ovary cancer, non-small cell lung cancer (NSCLC), squamous cell cancer of head and neck (SCCHN), colon cancer, neuroendocrine cancer, prostate cancer, sarcoma, stomach cancer, esophageal cancer, cervical cancer, in particular wherein the subject suffers from breast cancer or ovary cancer.

The inventors have surprisingly found that the antibody-conjugates according to the invention are superior to conventional Trop-2-targeting antibody-conjugates in terms of safety and/or efficacy, such that the therapeutic index of the antibody-conjugate according to the invention is increased with respect to conventional Trop-2-targeting antibody-conjugates.

Mode of Conjugation

In the context of the present invention, the "mode of conjugation" refers to the process that is used to conjugate a target molecule D to an antibody AB, as well as to the structural features of the resulting antibody-conjugate, in particular of the linker that connects the target molecule to the antibody, that are a direct consequence of the process of conjugation. Thus, in one embodiment, the mode of conjugation refers to a process for conjugation a target molecule to an antibody. In an alternative embodiment, the mode of conjugation refers to structural features of the linker and/or to the attachment point of the linker to the antibody that are a direct consequence of the process for conjugation a target molecule to an antibody.

In a further aspect, the invention concerns the use of a mode of conjugation for increasing the therapeutic index of an antibody-conjugate in the treatment of Trop-2-expressing tumours, wherein the mode of conjugation is being used to connect antibody AB with payload D via a linker L. The mode of conjugation mode of conjugation comprises:

(i) contacting an antibody AB comprising yy core N-acetylglucosamine (GlcNAc) moieties, wherein yy=1, 2, 3 or 4, with a compound of the formula $S(F)_{xx}$—P in the presence of a catalyst, wherein $S(F)_{xx}$ is a sugar derivative comprising xx reactive groups F capable of reacting with a functional group Q, xx is 1 or 2 and P is a nucleoside mono- or diphosphate, and wherein the catalyst is capable of transferring the $S(F)_{xx}$ moiety to the core-GlcNAc moiety, to obtain a modified antibody according to Formula (26):

(26)

wherein
AB is an antibody capable of targeting Trop-2-expressing tumours;
Fuc is fucose;
w is 0 or 1; and (ii) reacting the modified antibody with a compound according to general structure (1):

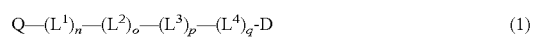

Q—(L$^1$)$_n$—(L$^2$)$_o$—(L$^3$)$_p$—(L$^4$)$_q$-D  (1)

wherein:
Q is a reactive moiety capable of reacting with F;
D is selected from the group consisting of taxanes, anthracyclines, camptothecins, epothilones, mytomycins, combretastatins, vinca alkaloids, maytansinoids, enediynes such as calicheamicins, duocarmycins, tubulysins, amatoxins, dolastatins and auristatins, pyrrolobenzodiazepine dimers, indolino-benzodiazepine dimers, radioisotopes, therapeutic proteins and peptides (or fragments thereof), kinase inhibitors, MEK inhibitors, KSP inhibitors, and analogues or prodrugs thereof;
L$^1$, L$^2$, L$^3$ and L$^4$ are each individually linkers that together link Q to D;
n, o, p and q are each individually 0 or 1, provided that n+o+p+q=1, 2, 3 or 4;

to obtain the antibody-conjugate,

Preferably, increasing the therapeutic index of an antibody-conjugate is selected from:
(a) increasing the therapeutic efficacy of the antibody-conjugate; and/or
(b) increasing the tolerability of the antibody-conjugate.

Increase in therapeutic efficacy of the antibody-conjugates according to the invention may take the form of a reduction in tumour size and/or a prolonged period of regression, when compared to conventional Trop-2 targeting ADC. Increase in tolerability of the antibody-conjugates according to the invention may take the form of a reduction in signs of toxicity, compared to administration of a Trop-2 targeting ADC made with a conventional technology. The reduction in sings may also be referred to as a reduction in symptoms or side-effects of cancer treatment, and may involve one or more clinical signs such as reduced reduction in body weight, reduced reduction in mobility, reduced reduction in food intake and/or one or more toxicity parameters, such as improved blood chemistry, hematology, and/or histopathology.

EXAMPLES

Figure 1:
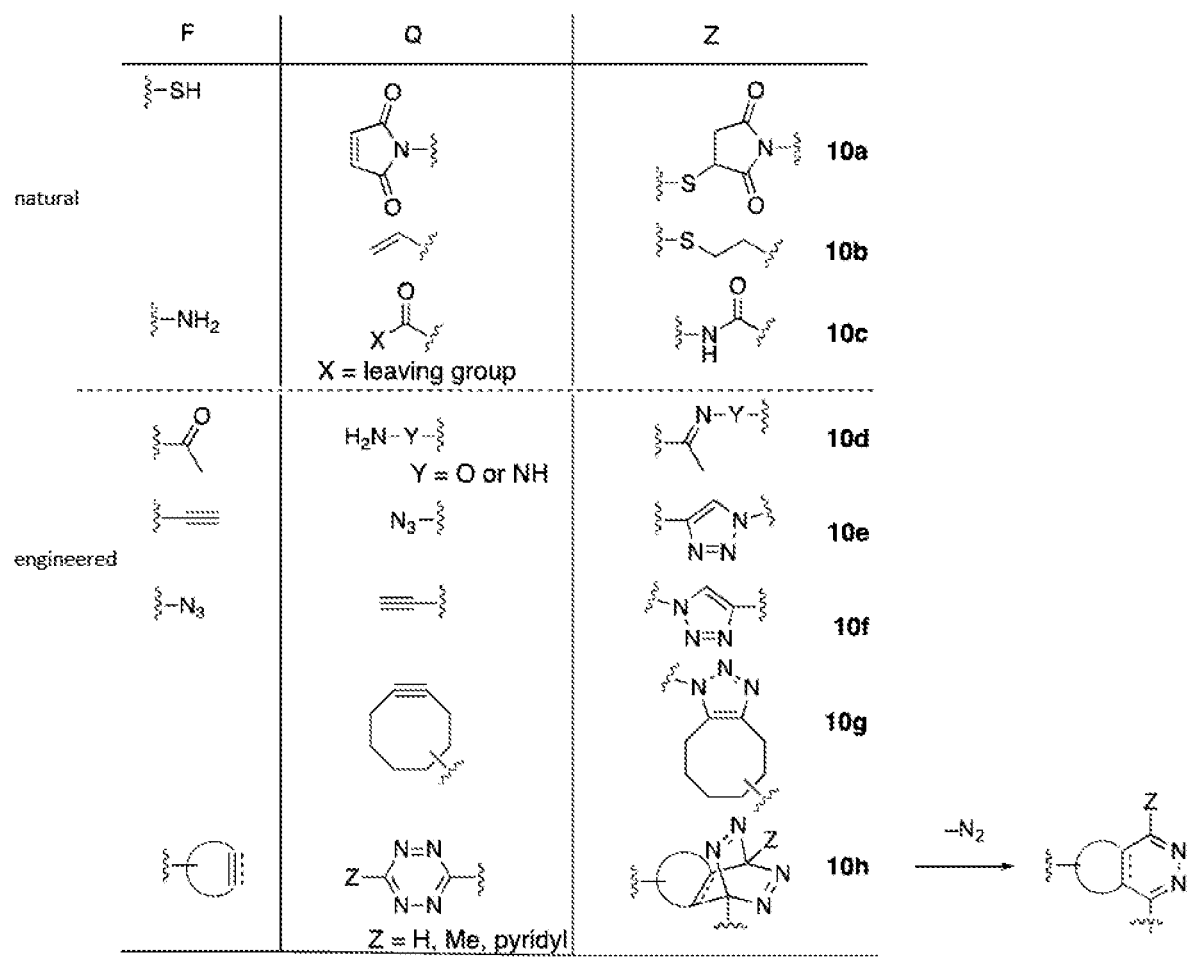
FIG. 1 shows a representative set of functional groups (F) that when present in a biomolecule lead to connecting group Z upon reaction with reactive group Q. Functional groups F can be naturally present of may be artificially introduced (engineered) into a biomolecule at any position of choice.
Figure 2:
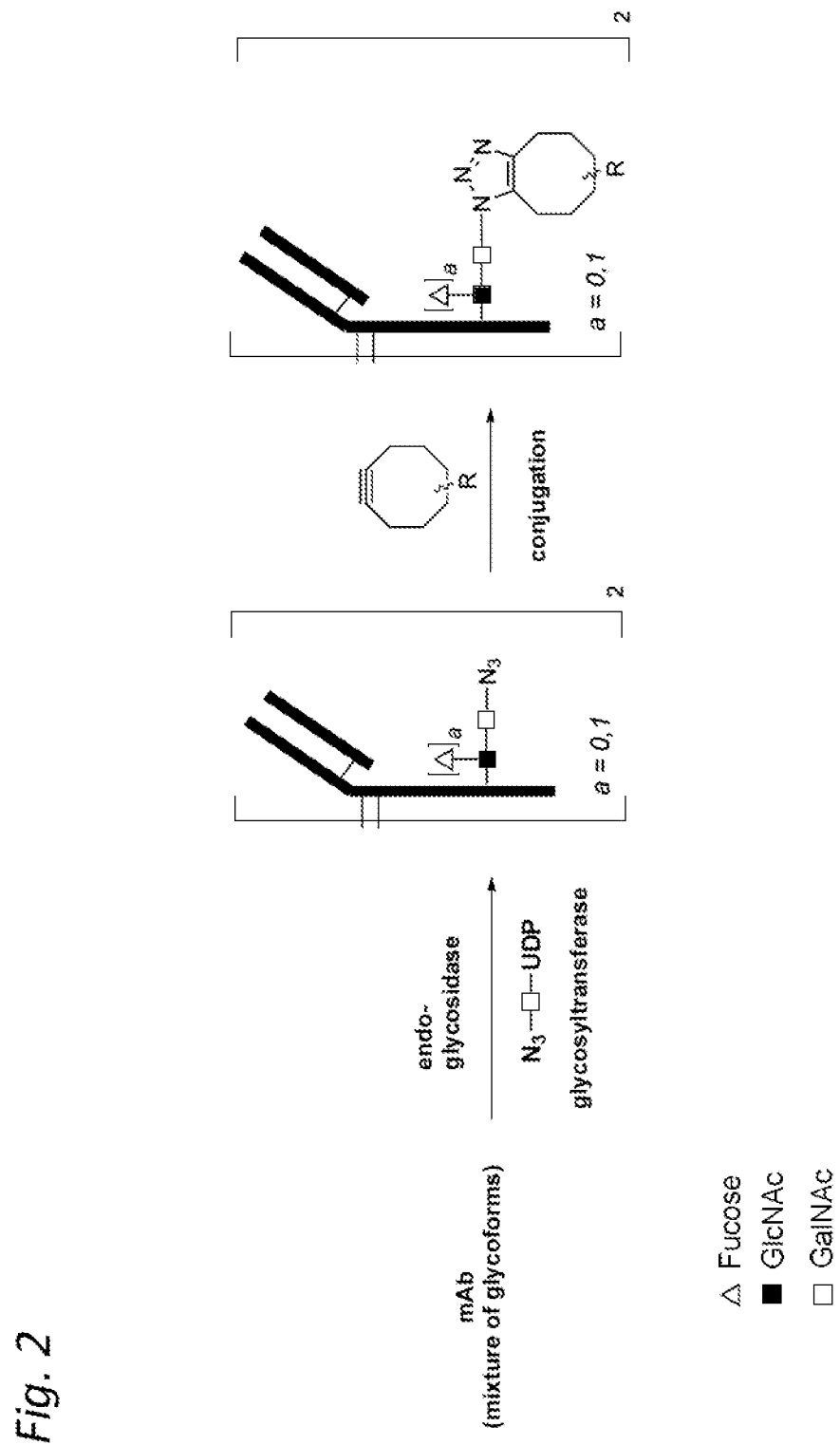
FIG. 2 schematically displays how an antibody conjugate can be obtained from any monoclonal antibody in a two-stage process. In the first stage, an azido-modified UDP-GalNAc may be attached to the monoclonal antibody in a one pot process involving (a) trimming of the glycan by an endoglycosidase (to the core GlcNAc) and (b) attachment of the azido-sugar under the action of a glycosyltransferase (a galactosyltransferase mutant or a GalNAc-transferase), thereby generating a β-glycosidic 1-4 linkage between the azido-modified GalNAc and GlcNAc. In the second stage, the azido-modified antibody is reacted with an appropriately functionalized cyclooctyne, thereby generating the antibody conjugate.

General procedure for transient expression and purification of monoclonal antibodies: Various IgGs (Huk-5-70-2, hTINA or hRS7) were transiently expressed in CHO K1 cells by Evitria (Zurich, Switzerland) at 100 mL scale. The supernatant was purified using a HiTrap MabSelect sure 5 mL column. The supernatant was loaded onto the column followed by washing with at least 10 column volumes of 25 mM Tris pH 7.5, 150 mM NaCl (TBS). Retained protein was eluted with 0.1 M Glycine pH 2.7. The eluted product was immediately neutralized with 1.5 M Tris-HCl pH 8.8 and dialyzed against TBS. Next the IgG was concentrated (15-20 mg/mL) using a Vivaspin Turbo 15 ultrafiltration unit (Sartorius). The sequences of the IgGs is given here below:

Huk5-70-2 (I) light chain:
(SEQ ID NO: 1)
EIVLTQSPATLSLSPGERATLSCRASQSIGTSIHWYQQKPGQAPRLLIKY

ASESISGIPARFSGSGSGTDFTLTISSLEPEDFAVYYCQQSNSWPFTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Huk5-70-2 (I) heavy chain:
(SEQ ID NO: 2)
QVQLVQSGAEVKKPGASVKVSCKASGYTFTIYWINWVRQAPGQGLEWIGN

IYPSDSYTNYNQKFKDKATLTVDTSASTAYMELSSLRSEDTAVYYCTRTS

MADYWGQGTLVTVSSASTKGPSVFPLAPSSKSTSGGTAALGCLVKDYFPE

PVTVSWNSGALTSGVHTFPAVLQSSGIYSLSSVVTVPSSSLGTQTYICNV

NHKPSNTKVDKRVEPKSCDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDG

SFFLYSKLTVDKSRWQQGNVFSCSVMHEALHNHYTQKSLSLSPGK hRS7 (II) light chain:
(SEQ ID NO: 3)
DIQLTQSPSSLSASVGDRVSITCKASQDVSIAVAWYQQKPGKAPKLLIYS

ASYRYTGVPDRFSGSGSGTDFTLTISSLQPEDFAVYYCQQHYITPLTFGA

GTKVEIKRTVAAPSVFIFPPSDEQLKSGTASVVCLLNNFYPREAKVQWKV

-continued

DNALQSGNSQESVTEQDSKDSTYSLSSTLTLSKADYEKHKVYACEVTHQG

LSSPVTKSFNRGEC hRS7 (II) heavy chain:
(SEQ ID NO: 4)
QVQLQQSGSELKKPGASVKVSCKASGYTFTNYGMNWVKQAPGQGLKWMGW

INTYTGEPTYTDDFKGRFAFSLDTSVSTAYLQISSLKADDTAVYFCARGG

FGSSYWYFDVWGQGSLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKRVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K hTINA (III) light chain:
(SEQ ID NO: 5)
DIQMTQSPSSLSASVGDRVTITCKASQDVSTAVAWYQQKPGKAPKLLIYS

ASYRYTGVPSRFSGSGSGTDFTLTISSLQPEDFAVYYCQQHYITPLTFGQ

GTKLEIKRTVAAPSVFIFPPSDEQLKSGTASVVCLLNNFYPREAKVQVVK

VDNALQSGNSQESVTEQDSKDSTYSLSSTLTLSKADYEKHKVYACEVTHQ

GLSSPVTKSFNRGEC hTINA (III) heavy chain:
(SEQ ID NO: 6)
QVQLVQSGAEVKKPGASVKVSCKASGYTFTTAGMQWVRQAPGQGLEWMGW

INTHSGVPKYAEDFKGRVTISADTSTSTAYLQLSSLKSEDTAVYYCARSG

FGSSYWYFDVWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKRVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K

General procedure for RP-HPLC analysis of (modified) monoclonal antibodies (reduced): Prior to RP-HPLC analysis samples were reduced by incubating a solution of 10 μg (modified) IgG for 15 minutes at 37° C. with 10 mM DTT and 100 mM Tris pH 8.0 in a total volume of 50 μL. A solution of 49% ACN, 49% MQ and 2% formic acid (50 μL) was added to the reduced sample. Reverse phase HPLC was performed on a Agilent 1100 HPLC using a ZORBAX Phoroshell 300SB-C8 1×75 5 μm (Agilent Technologies) column run at 1 ml/min at 70° C. using a 16.9 minute linear gradient from 25 to 50% buffer B (with buffer A=90% MQ, 10% ACN, 0.1% TFA and buffer B=90% ACN, 10% MQ, 0.1% TFA).

General procedure for mass spectral analysis of (modified) monoclonal antibodies: Prior to mass spectral analysis, IgG was treated with IdeS, which allows analysis of the Fc/2 fragment. For analysis of both light and heavy chain, a solution of 20 μg (modified) IgG was incubated for 5 minutes at 37° C. with 100 mM DTT in a total volume of 4 μL. If present, azide-functionalities are reduced to amines under these conditions. For analysis of the Fc/2 fragment, a solution of 20 μg (modified) IgG was incubated for 1 hour at 37° C. with IdeS/Fabricator™ (1.25 U/μL) in phosphate-buffered saline (PBS) pH 6.6 in a total volume of 10 μL. Samples were diluted to 80 μL followed by analysis electrospray ionization time-of-flight (ESI-TOF) on a JEOL AccuTOF. Deconvoluted spectra were obtained using Magtran software.

Figure 3:
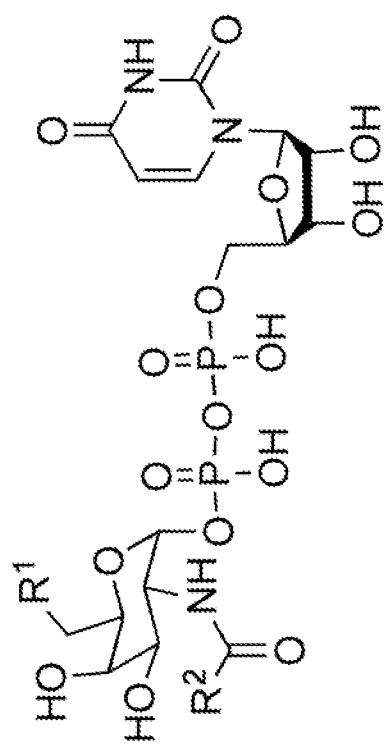
FIG. 3 shows several structures of derivatives of UDP sugars of galactosamine, which may be modified with e.g. a 3-mercaptopropionyl group (11a), an azidoacetyl group (11b), or an azidodifluoroacetyl group (11c) at the 2-position, or with an azido group at the 6-position of N-acetyl galactosamine (11d).
Figure 4:
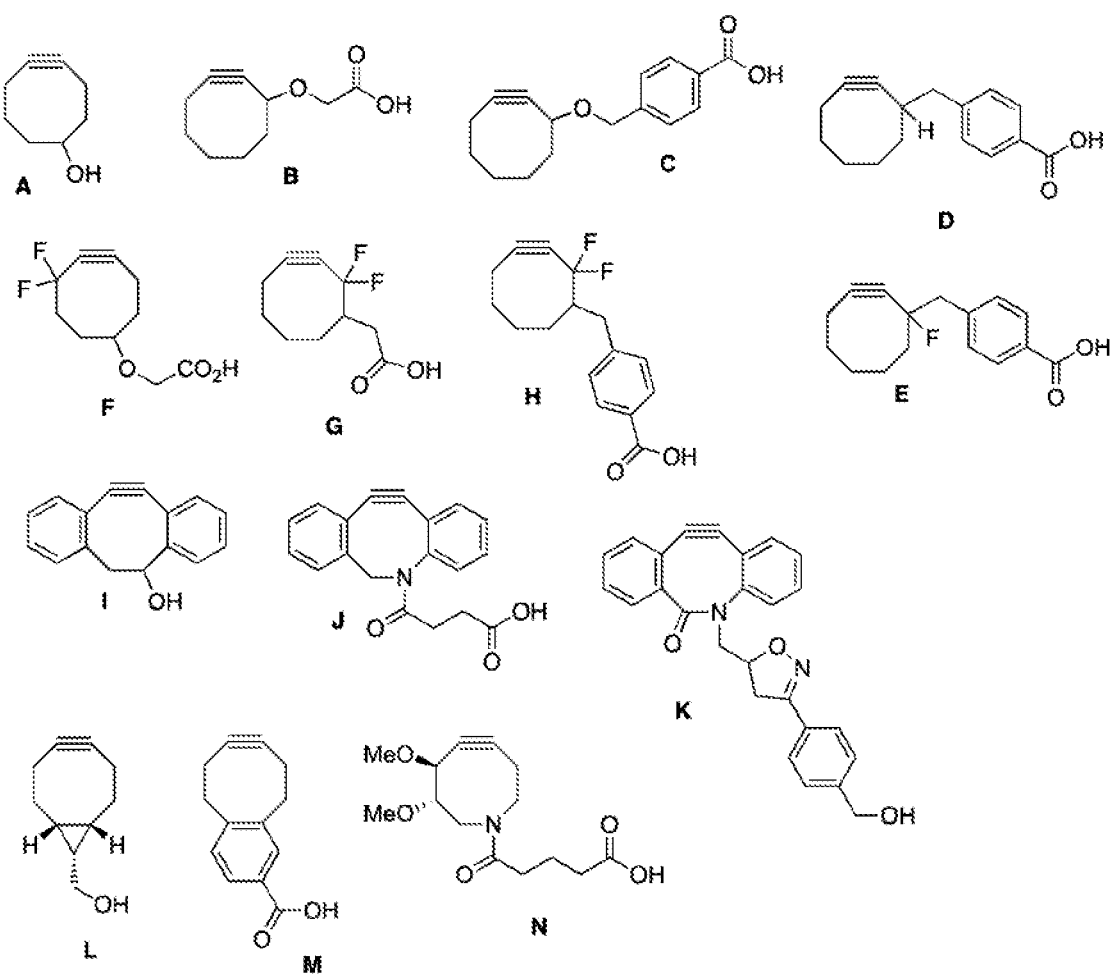
FIG. 4 shows cyclooctynes suitable for metal-free click chemistry.

General procedure for enzymatic remodeling of IgG to mAb-(6-$N_3$-GalNAc)$_2$: IgG (15 mg/mL) was incubated with 1% w/w EndoSH (as described in PCT/EP2017/052792, see Examples 1-3, and SEQ. ID No: 1, which is incorporated by reference herein), 7.5% w/w His-TnGalNAcT (as described in PCT/EP2016/059194, see Examples 3 and 4, and SEQ. ID No: 49, which is incorporated by reference herein) and UDP 6-$N_3$-GalNAc (compound 11d in FIG. 3, commercially available from Glycohub, Inc.) (25 eq compared to IgG) in 10 mM $MnCl_2$ and TBS for 16 hours at 30° C. Next, the functionalized IgG was purified using a HiTrap MabSelect sure 5 mL column. After loading of the reaction mixture the column was washed with TBS+0.2% triton and TBS. The IgG was eluted with 0.1 M glycine-HCl pH 2.7 and neutralized with 1 M Tris-HCl pH 8.8. After three times dialysis to PBS the IgG was concentrated to 15-20 mg/mL using a Vivaspin Turbo 15 ultrafiltration unit (Sartorius).

Preparation of Azide-Functionalized Antibodies: Examples 1-3

Example 1: Preparation of Huk5-70-2-(6-$N_3$-GalNAc)$_2$ (I-$N_3$)

According to the general procedure for enzymatic remodeling, Huk5-70-2 was converted to Huk5-70-2-(6-$N_3$-GalNAc)$_2$ Mass spectral analysis of a sample after IdeS treatment showed one major Fc/2 product (observed mass 24364 Da, approximately 90% of total Fc/2), corresponding to the expected product.

Example 2: Preparation of hRS7-(6-$N_3$-GalNAc)$_2$ (II-$N_3$)

According to the general procedure for enzymatic remodeling, hRS7 was converted to hRS7-(6-$N_3$-GalNAc)$_2$ Mass spectral analysis of a sample after IdeS treatment showed one major Fc/2 product (observed mass 24364 Da, approximately 90% of total Fc/2), corresponding to the expected product.

Example 3: Preparation of hTINA-(6-$N_3$-GalNAc)$_2$ (III-$N_3$)

According to the general procedure for enzymatic remodeling, hTINA was converted to hTINA-(6-$N_3$-GalNAc)$_2$ Mass spectral analysis of a sample after IdeS treatment showed one major Fc/2 product (observed mass 24366 Da, approximately 90% of total Fc/2), corresponding to the expected product.

Examples 4-7: Synthesis of BCN-Linker Constructs 22 and 25

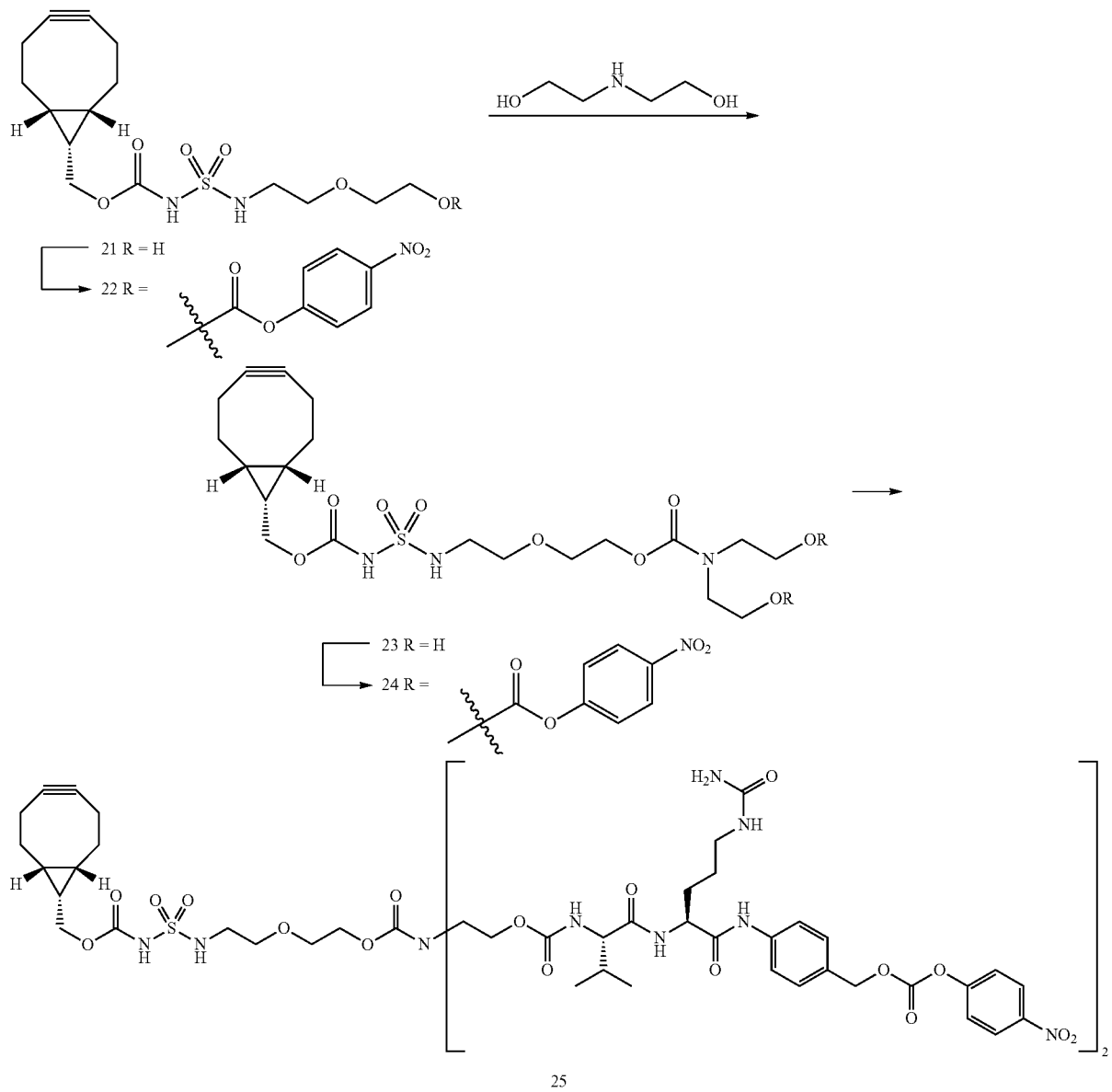

Example 4: Preparation of 22

Compound 22 was prepared via activation of compound 21 (prepared according to Example 50 of PCT/NL2015/050697, incorporated herein). To a solution of 21 (229 mg, 0.64 mmol) in DCM (20 mL) were added p-nitrophenyl chloroformate (128 mg, 0.64 mmol) and Et$_3$N (268 μL, 194 mg, 1.92 mmol). The mixture was stirred overnight at rt and subsequently concentrated under reduced pressure. The residue was purified via gradient column chromatography (20→70% EtOAc in heptane (1% AcOH) to afford the PNP carbonate derivative of 22 as a white solid (206 mg, 0.39 mmol, 61%). $^1$H NMR (400 MHz, CDCl$_3$) δ (ppm) 8.31-8.26 (m, 2H), 7.45-7.40 (m, 2H), 5.56 (t, J=6.0 Hz, 1H), 4.48-4.40 (m, 2H), 4.27 (d, J=8.2 Hz, 2H), 3.81-3.75 (m, 2H), 3.68 (t, J=5.0 Hz, 2H), 3.38-3.30 (m, 2H), 2.36-2.14 (m, 6H), 1.61-1.45 (m, 2H), 1.38 (quintet, J=8.7 Hz, 1H), 1.04-0.94 (m, 2H).

Compound 24 was prepared from compound 22 according to examples 23 and 24 of PCT/EP2017/052790, incorporated herein.

Example 5: Preparation of 23

To solution of compound 22 (0.39 g; 0.734 mmol) in DCM (30 mL) were added a solution of diethanolamine (DEA, 107 mg; 1.02 mmol) in DMF (2 mL) and Et$_3$N (305 μL; 221 mg; 2.19 mmol). The resulting mixture was stirred at rt for 17 h and washed with a saturated aqueous solution of NH$_4$Cl (30 mL). The aqueous phase was extracted with DCM (30 mL) and the combined organic layers were dried (Na$_2$SO$_4$) and concentrated. The residue was purified by flash column chromatography (DCM→MeOH/DCM 1/9). The product 23 was obtained as a colourless film (163 mg; 0.33 mmol; 45%). $^1$H NMR (400 MHz, CDCl$_3$) δ (ppm) 6.29 (bs, 1H), 4.33-4.29 (m, 2H), 4.28 (d, J=8.2 Hz, 2H), 3.90-3.80 (m, 4H), 3.69-3.64 (m, 2H), 3.61 (t, J=4.8 Hz, 2H), 3.52 (t, J=5.0 Hz, 4H), 3.32 (t, J=5.1 Hz, 2H), 2.37-2.18 (m, 6H), 1.60-1.55 (m, 2H), 1.39 (quintet, J=8.7 Hz, 1H), 1.05-0.94 (m, 2H).

Example 6: Preparation of 24

To a solution of 23 (163 mg, 0.33 mmol) and 4-nitrophenyl chloroformate (134 mg, 0.66 mmol) in DCM (10 mL) was added Et$_3$N (230 μL; 167 mg; 1.65 mmol). The reaction mixture was stirred for 17 h and concentrated. The residue was purified by flash column chromatography (50% EtOAc in heptane→100% EtOAc). The product 24 was obtained as a colourless oil (69 mg; 0.084 mmol; 25%). $^1$H NMR (400 MHz, CDCl$_3$) δ (ppm) 8.29-8.23 (m, 4H), 7.42-7.35 (m, 4H), 5.81-5.71 (m, 1H), 4.53-4.43 (m, 4H), 4.36-4.30 (m, 2H), 4.25 (d, J=8.2 Hz, 2H), 3.81-3.70 (m, 4H), 3.70-3.65 (m, 2H), 3.62-3.56 (m, 2H), 3.32-3.24 (m, 2H), 2.34-2.14 (m, 6H), 1.60-1.45 (m, 2H), 1.35 (quintet, J=8.7 Hz, 1H), 1.02-0.91 (m, 2H).

Example 7: Preparation of 25

To a solution of 24 (62 mg, 75 μmol) in DMF (0.5 mL) were added vc-PAB-OH (60 mg, 0.16 mmol) and Et$_3$N (63 μL, 46 mg, 0.45 mmol). The mixture was left standing for 3.5 h and bis-(4-nitrophenyl) carbonate (137 mg, 0.45 mmol), Et$_3$N (63 μL, 46 mg, 0.45 mmol) and DMF (0.5 mL) were added. After 75 min, the mixture was concentrated. The residue was purified with silica gel chromatography (DCM to 15% MeOH in DCM). The desired product was obtained as a white solid (86 mg, 52.7 μmol, 70%). LCMS (ESI+) calculated for $C_{72}H_{94}N_{15}O_{27}S^+$ (M+H$^+$) 1632.62, found 1632.7. $^1$H NMR (400 MHz, DMSO-d6) δ (ppm) 10.15-10.04 (m, 2H), 8.34-8.28 (m, 4H), 8.20-8.08 (m, 2H), 7.68-7.61 (m, 4H), 7.59-7.54 (m, 4H), 7.44-7.38 (m, 4H), 7.29-7.21 (m, 1H), 7.21-7.14 (m, 1H), 6.06-5.97 (bs, 2H), 5.49-5.39 (bs, 4H), 5.27-5.20 (bs, 4H), 4.45-4.36 (m, 2H), 4.18 (m, 10H), 3.60-3.28 (m, 5H), 3.10-2.88 (m, 5H), 2.28 (m, 6H), 2.03-1.91 (m, 2H), 1.80-1.20 (m, 13H), 0.91-0.78 (m, 6H).

Figure 5:
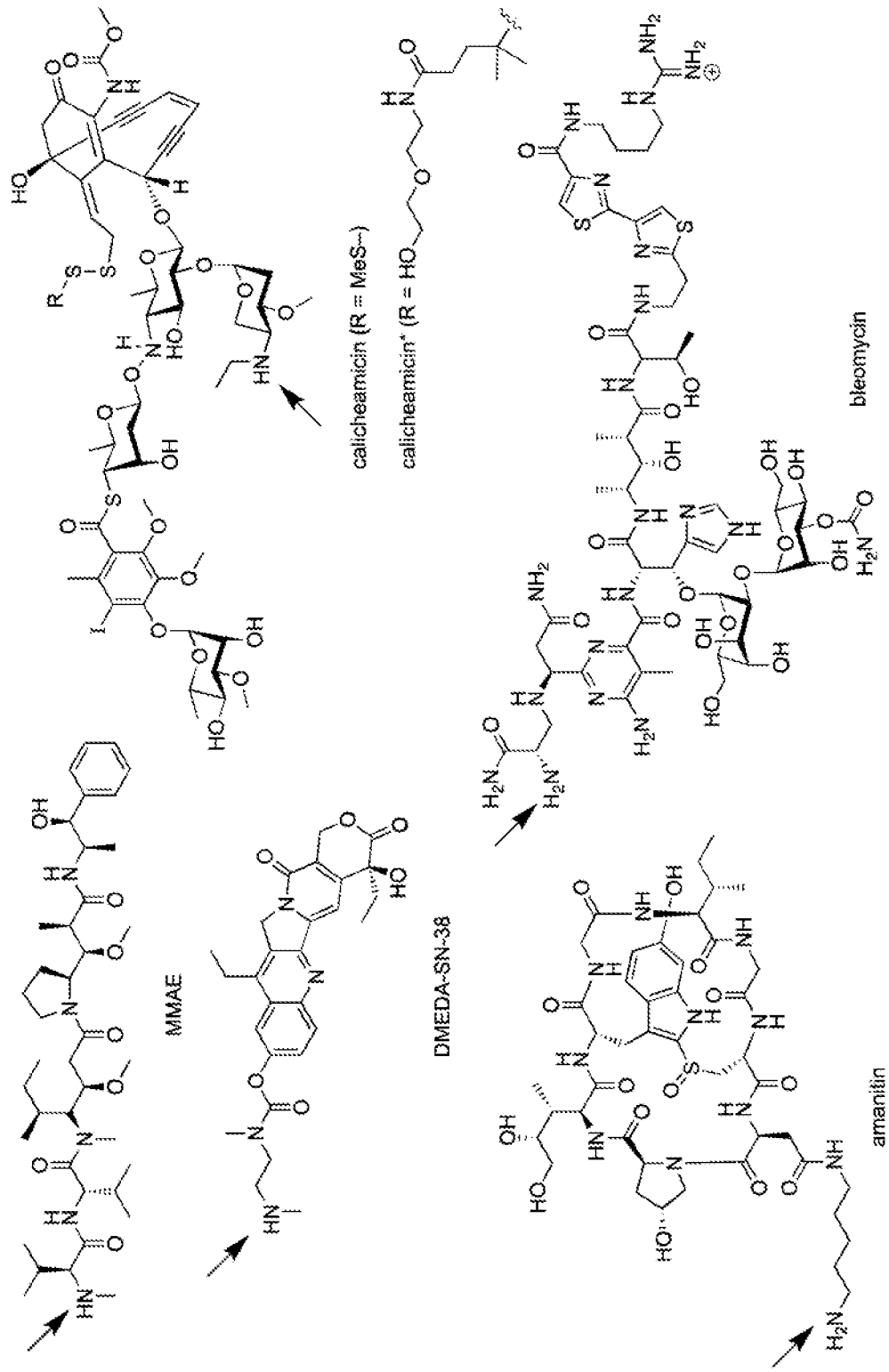
FIG. 5 shows a set of toxic payloads that were conjugated to various Trop-2-targeting monoclonal antibodies according to the invention. Point of attachment of a linker (to an amino group present in the payload) is indicated with an arrow.

Compound 24 or 25 was reacted with an amino group, naturally present or installed (via a linker) onto toxic payloads MMAE, SN-38, amanitin or bleomycin (see FIG. 5 for structures of payloads and attachment point).

Examples 8-15: Synthesis of Linker-Payloads 41-44

Example 8: Preparation of Linker-Conjugate 41

The synthesis of BCN-HS-(vc-PABC-MMAE)$_2$ (41) is also described in PCT/EP2017/052791 (example 25), incorporated herein. To a solution of 24 (27 mg, 33 μmol) in DMF (400 μL) were added triethylamine (22 μL; 16 mg; 158 μmol) and a solution of vc-PABC-MMAE.TFA (96 mg; 78 μmol) in DMF (1.0 mL). The mixture was left standing for 19 h and 2,2'-(ethylenedioxy)bis(ethylamine) (37 μL, 38 mg, 253 μmol) was added. After 2 h, the reaction mixture was diluted with DMF (100 μL) and purified by RP HPLC (C18, 30%→90% MeCN (1% AcOH) in water (1% AcOH). The desired product 41 was obtained as a colourless film (41 mg, 14.7 μmol, 45%). LCMS (ESI$^+$) calculated for $C_{138}H_{219}N_{23}O_{35}S^{2+}$ (M+2H$^+$) 1395.79 found 1396.31.

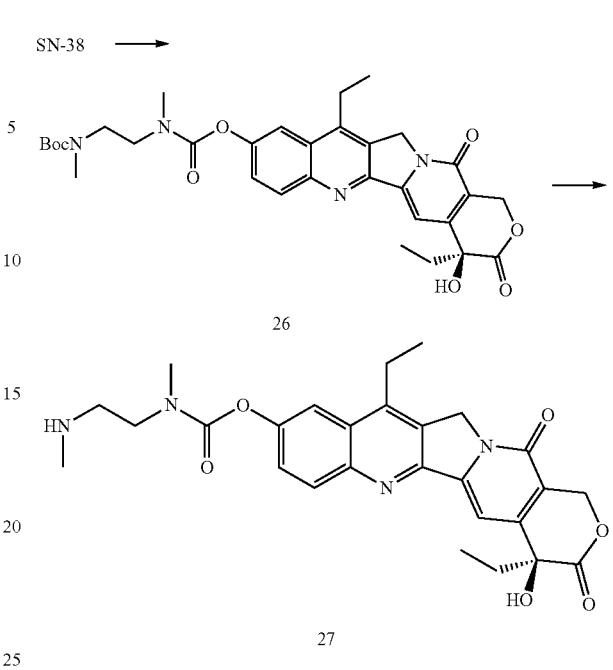

26

27

Example 9: Synthesis of 26

To a solution of 7-ethyl-10-hydroxycamptothecin (SN-38, 55 mg, 0.14 mmol) in DMF (10 mL) were added 4-nitrophenyl chloroformate (28 mg, 0.14 mmol) and Et$_3$N (59 μL, 42 mg, 0.42 mmol). The mixture was stirred for 1.5 h and Et$_3$N (59 μL, 42 mg, 0.42 mmol) was added. The mixture was stirred for 25 min and 4-nitrophenyl chloroformate (28 mg, 0.14 mmol) was added. The mixture was stirred for 20 min and a solution of tert-butyl methyl[2-(methylamino)ethyl]carbamate (79 mg, 0.42 mmol) in DMF (0.89 mmoL) was added. The mixture was stirred for 1 h. and water (20 mL) was added. The reaction mixture was extracted with EtOAc (20 mL). The organic phase was washed with water (2×20 mL), dried (Na$_2$SO$_4$) and concentrated. The residue was purified with silica gel chromatography (DCM to 10% MeOH in DCM). The desired product (25 mg, 41 μmol, 30%) was obtained as a slightly yellow film. LCMS (ESI+) calculated for $C_{32}H_{39}N_4O_8$+(M+H$^+$) 607.28, found 607.6.

Example 10: Synthesis of 27

To a solution of 26 (20 mg, 33 μmol) in DCM (0.8 mL) was added TFA (0.2 mL). The mixture was left standing for 20 min and concentrated. To the residue was added DCM (1 mL) and toluene (1 mL). The mixture was concentrated and the residue was used crude in the next step.

Example 11: Synthesis of Linker Conjugate 42

To a solution of 25 (5.4 mg, 3.3 μmol) in DMF (50 μL) were added Et$_3$N (9.2 μL, 6.7 mg, 66 μmol), a solution of 27 (20 mg, 33 μmol) in DMF (0.1 mL) and DMF (100 μL). The mixture was left standing for 50 min and additional Et$_3$N (9.2 μL, 6.7 mg, 66 μmol) was added. After 85 min, the reaction mixture was purified by RP-HPLC (C18, 30%→90% MeCN (1% AcOH) in water (1% AcOH) and subsequently silica gel chromatography (DCM to 20% MeOH in DCM), which yielded 6.7 mg (2.8 μmol, 85%) of the desired product 42. LCMS (ESI+) calculated for $C_{114}H_{145}N_{21}O_{33}S^{2+}$ (M+2H$^+$)/2 1184.50, found 1184.7.

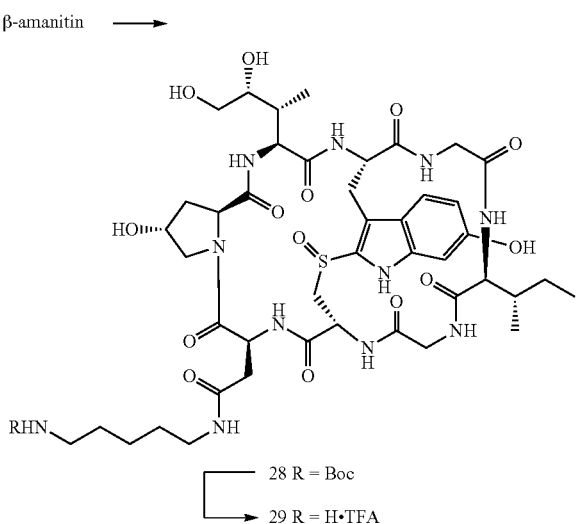

Example 12: Synthesis of 28

To a solution of β-amanitin (8.5 mg, 9.2 μmol) in DMF (189 μL) were added N-Boc-cadaverine (5.8 μL, 5.6 mg, 27.7 μmol), Et$_3$N (3.9 μL, 2.8 mg, 27.7 μmol) and a solution of BOP (25 mg, 55.4 μmol) in DMF (205 μL). The mixture was left standing for 17 h, diluted with DMF (100 μL) and purified by RP-HPLC (C18, 5%→90% MeCN (1% AcOH) in water (1% AcOH). The desired product was obtained a slightly yellow film (3.4 mg, 3.1 μmol, 33%). LCMS (ESI+) calculated for $C_{49}H_{74}N_{11}O_{16}S^+$ (M+H$^+$) 1104.50, found 1104.67.

Example 13: Synthesis of 29

A solution of 28 in TFA (0.5 mL) was left standing for 2 min and concentrated at r.t. The residue was taken up in MeCN and concentrated (2×). The residue was purified by RP-HPLC (C18, 5%→90% MeOH (0.05% TFA) in water (0.05% TFA), which yielded 2.7 mg (2.7 μmol, 77%) of the desired product. LCMS (ESI+) calculated for $C_{44}H_{66}N_{11}O_{14}S^+$ (M+H$^+$) 1004.45, found 1004.59.

Example 14: Synthesis of Linker Conjugate 43

To a solution of 29 (2.7 mg, 2.4 umol) in DMF (270 μL) was added a 10% solution of Et$_3$N in DMF (7.5 μL) and a solution of 25 (1.5 mg, 0.9 mmol) in DMF (9.0 μL). The mixture was left standing for 17 h and Et$_3$N (1.5 μL, 1.1 mg, 11 μmol). After 5.5 h, the mixture was purified by RP-HPLC (C18, 30%→90% MeCN (1% AcOH) in water (1% AcOH). The desired product was obtained as a white film (0.8 mg, 0.24 μmol, 26%). LCMS (ESI+) calculated for $C_{148}H_{215}N_{35}O_{49}S_{32}^+$ (M+2H$^+$)/2 1681.73, found 1682.00.

Example 15: Synthesis of Linker Conjugate 44

To a solution of 25 (1.6 mg, 1 μmol) in DMF (78 μL) were added Et$_3$N (0.68 μL; 0.5 mg; 5 μmol) and a solution of bleomycin B (3 mg; 2 μmol) in DMF (120 μL). The mixture was left standing for 40 h and an extra amount of bleomycin B (0.5 mg; 0.33 μmol) in DMF (20 μL) was added. After 4 h, the reaction mixture was diluted with DMF (700 μL) and purified by RP-HPLC (C18, 5%→95% MeCN (1% AcOH) in water (1% AcOH). The desired product 44 was obtained as a colorless film (2.6 mg, 0.6 μmol, 62%). LCMS (ESI+) calculated for $C_{170}H_{249}N_{51}O_{65}S_5^{6+}$ (M+6H$^+$) 701.7 found 701.2.

Examples 16-18: Synthesis of BCN-Linker Construct 32

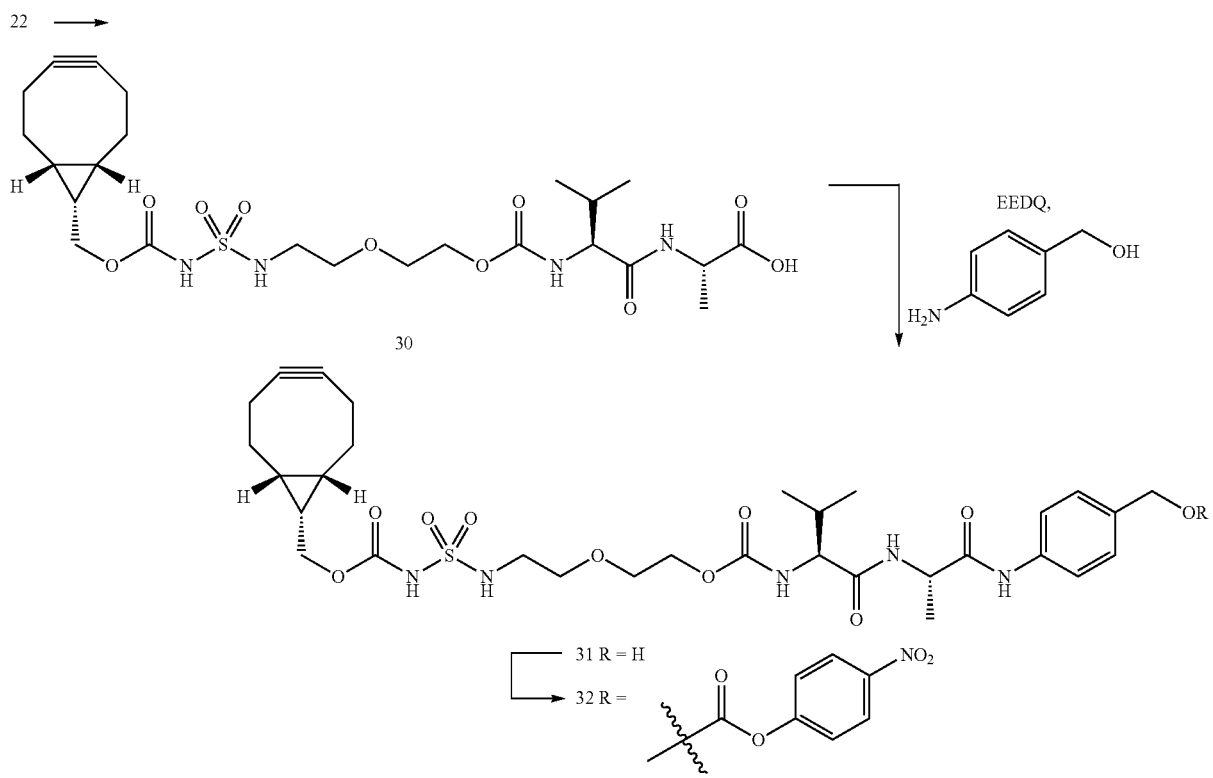

To a suspension of H-Val-Ala-OH (98 mg, 0.52 mmol) in DMF (2 mL) were added a solution of 22 (137 mg, 0.261 mmol) in DMF (2 mL) and Et$_3$N (182 μL, 132 mg, 1.31 mmol). The resulting mixture was stirred for 18.5 h. DCM (20 mL) and H$_2$O (20 mL) were added and the pH of the aqueous layer was adjusted to pH 4 with an aqueous solution of HCl (1N). After separation, the aqueous layer was extracted with DCM (20 mL). The combined organic layers were dried (Na$_2$SO$_4$) and concentrated. The residue was purified with silica gel chromatography (MeOH in DCM 0 to 20%). The product 30 was obtained as a colourless oil (113 mg, 0.20 mmol, 75%) 1H NMR (400 MHz, CDCl$_3$) δ (ppm) 4.58-4.38 (m, 1H), 4.28 (d, 2H, J=8.5 Hz), 4.12-3.98 (m, 2H), 3.75-3.60 (m, 4H), 3.40-3.25 (m, 2H), 2.36-2.16 (m, 6H), 1.63-1.49 (m, 2H), 1.47-1.35 (m, 4H), 1.06-0.84 (m, 8H).

Example 17: Synthesis of 31

To a solution of 30 (70 mg, 0.12 mmol) in DMF (1 mL) were added EEDQ (36 mg, 0.15 mmol and 4-aminobenzyl alcohol (18 mg, 0.15 mmol). The mixture was stirred for 22 h, diluted with DCM (5 mL) and concentrated. The residue was purified with silica gel chromatography (MeOH in DCM 0 to 20%). The combined column fractions were concentrated, and the residue was co-evaporated with EtOAc (2×6 mL). The product, alcohol 31, was obtained as a white solid (32 mg, 0.047 mmol, 39%). 1H NMR (400 MHz, CDCl$_3$) δ (ppm) 8.84 (s, 0.3H), 8.79 (s, 0.7H), 7.58-7.42 (m, 2H), 7.28-7.16 (m, 2H), 6.40-6.32 (m, 0.3H), 6.24-6.14 (m, 0.7H)+, 6.09 (d, J=7.4 Hz, 0.3H), 5.94 (d, J=7.2 Hz, 0.7H), 4.74-4.63 (m, 1H), 4.59 (s, 2H), 4.40-3.90 (m, 5H), 3.70-3.45 (m, 4H), 3.29-3.14 (m, 2H), 2.34-2.06 (m, 6H), 1.57-1.30 (m, 6H), 1.01-0.88 (m, 8H).

Example 18: Synthesis of 32

To a solution of alcohol 31 (32 mg, 0.047 mmol) in DMF (0.5 mL) were added bis-(4-nitrophenyl) carbonate (14 mg, 0.047 mmol) and Et$_3$N (20 μL, 14 mg, 0.141 mmol). The mixture was stirred for 17.5 h, diluted with DCM (5 mL) and concentrated. The residue was purified with silica gel chromatography (MeOH in DCM 0 to 20%). The product 32 was obtained as a colourless oil (22 mg, 0.026 mmol, 55%) 1H NMR (400 MHz, CDCl$_3$) δ (ppm) 8.89 (s, 0.3H), 8.80 (s, 0.7H), 8.29-8.23 (m, 2H), 7.71-7.61 (m, 2H), 7.40-7.32 (m, 4H), 7.12-7.01 (m, 1H), 6.40-6.30 (m, 0.3H), 6.22-6.11 (m, 0.7H), 5.95-5.82 (m, 1H), 5.23 (s, 2H), 4.76-4.65 (m, 1H), 4.45-3.90 (m, 5H), 3.71-3.56 (m, 4H), 3.31-3.21 (m, 2H), 2.34-2.12 (m, 6H), 1.57-1.30 (m, 6H), 1.02-0.90 (m, 8H).

Examples 19-25: Synthesis of Linker-Conjugates 45 and 46

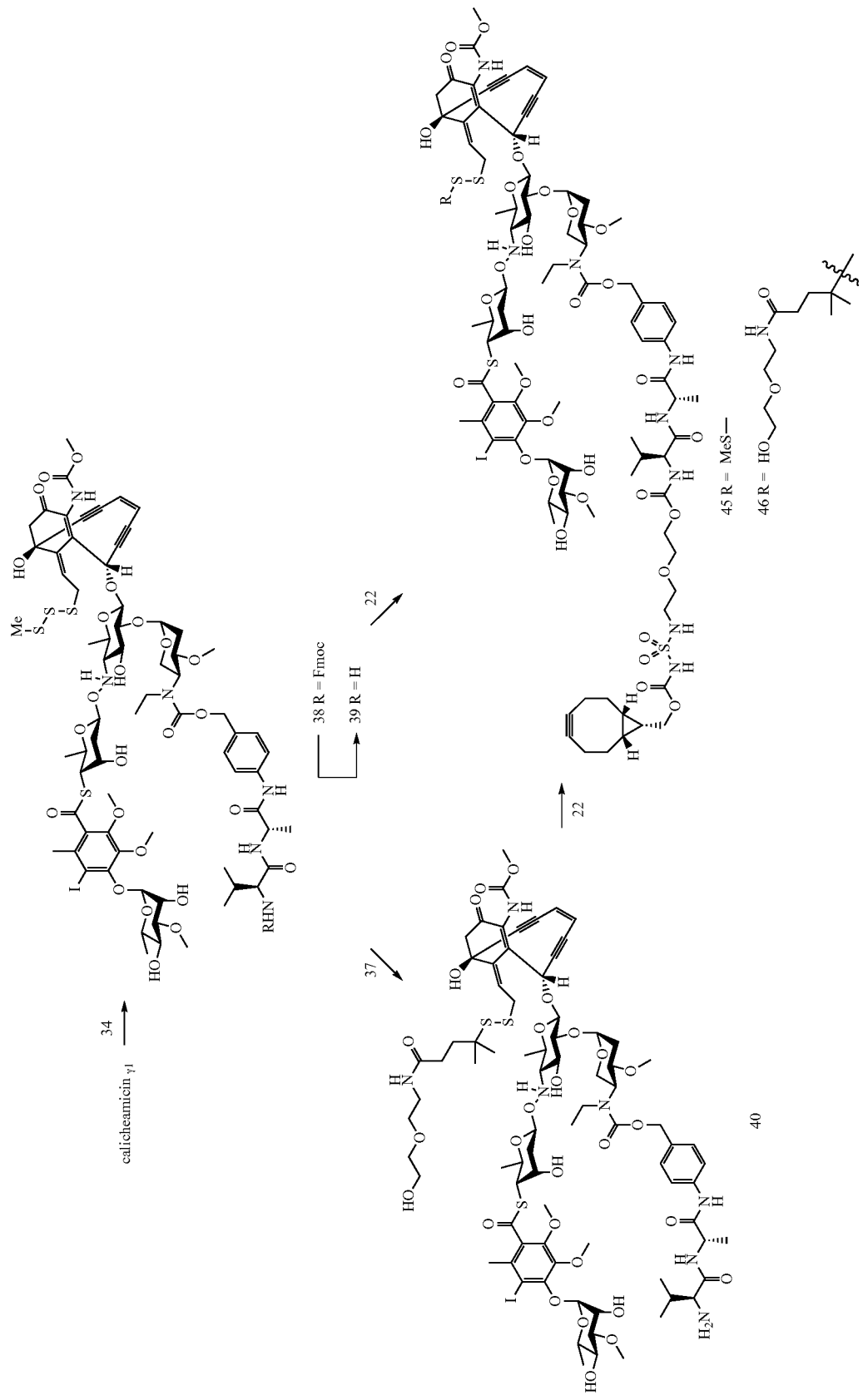

Example 19: Synthesis of 34
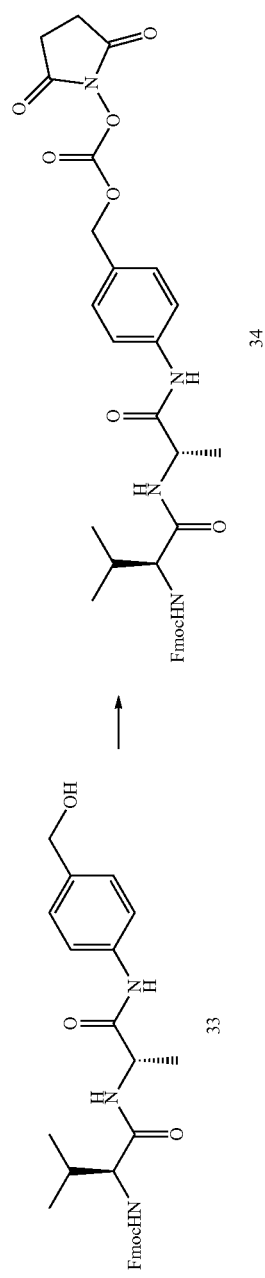

To a solution of 9-fluorenylmethyloxycarbonyl-valyl-alanyl-4-aminobenzylalcohol (33, 291 mg, 564 µmol, 1.0 equiv.) in DMF (2.0 mL) was added N,N'-disuccinimidyl carbonate (292 mg, 1.14 mmol, 2.02 equiv.). To the resulting yellow suspension was added DiPEA (198 µL, 1.20 mmol, 2.12 equiv.), generating a white suspension, which turned into a solution after a few minutes. The reaction mixture was stirred at room temperature for 50 minutes and then added portion wise to a stirred mixture of DCM (50 mL) and $H_2O$ (10 mL). The resulting suspension was filtered over a glass filter and the filtrate was then partially concentrated in vacuo to remove the DCM. Following the removal of DCM, $Et_2O$ (50 mL) was added to the mixture and the resulting biphasic system was filtered over the same glass filter used previously. The residue was washed with $Et_2O$ and then concentrated under high vacuum, affording 311 mg of a white solid. The solid was then suspended, ultrasonicated and decanted with $H_2O$ (2×), DCM (1×) and $Et_2O$ (2×) successively, affording the product 34 as a white solid (199 mg, ~76% pure (OMR), 230 µmol, 41%). LCMS (ESI+) calculated for $C_{36}H_{36}N_4NaO_9^+$ (M+Na+) 679.24, found 678.97. $^1$H NMR (400 MHz, DMSO-$d_6$) δ (ppm) 10.14 (s, 1H), 8.23 (d, J=6.8 Hz, 1H), 7.91 (d, J=7.6 Hz, 2H), 7.77 (t, J=6.8 Hz, 2H), 7.66 (d, J=8.4 Hz, 2H), 7.52-7.39 (m, 4H), 7.34 (t, J=7.6 Hz, 2H), 5.77 (s, 1H), 5.34 (s, 1H), 4.44 (m, 1H), 4.37-4.17 (m, 3H), 3.93 (t, J=8.8 Hz, 1H), 2.82 (bs, 3H), 2.06-1.94 (m, 1H), 1.33 (d, J=7.2 Hz, 3H), 0.89 (m, 6H).

Example 20: Synthesis of 37

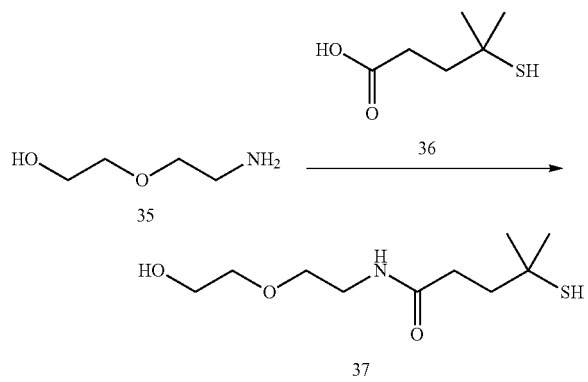

To a solution of 4-mercapto-4-methylpentanoic acid 36 (103 mg, 692 µmol) in dry DCM (3.0 mL) was added EDC.HCl (143 mg, 744 µmol), followed by DiPEA (0.228 mL, 1.38 mmol) and the reaction mixture was stirred for 10 minutes before the addition of amino-alcohol 35 (76.3 µL, 761 µmol). The reaction mixture was stirred for 19 hours and purified directly by silica gel column chromatography (0→8% MeOH in DCM), to give 37 (65.4 mg) as a colorless oil. $^1$H NMR (400 MHz, $CDCl_3$) δ (ppm) 6.13 (bs, 1H), 3.77 (t, J=4.4 Hz, 2H), 3.59 (q, J=4.8 Hz, 4H), 3.48 (q, J=5.2 Hz, 2H), 2.43-2.33 (m, 2H), 1.98-1.88 (m, 2H), 1.65 (s, 1H), 1.39 (s, 6H), LCMS (ESI+) calculated for $C_{10}H_{22}NO_3S^+$ (M+H$^+$) 236.13, found 236.13.

Example 21: Synthesis of 38

To a vial containing 34 (~76% pure, 69.3 mg, 80.2 µmol) was added a solution of calicheamicin $\gamma_1^I$ (23.8 mg, 17.4 µmol) in DMF (380 µL). The resulting solution was heated to 37° C. for 20 hours and then allowed to cool to room temperature. The reaction mixture was then diluted with DCM (4 mL) and purified by silica gel chromatography (0→8% MeOH in DCM). The fraction containing pure product were pooled, while the impure fractions were purified by a second silica gel chromatography purification (0→8% MeOH in DCM). The combination and concentration of the pure fractions from the first and second purification afforded the product as a white residue (23.6 mg, 12.4 µmol, 71%) LCMS (ESI+) calculated for $C_{86}H_{106}IN_6O_{27}S_4^+$ (M+H$^+$) 1909.50, found 1909.65.

Example 22: Synthesis of 39

To a solution of 38 (23.6 mg, 11.6 µmol) in a mixture of $THF:H_2O$ (25:1, 5.5 mL) was added diethylamine (1.1 mL). The resulting reaction mixture was left at room temperature for 65 minutes and then concentrated in vacuo and purified by silica gel chromatography (0→30% MeOH in DCM). The desired product 39 was obtained as a reddish film (10.6 mg, 6.28 µmol, 51%) LCMS (ESI+) calculated for $C_{71}H_{96}IN_6O_{25}S_4^+$ (M+H$^+$) 1687.43, found 1687.70.

Example 23: Synthesis of 40

A solution of 39 (10.6 mg, 6.28 µmol) in MeCN (2.0 mL) was cooled to −15° C. by using a brine/ice-bath. To the cooled solution was added a solution of 37 in MeCN (147.8 µL, 14.8 mg, 62.8 µmol), followed by the addition of neat $Et_3N$ (8.75 µL, 62.8 µmol). The resulting reaction mixture was left in the ice-bath for 50 minutes and then allowed to warm to room temperature. The reaction mixture was left at room temperature for 75 minutes and then conc. in vacuo and purified by RP-HPLC (C18, 5%→90% MeCN (1% AcOH) in water (1% AcOH). The desired product 40 was obtained as a yellow oil (9.1 mg, 4.93 µmol, 79%) LCMS (ESI+) calculated for $C_{80}H_{113}IN_7O_{28}S_3^+$ (M+H$^+$) 1842.58, found 1842.80.

Example 24: Synthesis of Linker Conjugate 45

To a solution of 39 (7.29 mg, 4.31 µmol, 1.0 equiv.) in DMF (185 µL) were added a solution of 22 (3.75 mg, 7.13 µmol, 1.65 equiv.) in DMF (16.4 µL) and $Et_3N$ (1.81 µL, 13.0 µmol, 3.0 equiv.). The mixture was mixed thoroughly and left standing for 0.5 h and then additional 22 (2.28 mg, 4.34 µmol, 1.0 equiv.) in DMF (10.0 µL) was added. The mixture was left standing for 18 hours and diluted with DCM to a total volume of 2.0 mL. This mixture was purified by silica gel chromatography (0→10% MeOH in DCM). The desired product 45 was obtained as a white residue (4.3 mg, 2.07 µmol, 48%). LCMS (ESI+) calculated for $C_{96}H_{136}IN_9O_{35}S_4^{2+}$ (M+2H$^+$) 1037.28, found 1037.53.

Example 25: Synthesis of Linker Conjugate 46

To a solution of 40 (9.0 mg, 4.88 µmol) in DMF (445 µL) were added a solution of 22 (12.8 mg, 24.4 µmol) in DMF (45.8 µL) and a 50% v/v $Et_3N$ solution in DMF (8.98 µL, 32.2 µmol). The mixture was left standing for 4 h and then diluted with DCM to a total volume of 4.5 mL. This mixture was purified by silica gel chromatography (0→20% MeOH in DCM). The desired product 46 was obtained as a colorless oil (5.0 mg, 2.24 µmole, 46%). LCMS (ESI+) calculated for $C_{96}H_{136}IN_9O_{35}S_4^{2+}$ (M+2H$^+$) 1115.35, found 1115.40.

Examples 26-34: Conjugation of Linker-Payloads to Modified Monoclonal Antibodies

Example 26: Conjugation of Huk5-70-2-(6-N$_3$-GalNAc)$_2$ with BCN-HS-(vc-PABC-MMAE)$_2$ 41 to Obtain Conjugate I-41

To a solution of Huk5-70-2-(6-N$_3$-GalNAc)$_2$ (435 µL, 8.0 mg, 18.4 mg/ml in PBS pH 7.4) was added BCN-HS-(vc-PABC-MMAE)$_2$ 41 (27.5 µL, 20 mM solution in DMF) and propylene glycol (313 µL). The reaction was incubated overnight at rt. Next the conjugate was purified on a HiLoad 26/600 Superdex200 PG column (GE Healthcare) on an AKTA Purifier-10 (GE Healthcare). Mass spectral analysis of the sample after IdeS treatment showed one major Fc/2 product (observed mass 27154 Da, approximately 90% of total Fc/2), corresponding to the conjugate I-41. RP-HPLC analysis of the sample under reducing conditions showed an average DAR of 3.68.

Example 27: Conjugation of hRS7-(6-N$_3$-GalNAc)$_2$ with BCN-HS-(vc-PABC-MMAE)$_2$ 41 to Obtain Conjugate II-41

To a solution of hRS7-(6-N$_3$-GalNAc)$_2$ (350 µL, 7.0 mg, 20.0 mg/mL in PBS pH 7.4) was added BCN-HS-(vc-PABC-MMAE)$_2$ 41 (24 µL, 20 mM solution in DMF) and propylene glycol (300 µL). The reaction was incubated overnight at rt. Next the conjugate was purified on a HiLoad 26/600 Superdex200 PG column (GE Healthcare) on an AKTA Purifier-10 (GE Healthcare). Mass spectral analysis of the sample after IdeS treatment showed one major Fc/2 product (observed mass 27154 Da, approximately 90% of total Fc/2), corresponding to the conjugate II-41. RP-HPLC analysis of the sample under reducing conditions showed an average DAR of 3.88.

Example 28: Conjugation of hTINA-(6-N$_3$-GalNAc)$_2$ with BCN-HS-(vc-PABC-MMAE)$_2$ 41 to Obtain Conjugate III-41

To a solution of hTINA-(6-N$_3$-GalNAc)$_2$ (386 µL, 8.0 mg, 20.7 mg/mL in PBS pH 7.4) was added BCN-HS-(vc-PABC-MMAE)$_2$ 41 (27.5 µL, 20 mM solution in DMF) and propylene glycol (313 µL). The reaction was incubated overnight at rt. Next the conjugate was purified on a HiLoad 26/600 Superdex200 PG column (GE Healthcare) on an AKTA Purifier-10 (GE Healthcare). Mass spectral analysis of the sample after IdeS treatment showed one major Fc/2 product (observed mass 27154 Da, approximately 90% of total Fc/2), corresponding to the conjugate III-41. RP-HPLC analysis of the sample under reducing conditions showed an average DAR of 3.88.

Example 29: Conjugation of Huk5-70-2-(6-N$_3$-GalNAc)$_2$ with BCN-HS-(vc-PABC-DMEDA-SN-38)$_2$ 42 to Obtain Conjugate I-42

To a solution of Huk5-70-2-(6-N$_3$-GalNAc)$_2$ (165 µL, 3.0 mg, 18.4 mg/mL in PBS pH 7.4) was added BCN-HS-(vc-PABC-DMEDA-SN-38)$_2$ 42 (20 µL, 10 mM solution in DMF) and propylene glycol (165 µL). The reaction was incubated overnight at rt. Next the conjugate was purified on a HiLoad 26/600 Superdex200 PG column (GE Healthcare) on an AKTA Purifier-10 (GE Healthcare). Mass spectral analysis of the sample after IdeS treatment showed one major Fc/2 product (observed mass 26750 Da, approximately 90% of total Fc/2), corresponding to the conjugate I-42. RP-HPLC analysis of the sample under reducing conditions showed an average DAR of 3.60.

Example 30: Conjugation of Huk5-70-2-(6-N$_3$-GalNAc)$_2$ with BCN-HS-(vc-PABC-amanitin)$_2$ 43 to Obtain Conjugate I-43

To a solution of Huk5-70-2-(6-N$_3$-GalNAc)$_2$ (82 µL, 1.5 mg, 18.4 mg/mL in PBS pH 7.4) was added BCN-HS-(vc-PABC-amanitin)$_2$ 43 (10 µL, 5 mM solution in DMF). The reaction was incubated overnight at rt. Next the conjugate was purified on a HiLoad 26/600 Superdex200 PG column (GE Healthcare) on an AKTA Purifier-10 (GE Healthcare). Mass spectral analysis of the sample after IdeS treatment showed one major Fc/2 product (observed mass 27727 Da, approximately 90% of total Fc/2), corresponding to the conjugate I-43.

Example 31: Conjugation of Huk5-70-2-(6N$_3$-GalNAc)$_2$ with BCN-HS-(vc-PABC-bleomycin)$_2$ 44 to Obtain Conjugate I-44

To a solution of Huk5-70-2-(6-N$_3$-GalNAc)$_2$ (109 µL, 2.0 mg, 18.4 mg/mL in PBS pH 7.4) was added BCN-HS-(vc-PABC-bleomycin)$_2$ 44 (10 µL, 10 mM solution in DMF). The reaction was incubated overnight at rt. Next the conjugate was purified on a HiLoad 26/600 Superdex200 PG column (GE Healthcare) on an AKTA Purifier-10 (GE Healthcare). Mass spectral analysis of the sample after IdeS treatment showed one major Fc/2 product (observed mass 28571 Da, approximately 90% of total Fc/2), corresponding to the conjugate I-44.

Example 32: Conjugation of Huk5-70-2-(6N$_3$-GalNAc)$_2$ with BCN-HS-va-PABC-calicheamicin 45 to Obtain Conjugate I-45

To a solution of Huk5-70-2-(6-N$_3$-GalNAc)$_2$ (109 µL, 2.0 mg, 18.4 mg/mL in PBS pH 7.4) was added BCN-HS-va-PABC-calicheamicin 45 (4.5 µL, 20 mM solution in DMF) and 80 µL PG. The reaction was incubated overnight at rt. Next the conjugate was purified on a HiLoad 26/600 Superdex200 PG column (GE Healthcare) on an AKTA Purifier-10 (GE Healthcare). Mass spectral analysis of the sample after IdeS treatment showed one major Fc/2 product (observed mass 26438 Da, approximately 90% of total Fc/2), corresponding to the conjugate I-45.

Example 33: Conjugation of Huk5-70-2-(6-N$_3$-GalNAc)$_2$ with BCN-HS-va-PABC-calicheamicin 46 to Obtain Conjugate I-46

To a solution of Huk5-70-2-(6-N$_3$-GalNAc)$_2$ (94 µL, 1.5 mg, 16.0 mg/ml in PBS pH 7.4) was added BCN-HS-va-PABC-calicheamicin 46 (1.2 µL, 40 mM solution in DMF) and 30 µL PG. The reaction was incubated overnight at rt. Next the conjugate was purified on a HiLoad 26/600 Superdex200 PG column (GE Healthcare) on an AKTA Purifier-10 (GE Healthcare). Mass spectral analysis of the sample after IdeS treatment showed one major Fc/2 product (observed mass 26595 Da, approximately 90% of total Fc/2), corresponding to the conjugate I-46.

Example 34. Conjugation of hRS7-(6-N$_3$-GalNAc)$_2$ with BCN-HS-vc-PABC-calicheamicin 46 to Obtain Conjugate II-46

To a solution of hRS7-(6-N$_3$-GalNAc)$_2$ (81 µL, 1.5 mg, 18.5 mg/ml in PBS pH 7.4) was added BCN-HS-va-PABCcalicheamicin 46 (1.2 µL, 40 mM solution in DMF) and 60 µL PG. The reaction was incubated overnight at rt. Next the conjugate was purified on a HiLoad 26/600 Superdex200 PG column (GE Healthcare) on an AKTA Purifier-10 (GE Healthcare). Mass spectral analysis of the sample after IdeS treatment showed one major Fc/2 product (observed mass 26595 Da, approximately 90% of total Fc/2), corresponding to the conjugate II-46.

Examples 35-36: Efficacy Studies

Example 35: Cytotoxicity Assays

Compound Handling: After thawing frozen ADCs, ADCs were diluted with complete RPM11640 cell culture medium to a concentration of 150 µg/mL. Starting with this 150 µg/mL stock solution, serial half log dilutions of were done in RPM11640 cell culture medium in an intermediatelate. Finally, 10 µL taken from the intermediate dilution plate were transferred to 140 µL/well of the final assay plate.

Tumour Cell Lines: The cell lines used in this study were derived from pancreatic cancer (BxPC-3). Cell lines were either obtained from the NCI (Bethesda, MD), or were purchased from ATCC or (Rockville, MD). Authenticity of cell lines was proven at the DSMZ by STR (short tandem repeat) analysis, a PCR based DNA-fingerprinting methodology. Cell lines were routinely passaged once or twice weekly and maintained in culture for up to 20 passages. They were grown at 37° C. in a humidified atmosphere with 5% $CO_2$ in RPMI 1640 medium (25 mM HEPES, with L-glutamine, #FG1385, Biochrom, Berlin, Germany) supplemented with 10% (v/v) fetal calf serum (Sigma, Taufkirchen, Germany) and 0.05 mg/mL gentamicin (Life Technologies, Karlsruhe, Germany).

Propidium iodide-based Monolayer Assay: A modified propidium iodide (PI) based monolayer assay was used to assess the anti-cancer activity of the compounds. Briefly, cells were harvested from exponential phase cultures, counted and plated in 96 well flat-bottom microtiter plates at a cell density of 8,000 to 30,000 cells/well dependent on the cell line's growth rate. The individual seeding density for each cell line ensure exponential growth conditions over the whole or at least the bigger part of the treatment period. After a 24 h recovery period, to allow the cells to resume exponential growth, 10 µL of culture medium (6 control wells/cell line/plate) or of culture medium with test compounds were added. Compounds were applied at ten concentrations in half-log increments in duplicates up to 10 µg/mL and treatment continued for five days. After five days of treatment, cells were next washed with 200 µL PBS to remove dead cells and debris, then 200 µL of a solution containing 7 µg/mL propidium iodide (PI) and 0.1% (v/v) Triton X-100 was added. After an incubation period of 1-2 hours at room temperature, fluorescence was measured using the Enspire Multimode Plate Reader (excitation $\lambda=530$ nm, emission $\lambda=620$ nm) to quantify the amount of attached viable cells.

Figure 6:
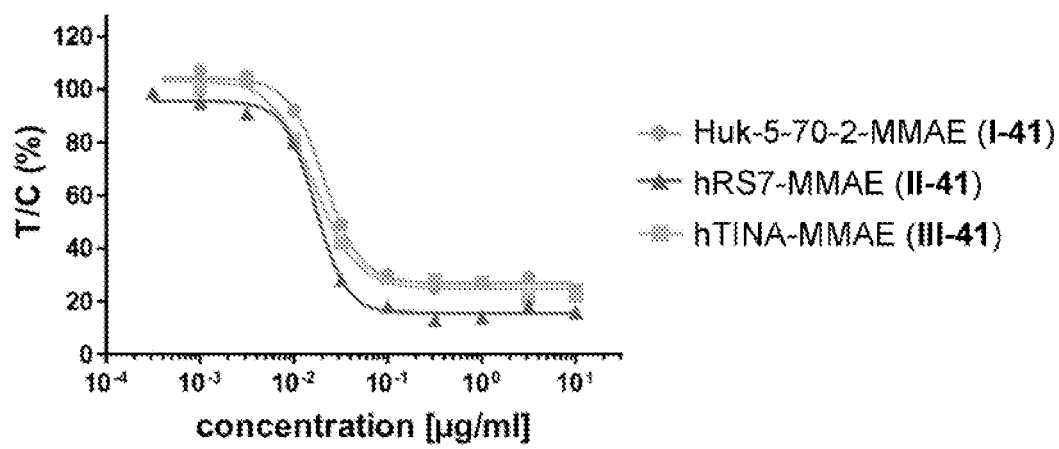
FIG. 6 shows the cytotoxicity of ADCs prepared on a range of antibodies conjugated to MMAE (BxPC-3 cell line). T/C %=test/control percentage.
Figure 7:
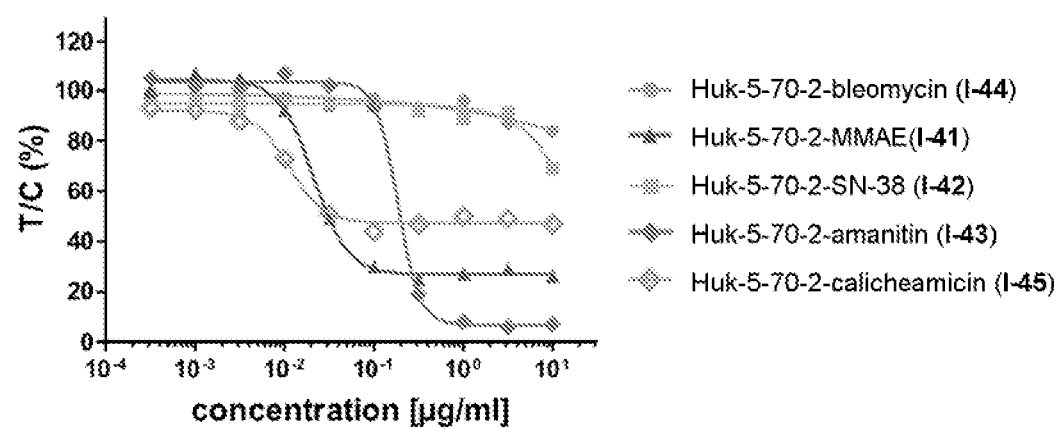
FIG. 7 shows the cytotoxicity of ADCs based on antibody Huk5-70-2 conjugated to a range of toxic payloads (BxPC-3 cell line). T/C %=test/control percentage.

Read-out of the various cytotoxicity assays is graphically depicted in FIGS. 6 and 7, showing a clear dependency of cytotoxicity on the nature of the antibody by keeping the payload constant (FIG. 6) and a clear dependency of cytotoxicity on the nature of the payload by keeping the antibody constant (FIG. 7).

Example 36: In Vivo Efficacy Study (Performed at Altogen Lab, Austin, TX)

BxPC-3 cell line was cultured in vitro to generate at least 165 million cells using ATCC-formulated RPMI-1640 medium supplemented with 10% FBS (ATCC) in humidified cell culture incubator at 37° C. with standard 5% $CO_2$ specs. Cells were passaged at 1:5 split ratio at 80-90% confluency. The cells in an exponential growth phase were harvested and counted for tumour inoculation.

Nude mice (NU(NCr)-Foxn1nu nude mice, female) of 10-12 weeks old received a subcutaneous injection of 1 million cells (50% matrigel protocol per Altogen Labs SOP 6.012) following Altogen Labs IACUC protocol. When tumours reached an average size of 100-150 mm³, a pair match was performed and treatment began.

Electronic calliper measurement was performed 2 times a week. Daily observations for clinical signs, food and water consumption, behavioral changes, animals were weighed 2 times per week. The endpoint of the experiment is a tumour volume of 2,000 mm³ or 45 days, whichever comes first.

Group assignment: Before grouping and treatment, all animals are weighed and the tumour volumes confirmed (100-150 mm³) using electronic calliper. Since the tumour volume can affect the effectiveness of any given treatment, mice assigned into groups using randomized block design as following: First, the experimental animals are divided into homogeneous blocks based on their tumour volume. Secondly, within each block, randomization of experimental animals to different groups conducted. By using randomized block design to assign experimental animals, we ensure that each animal has the same probability of being assigned to any given treatment groups and therefore systematic error is minimized.

Test article administration: Administration of compounds performed using Genie Touch Syringe Pump (Kent Scientific). Metered syringe pump programmed to deliver the injection. Terumo Surshield safety winged infusion sets (S25BLS, 25Gx3/4) are used for the administration. Twenty percent (20%) of extra volume prepared and loaded into syringe (Kent Scientific) to ensure sufficient injection volume once the tubing is filled with the compound. All work performed in a Biological Safety Cabinet to prepare the samples and load sample into syringe. New syringe used for each individual test article and control group samples.

Observation and data collection: After tumour cells inoculation, the animals are checked daily for morbidity and mortality. At the time of routine monitoring, the animals are checked for any adverse effects of tumour growth and treatments on normal behaviour such as mobility, visual estimation of food and water consumption, body weight gain/loss, eye/hair matting and any other abnormal effects. Death and observed clinical signs are recorded per Altogen Labs IACUC. Tumour volumes are measured every 3-4 days in two dimensions using an electronic calliper, and the volume data are expressed in mm³ using the formula: $V=0.5 \text{ a} \times b^2$ where a and b are the long and short diameters of the tumour, respectively. Dosing and tumour volume measurement procedures are conducted in a Laminar Flow Cabinet according to Altogen Labs IACUC regulations.

TABLE 1

Overview of test items and dose levels included in in vivo study

| Test item | Dose levels (mg/kg) | Group (n = 6) | Administration | Dosing Schedule |
|---|---|---|---|---|
| hRS7-CM | 0.05 | 1 | IV | Single dose |
| (II-46) | 0.3 | 2 | IV | Single dose |
| hRS7-amanitin | 2 | 3 | IV | Single dose |
| (II-43) | 7 | 4 | IV | Single dose |
| hRS7-MMAE | 1 | 5 | IV | Single dose |
| (II-41) | 5 | 6 | IV | Single dose |
|  | 10 | 7 | IV | Single dose |
| Huk5-70-2-CM | 0.05 | 8 | IV | Single dose |
| (I-46) | 0.3 | 9 | IV | Single dose |
| Huk5-70-2-amanitin | 2 | 10 | IV | Single dose |
| (I-43) | 7 | 11 | IV | Single dose |

TABLE 1-continued

Overview of test items and dose levels included in in vivo study

| Test item | Dose levels (mg/kg) | Group (n = 6) | Administration | Dosing Schedule |
|---|---|---|---|---|
| hRS7-SN38 (IMMU-132) | 15 | 16 | IV | Single dose |
|  | 30 | 17 | IV | Single dose |
| Huk5-70-2-DXd (DS-1062a) | 2 | 18 | IV | Single dose |
|  | 7 | 19 | IV | Single dose |
| vehicle | — | 20 | IV | Single dose |

Figure 8:
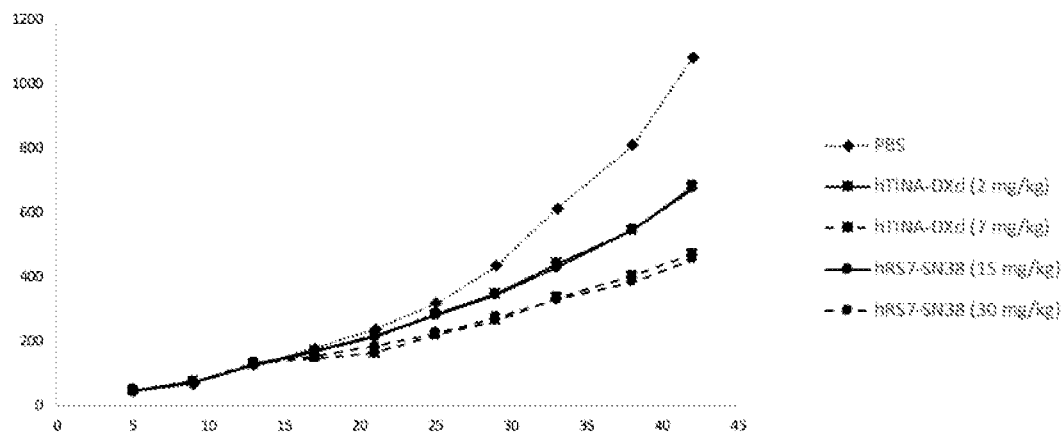
FIG. 8 depicts the results of the efficacy studies described in Example 36 for antibody-drug conjugates IMMU-132 (prepared by conjugation of CL2-SN-38 to hRS7, according to Moon et al., *J. Med. Chem.* 2008, 51, 6916-6926, incorporated by reference) and DS-1062a (prepared by conjugation of DXd to hTINA1, according to US20160297890, incorporated by reference).
Figure 9:
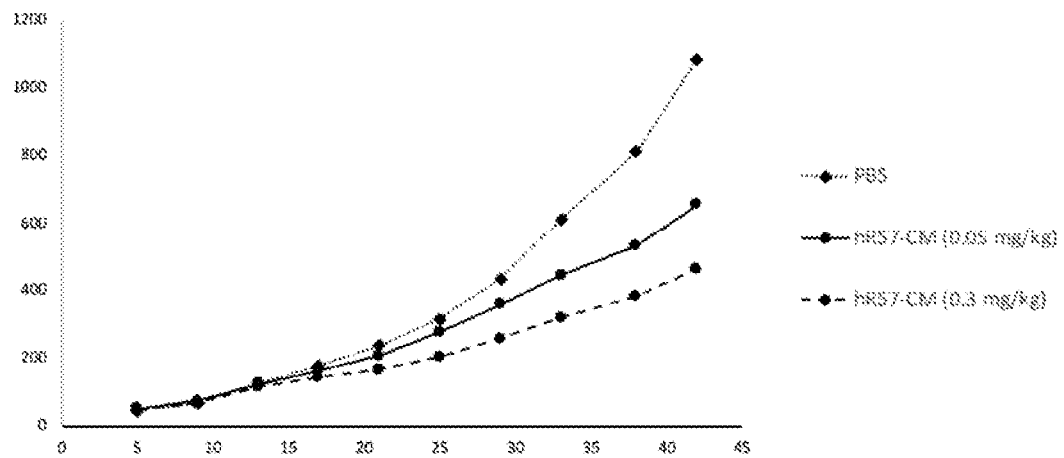
FIG. 9 depicts the results of the efficacy studies described in Example 36 for antibody-drug conjugate hRS7-calicheamicin (II-46).
Figure 10:
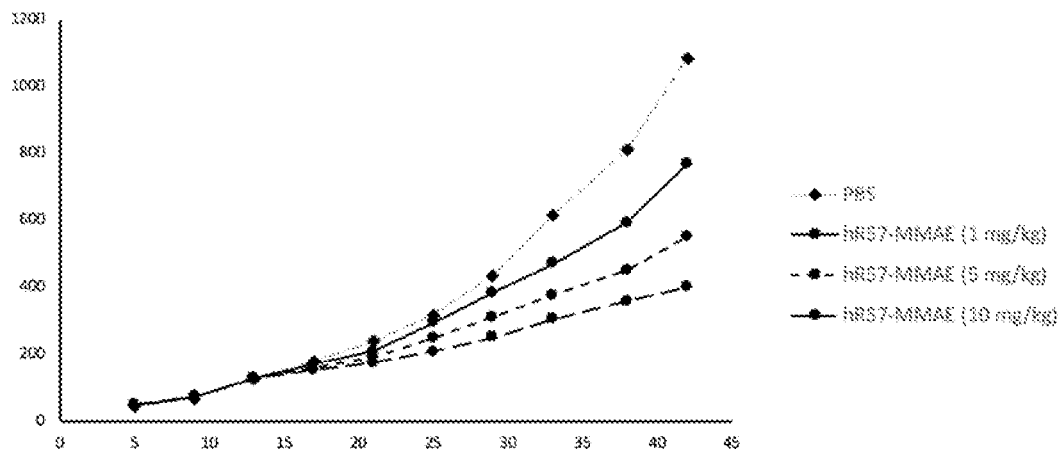
FIG. 10 depicts the results of the efficacy studies described in Example 36 for antibody-drug conjugate hRS7-MMAE (II-41).
Figure 11:
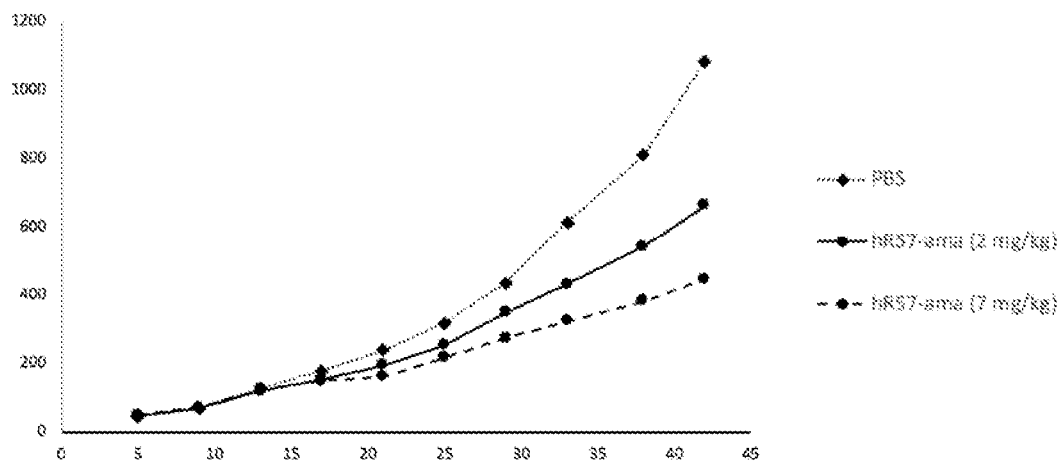
FIG. 11 depicts the results of the efficacy studies described in Example 36 for antibody-drug conjugate hRS7-amanitin (II-43).
Figure 12:
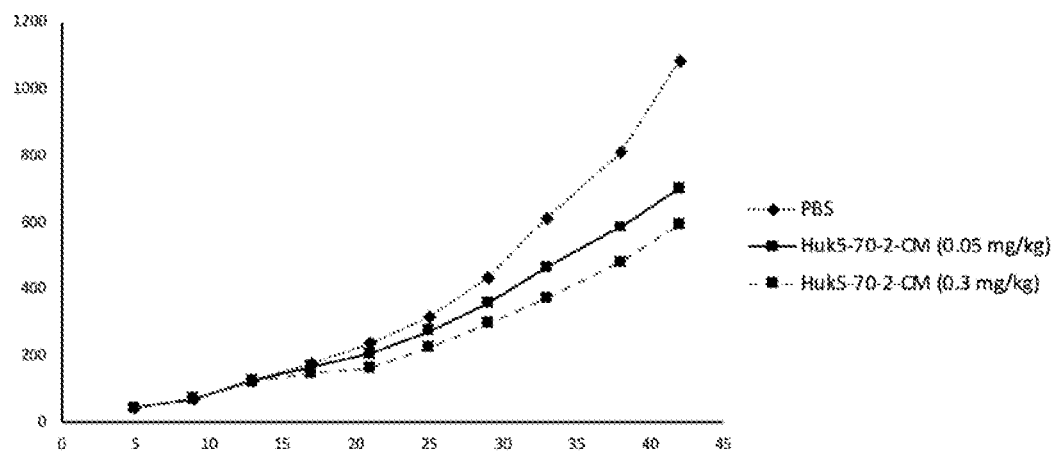
FIG. 12 depicts the results of the efficacy studies described in Example 36 for antibody-drug conjugate Huk5-70-2-calicheamicin (I-45).
Figure 13:
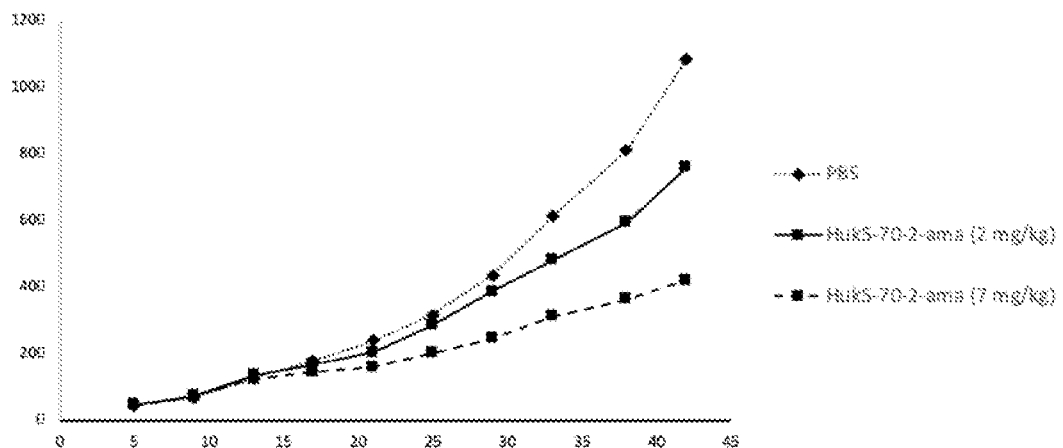
FIG. 13 depicts the results of the efficacy studies described in Example 36 for antibody-drug conjugate Huk5-70-2-amanitin (I-43).

Data for efficacy study with hRS7-calicheamicin (II-46) are depicted in FIG. 9, data for efficacy study with hRS7-amanitin (II-43) are depicted in FIG. 10, data for efficacy study with hRS7-MMAE (II-41) are depicted in FIG. 11, data for efficacy study with Huk5-70-2-calicheamicin (I-46) are depicted in FIG. 12, data for efficacy study with Huk5-70-2-amanitin (I-43) are depicted in FIG. 13, data for efficacy study with hRS7-SN-38 and hTINA-DXd are depicted in FIG. 8.

The invention claimed is:

1. An antibody-conjugate according to general structure (2):

$$AB\text{-}[(L^6)\text{-}\{Z\text{---}(L^1)_n\text{---}(L^2)_o\text{---}(L^3)_p\text{---}(L^4)_q\text{-}D\}_{xx}]_{yy} \quad (2)$$

wherein:
AB is an antibody capable of targeting Trop-2-expressing tumours;
$L^1$, $L^2$, $L^3$ and $L^4$ are each individually linkers that together link Z to D;
n, o, p and q are each individually 0 or 1, provided that n+o+p+q is 1, 2, 3 or 4;
Z is a connecting group;
$L'$ is —GlcNAc(Fuc)$_w$—S—$(L^7)_{w'}$—, wherein S is a sugar or a sugar derivative, GlcNAc is N-acetylglucosamine and Fuc is fucose, w is 0 or 1, w' is 0, 1 or 2 and $L^7$ is —N(H)C(O)CH$_2$—, —N(H) C (O) CF$_2$— or —CH$_2$—;
D is selected from the group consisting of a taxane, an anthracycline, a camptothecin, an epothilone, a mitomycin, a combretastatin, a *vinca* alkaloid, a maytansinoid, an enediyne, a duocarmycin, a tubulysin, an amatoxin, a bleomycin, a dolastatin, an auristatin, a pyrrolobenzodiazepine dimer, an indolinobenzodiazepine dimer, a radioisotope, a kinase inhibitor, a mitogen-activated protein kinase (MEK) inhibitor, and a kinesin spindle protein (KSP) inhibitor;
xx is 1 or 2;
yy is 1, 2, 3 or 4, and
wherein the antibody is a Huk5-70-2 antibody comprising a light chain variable region and a heavy chain variable region wherein the light chain variable region comprises the amino acid sequence of SEQ ID NO: 1 and the heavy chain comprises the amino acid sequence of SEQ ID NO: 2.

2. The antibody-conjugate according to claim 1, wherein Z comprises the reaction product of a click reaction or cycloaddition reaction.

3. The antibody-conjugate according to claim 2, wherein Z comprises a triazole moiety.

4. The antibody-conjugate according to claim 3, wherein Z is according (Ze), (Zf) or (Zi):

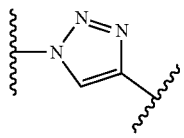

(Ze)

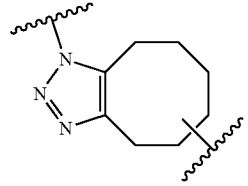

(Zf)

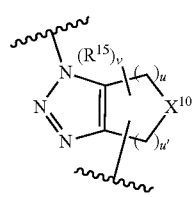

(Zi)

wherein:
$R^{15}$ is independently selected from the group consisting of hydrogen, halogen, —OR$^{16}$, —NO$_2$, —CN, —S(O)$_2$R$^{16}$, C$_1$-C$_{24}$ alkyl, C$_6$-C$_{24}$ (hetero) aryl, C$_7$-C$_{24}$ alkyl (hetero) aryl and C$_7$-C$_{24}$ (hetero) arylalkyl, or two R$^{15}$ groups are taken together to form a annulated cycloalkyl or an annulated (hetero) arene substituent, wherein R$^{16}$ is independently selected from the group consisting of hydrogen, halogen, C$_1$-C$_{24}$ alkyl, C$_6$-C$_{24}$ (hetero) aryl, C$_7$-C$_{24}$ alkyl (hetero) aryl and C$_7$-C$_{24}$ (hetero) arylalkyl;
$X^{10}$ is C (R$^{31}$) 2, O, S or NR$^{31}$, wherein each R$^{31}$ is individually R$^{15}$ or —(L$^1$)$_n$—(L$^2$)$_o$—(L$^3$)$_p$—(L$^4$)$_q$-D;
u and u' are each individually 0, 1, 2, 3, 4 or 5, provided that u+u' is 5; and
v is 8, 9 or 10.

5. The antibody-conjugate according to claim 1, wherein the GlcNAc (Fuc) w moiety is directly bonded to a peptide chain of the antibody AB.

6. The antibody-conjugate according to claim 1, wherein n, o, and p are each 1.

7. The antibody-conjugate according to claim 1, wherein:
(a) linker $L^1$ is represented by:

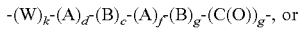

or

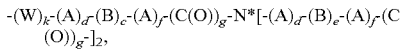

wherein:
d and d' are individually 0 or 1;
e and e' are individually an integer in the range 1-10;
f and f' are individually 0, or 1;
g and g' are individually an integer in the range 0-10;
k is 0 or 1 with the proviso that if k is 1 then d is 0;
A is a sulfamide group according to structure (23):

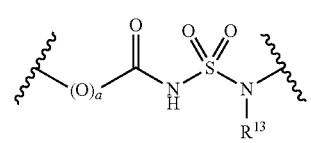

(23)

wherein a is 0 or 1, and $R^{13}$ is selected from the group consisting of hydrogen, C$_1$-C$_{24}$ alkyl, C$_3$-C$_{24}$ cycloalkyl, C$_2$-C$_{24}$ (hetero) aryl, C$_3$-C$_{24}$ alkyl (hetero) aryl and C$_3$-C$_{24}$ (hetero) arylalkyl, the C$_1$-C$_{24}$ alkyl, C$_3$-C$_{24}$ cycloalkyl, C$_2$-C$_{24}$ (hetero) aryl, C$_3$-C$_{24}$ alkyl (hetero) aryl and C$_3$-C$_{24}$ (hetero) arylalkyl optionally substituted and optionally interrupted by one or more heteroatoms selected from O, S and NR$^{14}$ wherein R$^{14}$ is independently selected from the group consisting of hydrogen and C$_1$-C$_4$ alkyl, or R$^{13}$ is D connected to the N via a spacer moiety;
W is —OC(O)—, —C(O)O—, —C(O)NH—, —NHC(O)—, —OC(O)NH—, —NHC(O)O—, —C(O)(CH$_2$)$_m$ C(O)—, —C(O)(CH$_2$)$_m$C(O)NH— or —(4-Ph)CH$_2$NHC(O)(CH$_2$)$_m$C(O)NH—, wherein m is an integer in the range 0-10;
B is a —CH$_2$—CH$_2$—O— or a —O—CH$_2$—CH$_2$— moiety, or (B) e is a —(CH$_2$—CH$_2$—O)$_{e1}$—CH$_2$—CH$_2$— moiety, wherein e1 is an integer in the range 1-10;
N* is a branching nitrogen atom, to which two instances of -(A)$_d$-(B)$_e$-(A)-(C(O))$_g$- are connected and both (C(O))$_g$ moieties are connected to —(L$^2$)$_o$—(L$^3$)$_p$—(L$^4$)$_q$-D;

and/or
(b) linker L² is a peptide spacer;
and/or
(c) linker L³ is a self-immolative spacer;
and/or
(d) linker L⁴ is an aminoalkanoic acid spacer according to the structure —NR²²($C_x$-alkylene)-C(O)—, wherein x is an integer in the range 1-20 and $R^{22}$ is H or $C_1$-$C_4$ alkyl; or linker L⁴ is a an ethyleneglycol spacer according to the structure —NR²²—(CH₂—CH₂—O)$_{e6}$—(CH₂)$_{e7}$—C(O)—, wherein e6 is an integer in the range 1-10, e7 is an integer in the range 1-3 and $R^{22}$ is H or $C_1$-$C_4$ alkyl; or linker L⁴ is a diamine spacer according to the structure —NR²²—($C_x$-alkylene)-NR²²—, wherein x is an integer in the range 1-10 and $R^{22}$ is H or $C_1$-$C_4$ alkyl.

8. The antibody-conjugate according to claim 7, wherein the spacer moiety is -(B)$_g$-(C(O))$_g$—(L²)$_o$—(L³)$_p$—(L⁴)$_q$-.

9. The antibody-conjugate according to claim 7, wherein peptide spacer is a dipeptide represented by general structure (27):

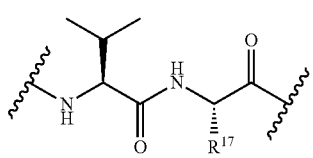

(27)

wherein R¹⁷ is CH₃ or CH₂CH₂CH₂NHC(O)NH₂.

10. The antibody-conjugate according to claim 7, wherein the self-immolative spacer is a para-aminobenzyloxycarbonyl (PABC) derivative according to structure (25):

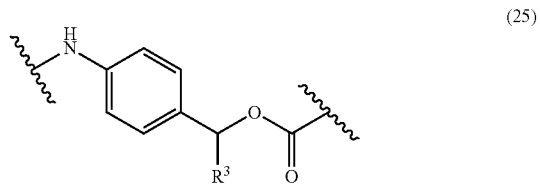

(25)

wherein $R^3$ is H, $R^4$ or C (O) $R^4$, wherein $R^4$ is $C_1$-$C_{24}$ (hetero) alkyl groups, $C_3$-$C_{10}$ (hetero) cycloalkyl groups, $C_2$-$C_{10}$ (hetero) aryl groups, $C_3$-$C_{10}$ alkyl (hetero) aryl groups and $C_3$-$C_{10}$ (hetero) arylalkyl groups, which are optionally substituted and optionally interrupted by one or more heteroatoms selected from O, S and $NR^5$ wherein $R^5$ is independently selected from the group consisting of hydrogen and $C_1$-$C_4$ alkyl groups.

11. The antibody-conjugate according to claim 10, wherein $R^3$ is H or C (O) $R^4$.

12. The antibody-conjugate according to claim 11, wherein $R^4$ is 4-methyl-piperazine or morpholine.

13. The antibody-conjugate according to claim 1, which has a structure of (XXIII):

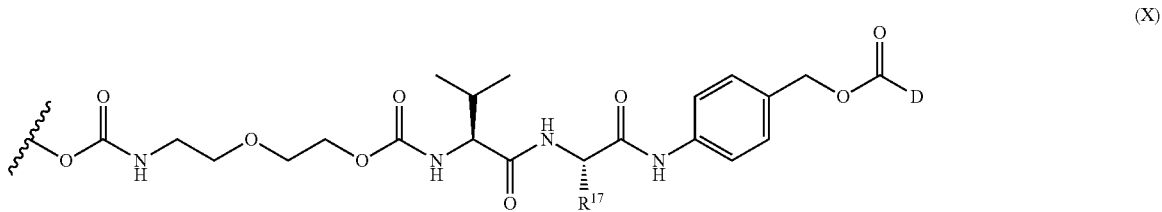

(X)

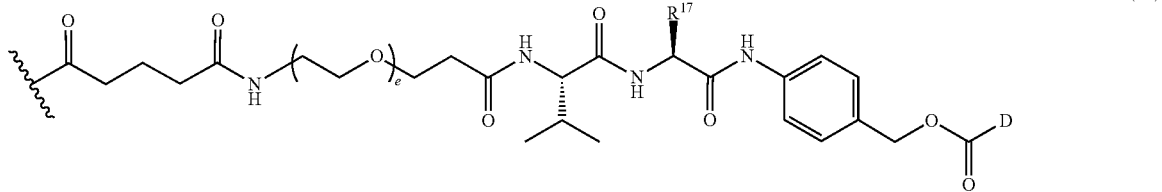

(XI)

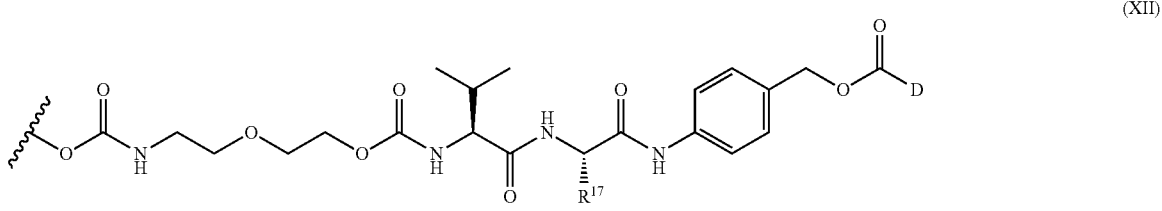

(XII)

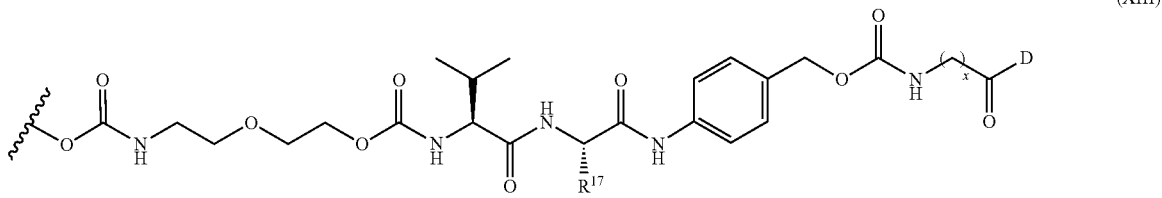

(XIII)

(XIV)
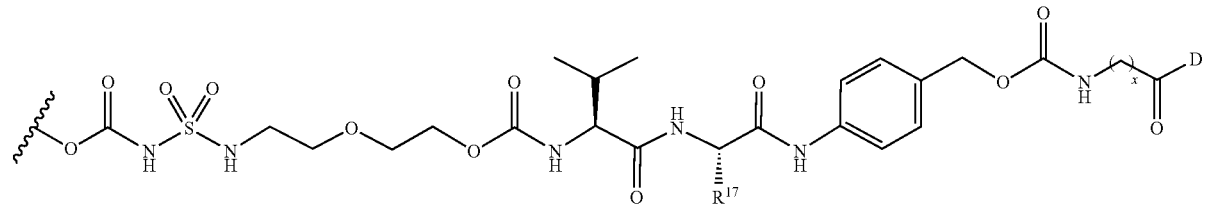
(XV)
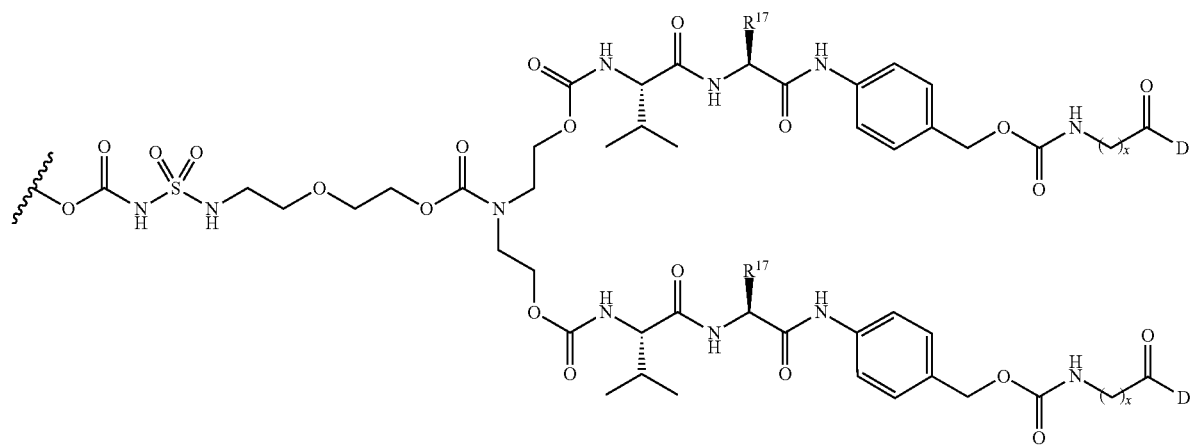
(XVI)
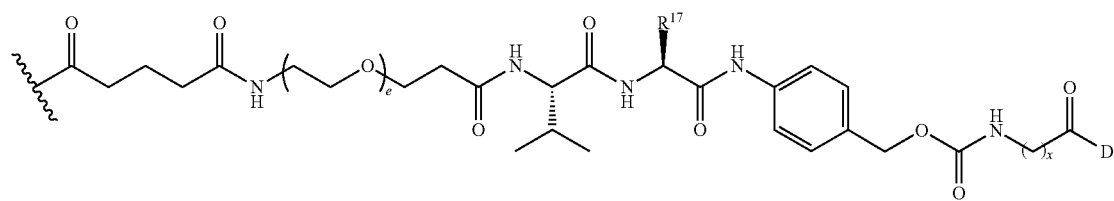
(XVII)
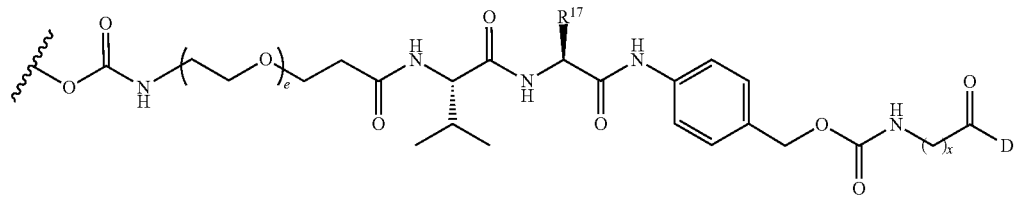
(XVIII)
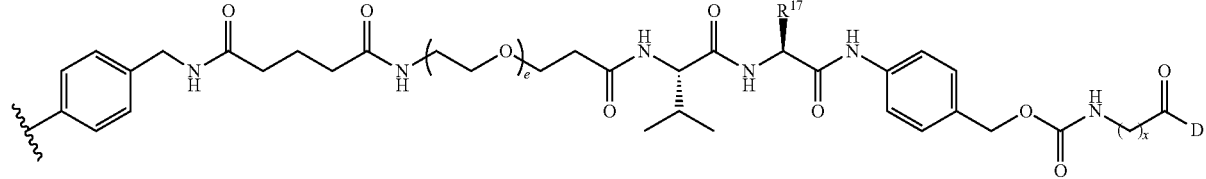
(XIX)
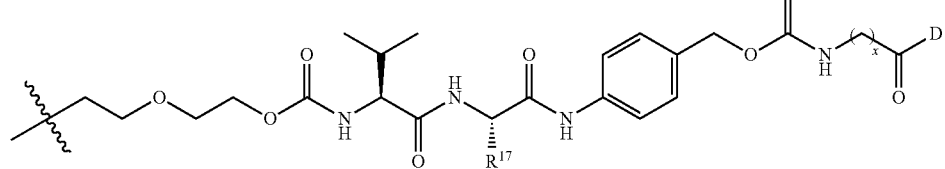

(XX)
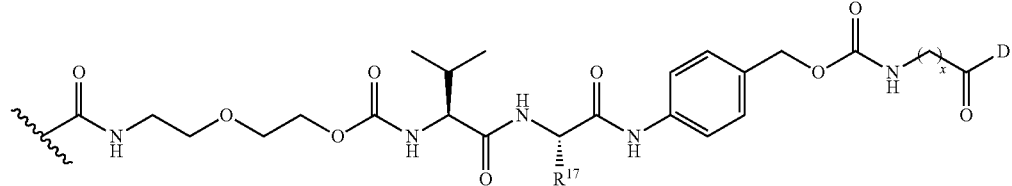
(XXI)
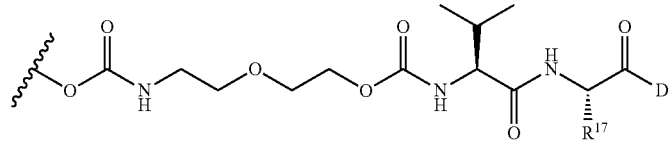
(XXII)
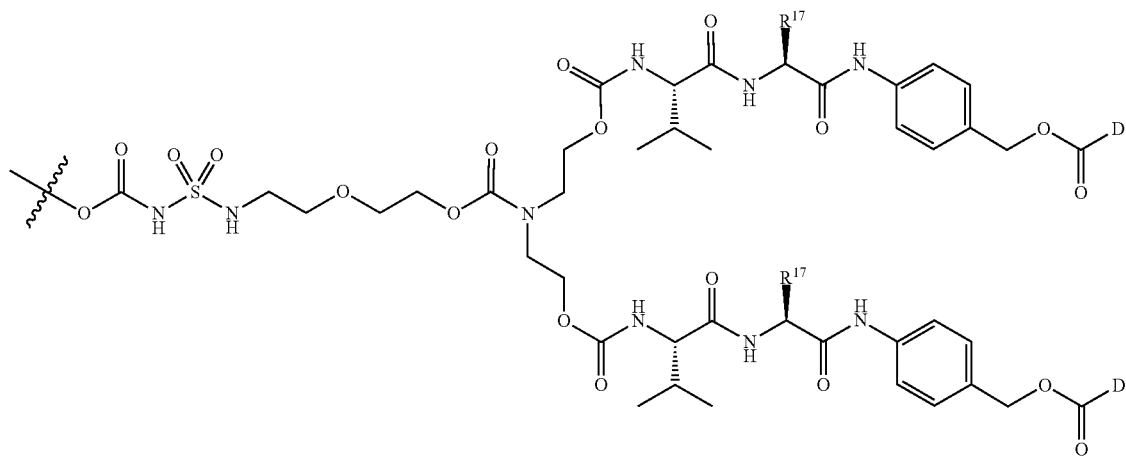
(XXIII)
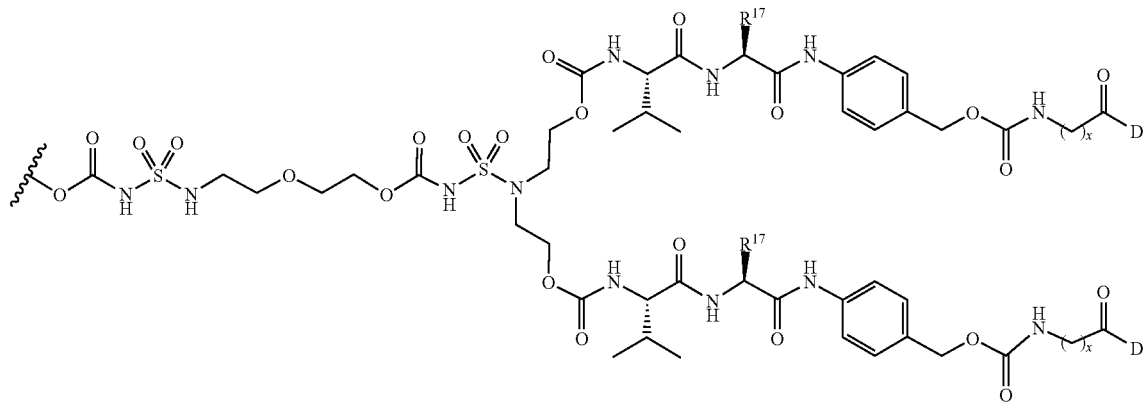

(XXIV)
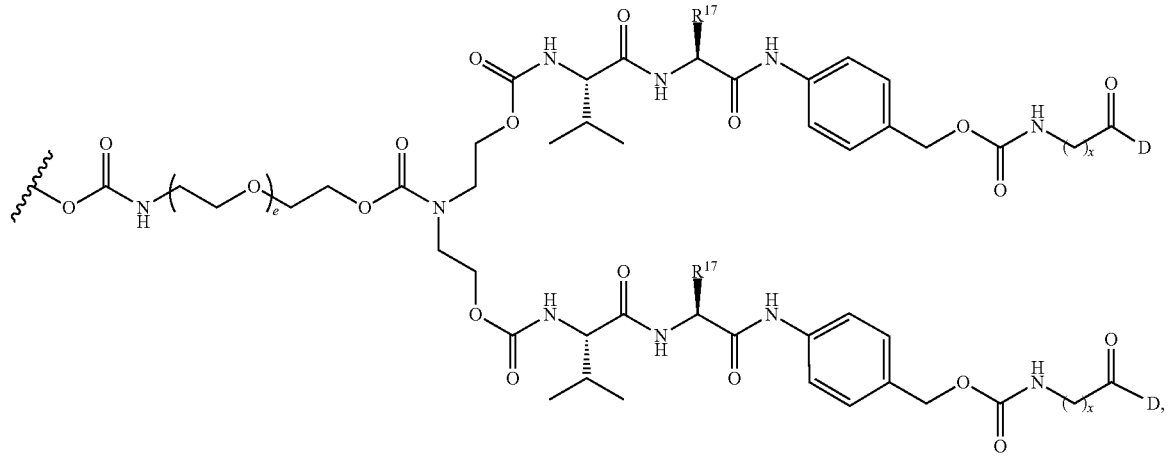
(XXV)
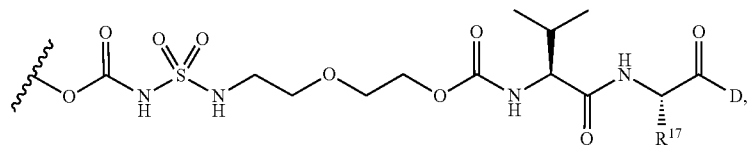
(XXVI)
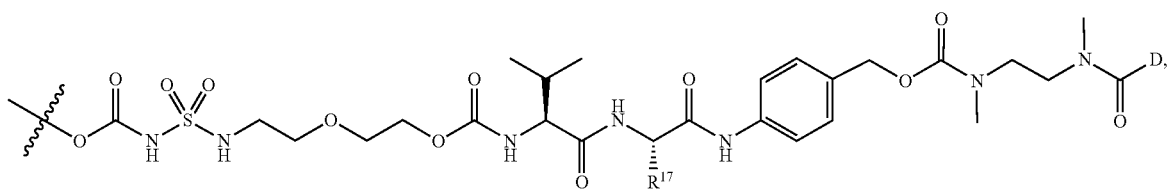
(XXVII)
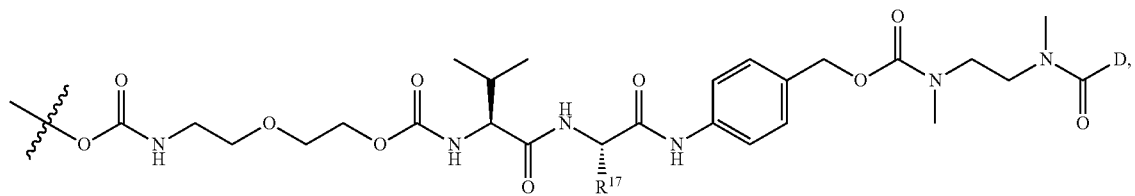
(XXVIII)
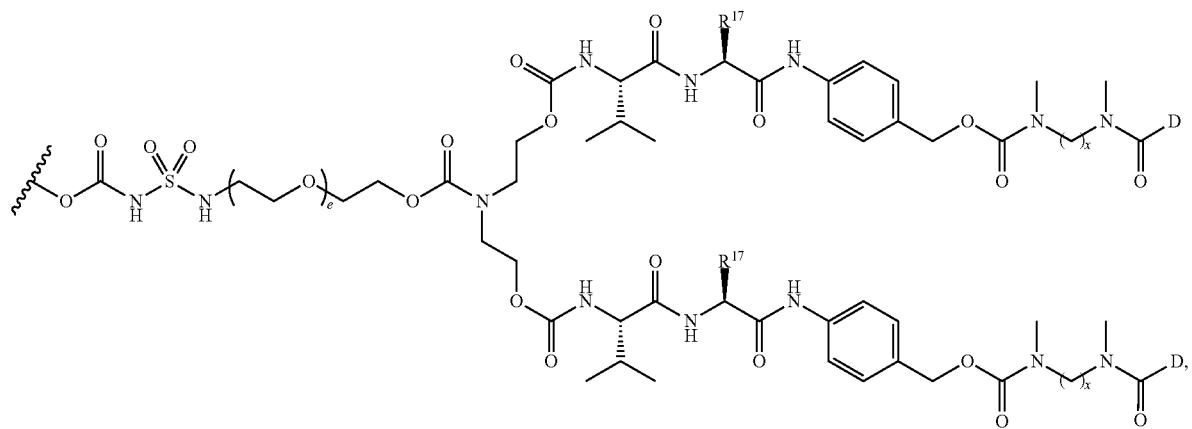

(XXIX)

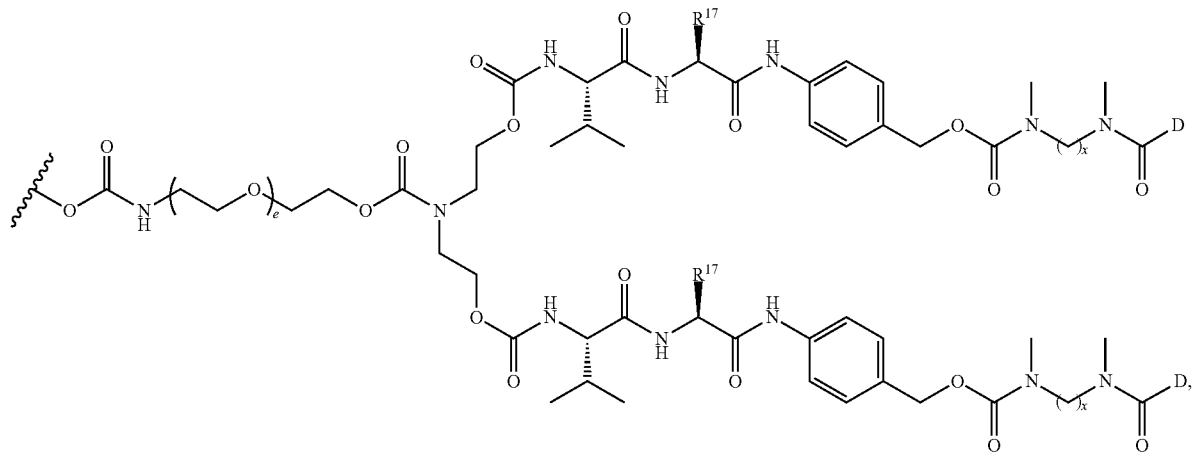

wherein the wavy line indicates the connection to Z;
$R^{17}$ is $CH_3$ or $CH_2CH_2CH_2NHC(O)NH_2$; and
x is an integer in the range 1-10.

14. The antibody-conjugate according to claim 1, wherein D is selected from the group consisting of an auristatin, an amatoxin, an enediyne, a camptothecin and a bleomycin.

15. The antibody-conjugate according to claim 1, wherein Z comprises a triazole moiety and is according to structure (Zj):

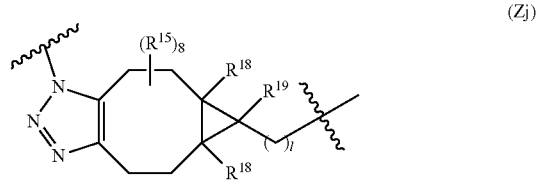

(Zj)

wherein:
$R^{15}$ is independently selected from the group consisting of hydrogen, halogen, —$OR^{16}$, —$NO_2$, —CN, —S(O)$_2R^{16}$, $C_1$-$C_{24}$ alkyl, $C_5$-$C_{24}$ (hetero) aryl, $C_7$-$C_{24}$ alkyl (hetero) aryl and $C_7$-$C_{24}$ (hetero) arylalkyl, or two $R^{15}$ groups are taken together to form an annulated cycloalkyl or an annulated (hetero) arene, wherein $R^{16}$ is independently selected from the group consisting of hydrogen, halogen, $C_1$-$C_{24}$ alkyl, $C_6$-$C_{24}$ (hetero) aryl, $C_7$-$C_{24}$ alkyl (hetero) aryl and $C_7$-$C_{24}$ (hetero) arylalkyl;
$R^{18}$ is independently selected from the group consisting of hydrogen, halogen, $C_1$-$C_{24}$ alkyl, $C_6$-$C_{24}$ (hetero) aryl, $C_7$-$C_{24}$ alkyl (hetero) aryl and $C_7$-$C_{24}$ (hetero) arylalkyl;
$R^{19}$ is selected from the group consisting of hydrogen, —$(L^1)_n$—$(L^2)_o$—$(L^3)_p$—$(L^4)_q$—D, halogen, $C_1$-$C_{24}$ alkyl, $C_6$-$C_{24}$ (hetero) aryl, $C_7$-$C_{24}$ alkyl (hetero) aryl and $C_7$-$C_{24}$ (hetero) arylalkyl, the alkyl group optionally being interrupted by one or more hetero-atoms selected from the group consisting of O, N and S; and
l is an integer in the range 0 to 10.

16. The antibody-conjugate according to claim 10, wherein:
(I) AB is Huk5-70-2; S is GalNAc; w' is 0; $R^{15}$, $R^{18}$, and $R^{19}$ are each H; l is 1; n, o, and p are each 1; q is 0; $L^1$ is —O—C(O)—NH—S(O)$_2$—NH—(($CH_2$)$_2$O)$_2$—C(O)—N* [($CH_2$)$_2$O—]$_2$; $L^2$ is Val-Cit; $L^3$ is according to structure (25) with $R^3$ is H; D is MMAE; xx is 1; and yy is 2;
(II) AB is Huk5-70-2; S is GalNAc; w' is 0; $R^{15}$, $R^{18}$, and $R^{19}$ are each H; l is 1; n, o, and p are each 1; q is 0; $L^1$ is —O—C(O)—NH—S(O)$_2$—NH—(($CH_2$)$_2$O)$_2$—C(O)—N* [($CH_2$)$_2$O—]$_2$; $L^2$ is Val-Cit; $L^3$ is according to structure (25) with $R^3$ is H; D is SN-38; xx is 1; and yy is 2;
(III) AB is Huk5-70-2; S is GalNAc; w' is 0; $R^{15}$, $R^{18}$, and $R^{19}$ are each H; l is 1; n, o, and p are each 1; q is 1; $L^1$ is —O—C(O)—NH—S(O)$_2$—NH—(($CH_2$)$_2$O)$_2$—C(O)—N* [($CH_2$)$_2$O-]$_2$; $L^2$ is Val-Cit; $L^3$ is according to structure (25) with $R^3$ is H; $L^4$ is —$NR^{22}$-($C_x$-alkylene)-$NR^{22}$—, wherein x is 5 and $R^{22}$ is Me; D is β-amanitin; xx is 1; and yy is 2;
(IV) AB is Huk5-70-2; S is GalNAc; w' is 0; $R^{15}$, $R^{18}$, and $R^{19}$ are each H; l is 1; n, o, and p are each 1; q is 0; $L^1$ is —O—C(O)—NH—S(O)$_2$—NH—(($CH_2$)$_2$O)$_2$—C(O)—N* [($CH_2$)$_2$O-]$_2$; $L^2$ is Val-Cit; $L^3$ is according to structure (25) with $R^3$ is H; D is bleomycin; xx is 1; and yy is 2;
(V) AB is Huk5-70-2; S is GalNAc; w' is 0; $R^{15}$, $R^{18}$, and $R^{19}$ are each H; l is 1; n, o, and p are each 1; q is 0; $L^1$ is —O—C(O)—NH—S(O)$_2$—NH—(($CH_2$)$_2$O)$_2$—C(O)—N* [($CH_2$)$_2$O-]$_2$; $L^2$ is Val-Cit; $L^3$ is according to structure (25) with $R^3$ is H; D is calicheamicin; xx is 1; and yy is 2.

17. The antibody-conjugate according to claim 14, wherein the enediyne is selected from the group consisting of calicheamicin, speramicin, shishijimicin and namenamicin.

18. The antibody-conjugate according to claim 14, wherein the auristatin is selected from the group consisting of MMAE, MMAF or MMAD.

19. The antibody-conjugate according to claim 14, wherein the amatoxin is selected from the group consisting of α-amanitin, β-amanitin, γ-amanitin, ε-amanitin, amanullin, amanullinic acid, amaninamide, amanin and proamanullin.

20. The antibody-conjugate according to claim 14, wherein the camptothecin is SN-38.

21. The antibody-conjugate according to claim 14, wherein D is bleomycin.

* * * * *